United States Patent
Zhang et al.

(10) Patent No.: US 8,530,652 B2
(45) Date of Patent: *Sep. 10, 2013

(54) PYRROLOPYRAZOLES, POTENT KINASE INHIBITORS

(75) Inventors: Junhu Zhang, San Diego, CA (US); Chuangxing Guo, San Diego, CA (US); Djamal Bouzida, San Diego, CA (US); Liming Dong, San Diego, CA (US); Haitao Li, San Diego, CA (US); Joseph Timothy Marakovits, Encinitas, CA (US); Anle Yang, San Diego, CA (US); Yufeng Hong, San Diego, CA (US)

(73) Assignees: Agouron Pharmaceuticals, Inc., San Diego, CA (US); Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/267,302

(22) Filed: Oct. 6, 2011

(65) Prior Publication Data
US 2012/0264751 A1 Oct. 18, 2012

Related U.S. Application Data

(63) Continuation of application No. 11/813,658, filed as application No. PCT/IB2005/003975 on Dec. 28, 2005, now Pat. No. 8,067,591.

(60) Provisional application No. 60/642,900, filed on Jan. 10, 2005, provisional application No. 60/733,770, filed on Nov. 4, 2005.

(51) Int. Cl.
*C07D 491/00* (2006.01)
*A01N 43/90* (2006.01)

(52) U.S. Cl.
USPC .................................. 544/278; 514/260.1

(58) Field of Classification Search
USPC ..................................... 544/278; 514/260.1
See application file for complete search history.

(56) References Cited

U.S. PATENT DOCUMENTS

| | | | |
|---|---|---|---|
| 3,423,414 | A | 1/1969 | Blatter |
| 3,526,633 | A | 9/1970 | Gadekar et al. |
| 3,947,467 | A | 3/1976 | Verge et al. |
| 6,013,500 | A | 1/2000 | Minden |
| 7,141,568 | B2 | 11/2006 | Fancelli et al. |
| 7,531,531 | B2 | 5/2009 | Fancelli et al. |
| 7,541,354 | B2 | 6/2009 | Fancelli et al. |
| 2003/0171357 | A1 | 9/2003 | Fancelli et al. |
| 2007/0004705 | A1 | 1/2007 | Brasca et al. |
| 2009/0221632 | A1 | 9/2009 | Fancelli et al. |

FOREIGN PATENT DOCUMENTS

| | | |
|---|---|---|
| JP | 48003639 | 2/1973 |
| JP | 51063193 | 6/1976 |
| WO | WO 02/12242 | 2/2002 |
| WO | WO 2004/013144 | 2/2004 |
| WO | WO 2004/056827 | 7/2004 |

OTHER PUBLICATIONS

Hovanessian J. general virology 1981; 52: 199-204).*
Bagrodia, S., et al., "Cdc42 and PAK-Mediated signaling Leads to Jun Kinase and p38 Mitogen-Activated Protein Kinase Activation," *The Journal of Biological Chemistry*, 1995, 27995-24998, vol. 270, No. 2.
Brown, J., et al., "Human Ste20 Homologue hPAK1 Links GTPases to the JNK MAP Kinase Pathway," *Current Biology*, 1996, 598-605, vol. 6, No. 5.
Daniels, R., et al., "p21-Activated Protein Kinase : A Crucial Component of Morphological Signaling ?In ," *Trends Biochemical Science*, 1999, 350-355, vol. 24.
Gnesutta, N., et al., "The serine/Threonine Kinase PAK[4] Prevents Caspase Activation and Protects Cells From Apoptosis," *The Journal of Biological Chemistry*, 2001, 14414-14419, vol. 276, No. 17.
King, A., et al., "The Protein Kinase Pak3 Positively Regulates Raf-1 Activity Through Phosphorylation of Serine 338," *Nature*, 1998, 180-183, vol. 396.
Manser, E., et al., "A brain Serine/Threonine Protein Kinase Activated by Cdc42 and Rac1," *Nature*, 1994, 40-46, viol. 367.
Qu, J., et al., "Activated PAK4 Regulates Cell Adhesion and Anchorage-Independent Growth," *Molecular and Cellular Biology*, 2001, 3523-3533, vol. 21, No. 10.
Roig, J., et al., "p21-Activated Protein Kinase y-PAK is Activated by Ionizing Radiation and Other DNA-Damaging Agents," *The Journal of Biological Chemistry*, 1999, 31119-31122, vol. 274, No. 44.
Rudel, T., et al., "Membrane and Morphological Changes in Apoptotic Cells Regulated by Caspase-Mediated activation of PAK2," *Science*, 1997, 1571-1574, vol. 276.
Schurmann, A., et al., "p21-Activiated Kinase 1 Phosphorylates the Death Agonist Bad and Protects Cells From Apoptosis," *Molecular and Cellular Biology*, 2000, 453-461, vol. 20.
Sells, M., et al., "Emerging From the Pak : The p21-Activated Protein Kinase Family," *Trends in Cell Biology*, 1997, 162-167, vol. 7.
Sun, H., et al., "Regulation of the Protein Kinase Raf-1 Oncogenic Ras Through Phosphatidylinositol 3-Kinase, Cdc42/Rac and Pak," *Current Biology*, 2000, 281-284, vol. 10.
Translation of Opposition paper in connection with Ecuador Application No. SP-07-7580, Dec. 31, 2007.
Yablonski, D., et al., "A Nck-Pak1 Signaling Module Is Required for T-Cell Receptor-Mediated Activation of NFAT, But Not of JNK," *EMBO Journal*, 1998, 5647-5657, vol. 17, No. 19.

* cited by examiner

*Primary Examiner* — Shirley V Gembeh
(74) *Attorney, Agent, or Firm* — Leslie A. Robinson

(57) ABSTRACT

Pyrrole pyrazole compounds of formula I, compositions including these compounds and methods of their use are provided. Preferred compounds of formula I have activity as protein kinase inhibitors, including as inhibitors of PAK4.

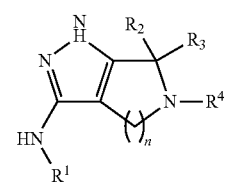

8 Claims, No Drawings

PYRROLOPYRAZOLES, POTENT KINASE INHIBITORS

This application is a Continuation of U.S. patent application Ser. No. 11/813,658 filed on Mar. 17, 2008, which is a national stage filing under 35 U.S.C. 371 of Patent Cooperation Treaty Patent Application No. PCT/IB2005/003975, filed Dec. 28, 2005, which claims the benefit of U.S. Provisional Patent Application Nos. 60/642,900 filed Jan. 10, 2005 and 60/733,770 filed Nov. 4, 2005 the disclosures of which are incorporated herein by reference in their entireties.

FIELD OF THE INVENTION

The present invention relates generally to novel chemical compounds and methods. More particularly, the invention provides novel amino pyrrolopyrazole compounds and their analogs, having protein kinase activity, and methods of synthesizing and using such compounds.

BACKGROUND

Protein kinases are a family of enzymes that catalyze phosphorylation of the hydroxyl groups of specific tyrosine, serine, or threonine residues in proteins. Typically, such phosphorylation can dramatically change the function of the protein and thus protein kinases can be pivotal in the regulation of a wide variety of cellular process, including metabolism, cell proliferation, cell differentiation, and cell survival. The mechanism of these cellular processes provides a basis for targeting protein kinases to treat disease conditions resulting from or involving disorder of these cellular processes. Examples of such diseases include, but are not limited to, cancer and diabetes.

Protein kinases can be broken into two types, protein tyrosine kinases (PTKs) and serine-threonine kinases (STKs). Both PTKs and STKs can be receptor protein kinases or non-receptor protein kinases. PAK is a family of non-receptor STKs. The p21-activated protein kinase (PAK) family of serine/threonine protein kinases plays important roles in cytoskeletal organization and cellular morphogenesis (Daniels et al., *Trends Biochem. Sci.* 24: 350-355 (1999); Sells et al., *Trends Cell. Biol.* 7: 162-167 (1997)). PAK proteins were initially identified by their interaction with the active small GTPases, Cdc42, and Rac, and their homology to yeast kinase Step 20 (Manser et al., *Nature* 367: 40-46 (1994)). In addition to mediating the regulation of actin cytoskeleton and cell adhesion by Cdc42 and Rac (Daniels et al., *Trends Biochem. Sci.* 24: 350-355 (1999)), it was determined that some PAK proteins protect cells from apoptosis (Gnesutta et al., *J. Biol. Chem.* 276: 14414-14419 (2001); Rudel et al., *Science* 276: 1571-1574 (1997); Schurmann et al., *Mol. Cell. Biol.* 20: 453-461 (2000)); modulate mitogen activated protein (MAP) kinase pathways (Bagrodia et al., *J. Biol. Chem.* 270: 27995-27998 (1995); Brown et al., *Curr. Biol.* 6: 598-605 (1996); Chaudhary et al., *Curr. Biol.* 10: 551-554 (2000); Frost et al., *EMBO J.* 16: 6426-6438 (1997); King et al., *Nature* 396: 180-183 (1998); Sun et al., *Curr. Biol.* 10: 281-284 (2000)); mediate T-cell antigen receptor (TCR) signaling (Yablonski et al., *EMBO J.* 17: 5647-5657 (1998)); and respond to DNA damage (Roig et al., *J. Biol. Chem.* 274: 31119-31122 (1999)). Through these diverse functions, PAK proteins regulate cell proliferation and migration.

The full-length PAK4 nucleic acid and amino acid sequences are disclosed in U.S. Pat. No. 6,013,500 and have been deposited in GenBank under accession numbers AF005046 (mRNA) and AAD01210 (amino acid). Modulation of human PAK4 activity is reported to result in alterations in cellular processes affecting cell growth and adhesion. For example, overexpression of PAK4 in fibroblasts leads to morphological changes that are characteristic of oncogenic transformation through induction of anchorage-independent growth and inhibition of apoptosis (Gnesutta et al., *J. Biol. Chem.* 276:14414-14419 (2001); Qu et al., *Mol. Cell. Biol.* 21: 3523-2533 (2001)).

PAK4 is an attractive target for developing therapeutic agents effective for use in processes and disorders involving cytoskeletal alterations, such as, for example, cancer.

For other background references, see U.S. Patent Application Publication No. 2003/0171357 and PCT Publication WO02/12242.

SUMMARY

In one embodiment, the invention provides a compound of formula I,

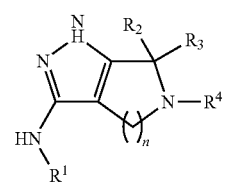

I wherein:

$R^1$ is chosen from —S(O)$R^a$, —S(O)$_2R^a$, $C_1$-$C_{12}$ alkyl, $C_1$-$C_{12}$ alkyl substituted by 1 to 6 $R^5$, $C_3$-$C_{12}$ cycloalkyl, $C_3$-$C_{12}$ cycloalkyl substituted by 1 to 6 $R^5$, $C_2$-$C_{12}$ alkenyl, $C_2$-$C_{12}$ alkenyl substituted by 1 to 6 $R^5$, $C_4$-$C_{12}$ cycloalkenyl, $C_4$-$C_{12}$ cycloalkenyl substituted by 1 to 6 $R^5$, $C_2$-$C_{12}$ alkynyl, $C_2$-$C_{12}$ alkynyl substituted by 1 to 6 $R^5$, 3-12 member heterocyclyl, 3-12 member heterocyclyl substituted by 1 to 6 $R^5$, $C_1$-$C_6$ aralkyl, $C_1$-$C_6$ aralkyl substituted by 1 to 6 $R^5$, $C_1$-$C_6$ heteroaralkyl, $C_1$-$C_6$ heteroaralkyl substituted by 1 to 6 $R^5$, $C_6$-$C_{10}$ aryl, $C_6$-$C_{10}$ aryl substituted by 1 to 6 $R^5$, 5-12 member heteroaryl, and 5-12 member heteroaryl substituted by 1 to 6 $R^5$, wherein any two adjacent $R^5$ together with the atoms to which they are attached may form a fused 4-7 member ring, and the said fused ring is optionally further substituted by 1-3 $R^f$;

$R^2$ and $R^3$ are each independently chosen from —H, $C_1$-$C_6$ perfluoroalkyl, $C_1$-$C_6$ alkyl, $C_3$-$C_6$ cycloalkyl, —($C_1$-$C_3$ alkylene)-($C_3$-$C_6$ cycloalkyl), $C_2$-$C_6$ alkenyl, $C_2$-$C_6$ alkynyl, $C_1$-$C_6$ alkoxy, -(L)$_m$-halide, -(L)$_m$-CN, -(L)$_m$-OH, -(L)$_m$-NH$_2$, -(L)$_m$-($C_1$-$C_6$ monoalkylamino) and -(L)$_m$-($C_2$-$C_8$ dialkylamino), provided that $R^2$ and $R^3$ are not both H; or $R^2$ and $R^3$ may form a ring selected from $C_3$-$C_6$ cycloalkyl, $C_4$-$C_6$ cycloalkenyl and 3-6 member heterocyclyl, the said ring is optionally further substituted by 1 to 2 groups selected from $C_1$-$C_3$ alkyl, $C_1$-$C_3$ perfluoroalkyl, $C_1$-$C_3$ alkoxy, oxo, —($C_1$-$C_3$ alkylene)$_m$-halide, —($C_1$-$C_3$ alkylene)$_m$-CN, —($C_1$-$C_3$ alkylene)$_m$-OH, —($C_1$-$C_3$ alkylene)$_m$-NH$_2$, —($C_1$-$C_3$ alkylene)$_m$-($C_1$-$C_6$ monoalkylamino) and —($C_1$-$C_3$ alkylene)$_m$-($C_2$-$C_8$ dialkylamino);

$R^4$ is selected from $R^a$, —C(O)$R^a$, —C(O)NR$^a$R$^b$, —C(O)OR$^a$, —C(O)CH(R$^t$)R$^a$, —C(O)NHCH(R$^a$)R$^b$, —C(O)OCH(R$^a$)R$^b$, —C(O)CH(R$^t$)CH(R$^a$)R$^b$, —C(O)SR$^a$, —S(O)R$^a$, —S(O)NR$^a$R$^b$, —S(O)OR$^a$, —S(O)$_2R^a$, —S(O)$_2$NR$^a$R$^b$ and —S(O)$_2$OR$^a$, wherein $R^t$ is H or $C_1$-$C_3$ alkyl;

each $R^5$ is independently selected from $R^c$, -(L)$_m$-halide, -(L)$_m$-CN, -(L)$_m$-C(O)$R^c$, -(L)$_m$-C(O)OR$^c$, -(L)$_m$-C(O)NR$^c$ $R^d$, -(L)$_m$-C(O)SR$^c$, -(L)$_m$-OR$^c$, -(L)$_m$-OC(O)R$^c$, -(L)$_m$-OC(O)NR$^c$R$^d$, -(L)$_m$-O—C(O)OR$^c$, -(L)$_m$-NO$_2$, -(L)$_m$-NR$^c$R$^d$, -(L)$_m$-N(R$^c$)C(O)R$^d$, -(L)$_m$-N(R$^c$)C(O)OR$^d$, -(L)$_m$-NR$^c$S(O)R$^d$, -(L)$_m$-NR$^c$S(O)OR$^d$, -(L)$_m$-NR$^c$S(O)$_2$R$^d$, -(L)$_m$-NR$^c$S(O)$_2$OR$^d$, -(L)$_m$-SR$^c$, -(L)$_m$-S(O)R$^c$, -(L)$_m$-S(O)OR$^c$, -(L)$_m$-S(O)$_2$R$^c$, -(L)$_m$-S(O)$_2$OR$^c$, -(L)$_m$-S(O)NR$^c$R$^d$, -(L)$_m$-S(O)$_2$NR$^c$R$^d$, -(L)$_m$-O-L-NR$^c$R$^d$, -(L)$_m$-O-L-OR$^c$ and -(L)$_m$-NR$^c$-L-OR$^d$;

each R$^a$, R$^b$, R$^c$, and R$^d$ is independently selected from H, -(L)$_m$-(C$_1$-C$_6$ perfluoroalkyl), C$_1$-C$_{12}$alkyl, —(C$_1$-C$_3$ alkylene)$_m$-(C$_3$-C$_{12}$ cycloalkyl), —(C$_3$-C$_5$ cycloalkylene)$_m$-(C$_2$-C$_{12}$ alkenyl), -(L)$_m$-(C$_4$-C$_{12}$ cycloakenyl), —(C$_3$-C$_5$ cycloalkylene)$_m$-(C$_2$-C$_{12}$alkynyl), -(L)$_m$-(3-12 member heterocyclyl), -(L)$_m$-(C$_6$-C$_{10}$ aryl) and -(L)$_m$-(5-12 member heteroaryl), each R$^a$, R$^b$, R$^c$ and R$^d$ is independently optionally further substituted by 1-6 R$^f$; R$^a$ and R$^b$, or R$^c$ and R$^d$, together with the atom to which they are attached, may optionally form a ring selected from 3-12 member heterocyclyl and 5-12 member heteroaryl, the said ring is optionally further substituted by 1-6 R$^f$;

each R$^f$ is independently selected from oxo, —(C$_1$-C$_3$ alkylene)$_m$-(C$_1$-C$_6$ perfluoalkyl), C$_1$-C$_{12}$ alkyl, C$_2$-C$_6$ alkenyl, C$_2$-C$_6$ alkynyl, —(C$_1$-C$_3$ alkylene)$_m$-(C$_3$-C$_7$ cycloalkyl), —(C$_1$-C$_3$ alkylene)$_m$-(3-7 member heterocyclyl), —(C$_1$-C$_3$ alkylene)$_m$-(5-7 member heteroaryl), -(L)$_m$-halide, -(L)$_m$-CN, -(L)$_m$-C(O)R$^k$, -(L)$_m$-C(O)OR$^k$, -(L)$_m$-C(O)NR$^k$R$^j$, -(L)$_m$-OR$^k$, -(L)$_m$-OC(O)R$^k$, -(L)$_m$-NO$_2$, -(L)$_m$-NR$^k$R$^j$, -(L)$_m$-N(R$^k$)C(O)R$^j$, -(L)$_m$-O-L-NR$^k$R$^j$, -(L)$_m$-SR$^k$, -(L)$_m$-S(O)R$^k$, -(L)$_m$-S(O)$_2$R$^j$R$^k$, each R$^f$ is independently optionally further substituted by 1-3 groups selected from C$_1$-C$_3$ alkyl, halide and C$_1$-C$_3$ perfluoroalkyl;

each R$^k$ and R$^j$ is independently —H, —OH, C$_1$-C$_3$ perfluoroalkyl, C$_1$-C$_6$ alkyl, C$_2$-C$_6$ alkenyl, C$_3$-C$_6$ alkynyl, —(C$_1$-C$_3$ alkylene)$_m$-(C$_3$-C$_6$ cycloalkyl) or —(C$_1$-C$_3$ alkylene)$_m$-(3 to 6 member heterocyclyl), R$^k$ and R$^j$ may optionally form a ring selected from 3-7 member heterocyclyl and 5-7 member heteroaryl, the said ring is optionally further substituted by 1 to 2 groups selected from C$_1$-C$_3$ alkyl, C$_1$-C$_3$ perfluoroalkyl, C$_1$-C$_3$ alkoxy, oxo, —(C$_1$-C$_3$ alkylene)$_m$-halide, —(C$_1$-C$_3$ alkylene)$_m$-CN, —(C$_1$-C$_3$ alkylene)$_m$-OH, —(C$_1$-C$_3$ alkylene)$_m$-NH$_2$, —(C$_1$-C$_3$ alkylene)$_m$-(C$_1$-C$_6$ monoalkylamino) and —(C$_1$-C$_3$ alkylene)$_m$-(C$_2$-C$_8$ dialkylamino);

each L is independently a bivalent radical selected from —(C$_1$-C$_6$ alkylene)-, —(C$_3$-C$_7$ cycloalkylene)-, —(C$_1$-C$_6$ alkylene)-(C$_3$-C$_7$ cycloalkylene)- and —(C$_3$-C$_7$ cycloalkylene)-(C$_1$-C$_6$ alkylene)-;

each m is independently 0 or 1; and n is 1, 2, or 3;

or a pharmaceutically acceptable salt, solvate or hydrate thereof.

In one particular aspect of the embodiment, and in combination of any other particular aspect not inconsistent, n is 1. More particularly, each R$^2$ and R$^3$ is independently selected from H, unsubstituted C$_1$-C$_3$ alkyl and unsubstituted C$_3$-C$_5$ cycloalkyl, or R$^2$ and R$^3$ form a ring selected from unsubstituted cyclopropyl, unsubstituted cyclobutyl and unsubstituted cyclopentyl. Even more particularly, R$^2$ is unsubstituted methyl, R$^3$ is unsubstituted methyl.

In another particular aspect of the embodiment, and in combination of any other particular aspect not inconsistent, R$^4$ is selected from —C(O)NHCH(R$^a$)R$^b$, —C(O)OCH(R$^a$)R$^b$ and —C(O)CH(R$^t$)CH(R$^a$)R$^b$. More particularly, R$^a$ is selected from —(C$_1$-C$_3$ alkylene)$_m$-phenyl, —(C$_1$-C$_3$ alkylene)$_m$-(5-12 member heteroaryl), —(C$_1$-C$_3$ alkylene)$_m$-(C$_3$-C$_{12}$ cycloalkyl) and —(C$_1$-C$_3$ alkylene)$_m$-(3-12 member heterocyclyl), and R$^a$ is optionally further substituted by 1-6 R$^f$;

R$^b$ is selected from C$_1$-C$_6$ alkyl substituted by —NR$^j$R$^k$, and —(C$_1$-C$_3$ alkylene)$_m$-(C$_3$-C$_{12}$ heterocyclyl) optionally substituted by 1-6 R$^f$. Even more particularly, R$^b$ is a methyl group substituted by —NR$^j$R$^k$. Yet even more particularly, R$^a$ is selected from phenyl, 5-12 member heteroaryl, 3-12 member heterocyclyl and 3-12 member cycloalkyl, R$^a$ is optionally further substituted by 1-6 R$^f$, and R$^b$ is a methyl group substituted by NR$^j$R$^k$.

In another particular aspect of the embodiment, and in combination of any other particular aspect not inconsistent, R$^4$ is selected from —C(O)NR$^a$R$^b$, —C(O)OR$^a$ and —C(O)CH(R)R$^a$, wherein R$^b$ is selected from H and C$_1$-C$_3$ alkyl, and R$^t$ is selected from H and C$_1$-C$_3$ alkyl. More particularly, R$^a$ is selected from —(C$_3$-C$_5$ cycloalkylene)-phenyl, —(C$_3$-C$_5$ cycloalkylene)-(5-12 member heteroaryl) and —(C$_3$-C$_5$ cycloalkylene)-(3-12 member heterocyclyl), and R$^a$ is optionally further substituted by 1-6 R$^f$. Even more particularly, R$^a$ is -(cyclopropylene)-phenyl, and R$^a$ is optionally further substituted by 1-6 R$^f$.

In another particular aspect of the embodiment, and in combination of any other particular aspect not inconsistent, n is 1, R$^4$ is —C(O)NR$^a$R$^b$, and wherein R$^a$ and R$^b$ form a ring selected from 3-12 member heterocyclyl and 5-12 member heteroaryl, the said ring contains 1-3 heteroatoms selected from N, O and S, and the said ring is optionally further substituted by 1-6 R$^f$. More particularly, the ring formed by R$^a$ and R$^b$ is selected from piperidinyl, morpholinyl, piperazinyl, pyridinyl and

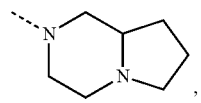

and the ring is optionally further substituted by 1-6 R$^f$.

In another particular aspect of the embodiment, and in combination of any other particular aspect not inconsistent, R$^1$ is 5-12 member heteroaryl, and R$^1$ is optionally further substituted by 1-6 R$^5$. More particularly, R$^1$ is selected from:

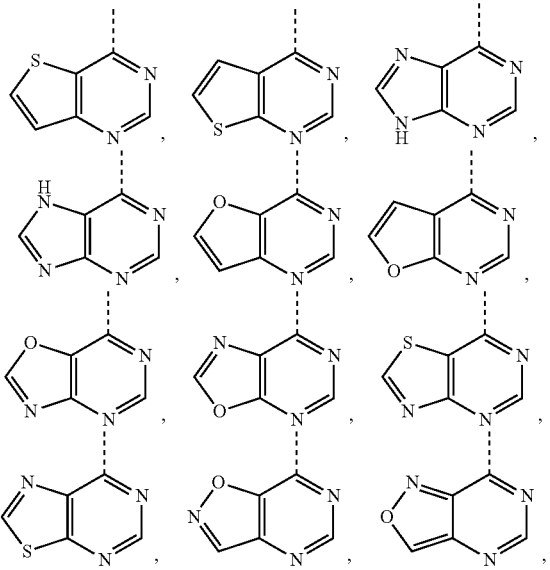

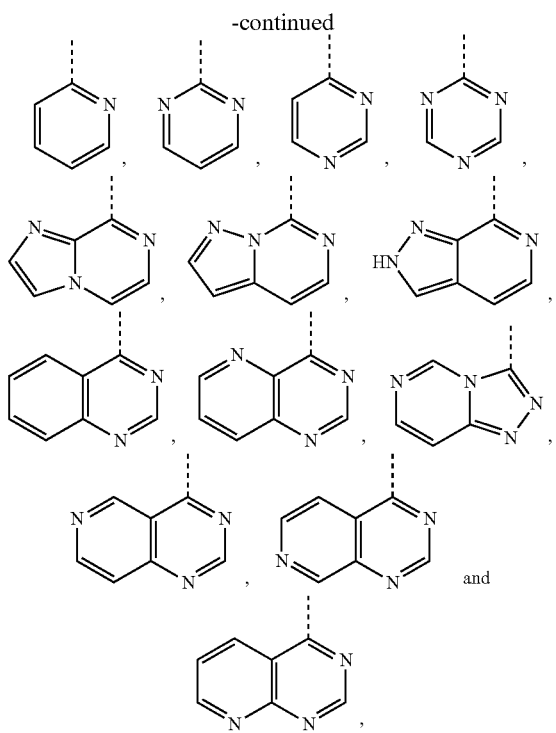

and $R^1$ is optionally further substituted as by 1-5 $R^5$. Even more particularly, each $R^5$ is independently -$(L^1)_m$-($C_1$-$C_6$ perfluoalkyl), $C_1$-$C_6$ alkyl, $C_2$-$C_6$ alkenyl, $C_2$-$C_6$ alkynyl, —($C_1$-$C_3$ alkylene)$_m$-($C_3$-$C_4$ cycloalkyl), —($C_1$-$C_3$ alkylene)$_m$-(3-4 member heterocyclyl) optionally substituted by 1-2 $C_1$-$C_3$ alkyl, -$(L^1)_m$-halide, -$(L^1)_m$-CN, -$(L^1)_m$-C(O)$R^k$, -$(L^1)_m$-C(O)O$R^k$, -$(L^1)_m$-C(O)N$R^k R^j$, -$(L^1)_m$-C(O)S$R^j$, -$(L^1)_m$-O$R^k$, -$(L^1)_m$-OC(O)$R^k$, -$(L^1)_m$-OC(O)N$R^j R^k$, -$(L^1)_m$-NO$_2$, -$(L^1)_m$-N$R^k R^j$, N($R^k$)C(O)$R^j$, -$(L^1)_m$-N($R^k$)C(O)O$R^j$, -$(L^1)_m$-O-$L^1$-N$R^k R^j$, -$(L^1)_m$-O-$L^1$-O$R^k$, -$(L^1)_m$-N$R^j$-$L^1$-O$R^k$, -$(L^1)_m$-S$R^k$, -$(L^1)_m$-S(O)$R^k$, -$(L^1)_m$-S(O)O$R^k$, -$(L^1)_m$-S(O)N$R^j R^k$, -$(L^1)_m$-S(O)$_2 R^k$, -$(L^1)_m$-S(O)$_2$O$R^k$ or -$(L^1)_m$-S(O)$_2$N$R^j R^k$, wherein each $R^j$ and $R^k$ is independently H, OH, $C_1$-$C_3$ alkyl or $C_1$-$C_3$ perfluoroalkyl, or $R^j$ and $R^k$ on the same nitrogen forms a 3-4 member ring selected from aziridinyl and azetidinyl; $L^1$ is a bivalent radical selected from —($C_1$-$C_3$ alkylene)-, —($C_3$-$C_4$ cycloalkylene)-, -(3-4 member heterocyclylene)-, —($C_1$-$C_3$ alkylene)-($C_3$-$C_4$ cycloalkylene)-, —($C_3$-$C_4$ cycloalkylene)-($C_1$-$C_3$ alkylene)-, —($C_1$-$C_3$ alkylene)-(3-4 member heterocyclylene)- and -(3-4 member heterocyclylene)-($C_1$-$C_3$ alkylene)-. Yet even more particularly, each $R^5$ is independently halide or $C_1$-$C_3$ alkyl.

In another embodiment, the present teachings provide a compound of the formula I,

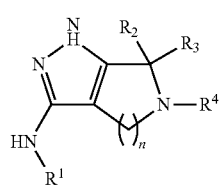

I wherein:
$R^1$ is chosen from —S(O)$R^a$, —S(O)$_2 R^a$, $C_1$-$C_{12}$ alkyl, $C_1$-$C_{12}$ alkyl substituted by at least one $R^f$, $C_3$-$C_{12}$ cycloalkyl, $C_3$-$C_{12}$ cycloalkyl substituted by at least one $R^f$, $C_2$-$C_{12}$ alkenyl, $C_2$-$C_{12}$ alkenyl substituted by at least one $R^f$, $C_2$-$C_{12}$ alkynyl, $C_2$-$C_{12}$ alkynyl substituted by at least one $R^f$, 3-10 membered heterocycle, 3-10 membered heterocycle substituted by at least one $R^f$, $C_1$-$C_6$ aralkyl, $C_1$-$C_6$ aralkyl substituted by at least one $R^f$, $C_1$-$C_6$ heteroaralkyl, $C_1$-$C_6$ heteroaralkyl substituted by at least one $R^f$, $C_6$-$C_{10}$ aryl, $C_6$-$C_{10}$ aryl substituted by at least one $R^5$, 5-10 membered heteroaryl, and 5-10 membered heteroaryl substituted by at least one $R^5$, wherein any two adjacent $R^5$ together with the atoms to which they are attached may form a fused 4-7 membered ring;

$R^2$ and $R^3$ are each independently chosen from —H, halide, —CN, —OH, —NO$_2$, —NH$_2$, $C_1$-$C_3$ perfluoroalkyl, $C_1$-$C_3$ alkoxy, $C_1$-$C_6$ alkoxyalkyl, unsubstituted $C_1$-$C_6$ aliphatic, $C_1$-$C_6$ alkylamine, $C_1$-$C_{12}$ alkyl, $C_1$-$C_{12}$ alkyl substituted by 1 or 2 groups selected from —OH, —NH$_2$ and —CN, $C_3$-$C_{12}$ cycloalkyl, $C_3$-$C_{12}$ cycloalkyl substituted by 1 or 2 groups selected from —OH, —NH$_2$ and —CN, $C_2$-$C_{12}$ alkenyl, $C_2$-$C_{12}$ alkenyl substituted by 1 or 2 groups selected from —OH, —NH$_2$ and —CN, $C_2$-$C_{12}$ alkynyl, and $C_2$-$C_{12}$ alkynyl substituted by 1 or 2 groups selected from —OH, —NH$_2$ and —CN;

$R^4$ is selected from $R^a$, —C(O)$R^a$, —C(O)NH$R^a$, —C(O)N$R^a R^b$, —C(O)S$R^a$, —S(O)$R^a$, and —S(O)$_2 R^a$;

$R^5$ is selected from $R^c$, —OH, halide, —CN, —C(O)$R^c$, —C(O)O$R^c$, —C(O)NH$R^c$, —C(O)N$R^c R^d$, —O$R^c$, —OC(O)$R^c$, —NO$_2$, —N$R^c R^d$, —N($R^c$)C(O)$R^d$, —NHC(O)$R^c$, —S$R^c$, —S(O)$R^c$, and —S(O)$_2 R^c$;

$R^a$, $R^b$, $R^c$, and $R^d$ are each independently selected from $C_1$-$C_{12}$ alkyl, $C_1$-$C_{12}$ alkyl substituted by at least one $R^f$, $C_3$-$C_{12}$ cycloalkyl, $C_3$-$C_{12}$ cycloalkyl substituted by at least one $R^f$, $C_2$-$C_{12}$ alkenyl, $C_2$-$C_{12}$ alkenyl substituted by at least one $R^f$, $C_2$-$C_{12}$ alkynyl, $C_2$-$C_{12}$ alkynyl substituted by at least one $R^f$, 3-10 membered heterocycle, 3-10 membered heterocycle substituted by at least one $R^f$, $C_6$-$C_{10}$ aryl, $C_6$-$C_{10}$ aryl substituted by at least one $R^f$, 5-10 membered heteroaryl, 5-10 membered heteroaryl substituted by at least one $R^f$, $C_1$-$C_6$ aralkyl, $C_1$-$C_6$ aralkyl substituted by at least one $R^f$, $C_1$-$C_6$ heteroaralkyl, $C_1$-$C_6$ heteroaralkyl substituted by at least one $R^f$, and $C_1$-$C_6$ perfluoroalkyl; or $R^a$ and $R^b$, together with the atom to which they are attached, form a 3 to 8 membered ring; or $R^c$ and $R^d$, together with the atom to which they are attached, form a 3 to 8 membered ring;

each $R^f$, which may be the same or different, is selected from halide, —OH, —CN, —C(O)$R^k$, —C(O)O$R^k$, —C(O)N$R^k R^j$, oxo, —O$R^k$, —OC(O)$R^k$, —NO$_2$, —N$R^k R^j$, —N($R^k$)C(O)$R^j$, —S$R^k$, —S(O)$R^k$, —S(O)$_2 R^k$, $C_1$-$C_{12}$ alkyl, $C_1$-$C_{12}$ alkyl substituted by at least one $R^m$, $C_3$-$C_{12}$ cycloalkyl, $C_3$-$C_{12}$ cycloalkyl substituted by at least one $R^m$, $C_2$-$C_{12}$ alkenyl, $C_2$-$C_{12}$ alkenyl substituted by at least one $R^m$, $C_2$-$C_{12}$ alkynyl, $C_2$-$C_{12}$ alkynyl substituted by at least one $R^m$, 3-10 membered heterocycle, 3-10 membered heterocycle substituted by 1 to 4 $R^m$, $C_6$-$C_{10}$ aryl, $C_6$-$C_{10}$ aryl substituted by 1 to 4 $R^m$, 5-10 membered heteroaryl, 5-10 membered heteroaryl substituted by 1 to 4 $R^m$, $C_1$-$C_3$ aralkyl, $C_1$-$C_3$ aralkyl substituted by 1 to 4 $R^m$, $C_1$-$C_3$ heteroaralkyl, $C_1$-$C_3$ heteroaralkyl substituted by 1 to 4 $R^m$, and $C_1$-$C_6$ perfluoroalkyl;

$R^k$ and $R^j$ are each independently selected from —H, —OH, $C_1$-$C_6$ aliphatic, and $C_1$-$C_3$ perfluoroalkyl; and $R^m$ is selected from halide, —OH, —CN, —C(O)$R^k$, —C(O)O$R^k$, —CON$R^k R^j$, oxo, —O$R^k$, —OC(O)$R^k$, —NO$_2$, —N$R^k R^j$, —N($R^k$)C(O)$R^k$, —S$R^k$, —S(O)$R^k$, —S(O)$_2 R^k$, and $C_1$-$C_3$ perfluoroalkyl;

n is 1, 2, or 3;

or a pharmaceutically acceptable salt, solvate or hydrate thereof.

In a particular aspect of this embodiment, n is 1.

In another embodiment, the present invention provides a compound of formula II,

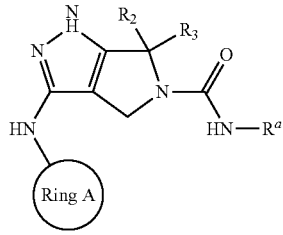

II wherein:

$R^2$ and $R^3$ are each independently chosen from —H, halide, —CN, —OH, —NO$_2$, —NH$_2$, $C_1$-$C_3$ perfluoroalkyl, $C_1$-$C_3$ alkoxy, $C_1$-$C_6$ alkoxyalkyl, unsubstituted $C_1$-$C_6$ aliphatic, $C_1$-$C_6$ alkylamine, $C_1$-$C_{12}$ alkyl, $C_1$-$C_{12}$ alkyl substituted by 1 or 2 groups selected from —OH, —NH$_2$ and —CN, $C_3$-$C_{12}$ cycloalkyl, $C_3$-$C_{12}$ cycloalkyl substituted by 1 or 2 groups selected from —OH, —NH$_2$ and —CN, $C_2$-$C_{12}$ alkenyl, $C_2$-$C_{12}$ alkenyl substituted by 1 or 2 groups selected from —OH, —NH$_2$ and —CN, $C_2$-$C_{12}$ alkynyl, and $C_2$-$C_{12}$ alkynyl substituted by 1 or 2 groups selected from —OH, —NH$_2$ and —CN;

Ring A is selected from $C_6$-$C_{10}$ aryl, $C_6$-$C_{10}$ aryl substituted by at least one $R^5$, 5-10 membered heteroaryl, and 5-10 membered heteroaryl substituted by at least one $R^5$, wherein any two adjacent $R^5$ together with the atoms to which they are attached may form a fused 4-7 membered ring;

$R^5$ is selected from $R^c$, —OH, halide, —CN, —C(O)$R^c$, —C(O)O$R^c$, —C(O)NH$R^c$, —C(O)N$R^c R^d$, —O$R^c$, —OC(O)$R^c$, —NO$_2$, —NH$R^c$, —N$R^c R^d$, —N($R^c$)C(O)$R^d$, —NHC(O)$R^c$, —S$R^c$, —S(O)$R^c$, and —S(O)$_2 R^c$;

$R^a$, $R^c$, and $R^d$ are each independently selected from $C_1$-$C_{12}$ alkyl, $C_1$-$C_{12}$ alkyl substituted by at least one $R^f$, $C_3$-$C_{12}$ cycloalkyl, $C_3$-$C_{12}$ cycloalkyl substituted by at least one $R^f$, $C_2$-$C_{12}$ alkenyl, $C_2$-$C_{12}$ alkenyl substituted by at least one $R^f$, $C_2$-$C_{12}$ alkynyl, $C_2$-$C_{12}$ alkynyl substituted by at least one $R^f$, 3-10 membered heterocycle, 3-10 membered heterocycle substituted by at least one $R^f$, $C_6$-$C_{10}$ aryl, $C_6$-$C_{10}$ aryl substituted by at least one $R^f$, 5-10 membered heteroaryl, 5-10 membered heteroaryl substituted by at least one $R^f$, $C_1$-$C_6$ aralkyl, $C_1$-$C_6$ aralkyl substituted by at least one $R^f$, $C_1$-$C_6$ heteroaralkyl, $C_1$-$C_6$ heteroaralkyl substituted by at least one $R^f$, and $C_1$-$C_6$ perfluoroalkyl; or $R^c$ and $R^d$, together with the atom to which they are attached, form a 3 to 8 membered ring;

each $R^f$, which may be the same or different, is selected from halide, —OH, —CN, —C(O)$R^k$, —C(O)O$R^k$, —C(O)N$R^k R^j$, oxo, —O$R^k$, —OC(O)$R^k$, —NO$_2$, —N$R^k R^j$, —N($R^k$)C(O)$R^j$, —S$R^k$, —S(O)$R^k$, —S(O)$_2 R^k$, $C_1$-$C_{12}$ alkyl, $C_1$-$C_{12}$ alkyl substituted by at least one $R^m$, $C_3$-$C_{12}$ cycloalkyl, $C_3$-$C_{12}$ cycloalkyl substituted by at least one $R^m$, $C_2$-$C_{12}$ alkenyl, $C_2$-$C_{12}$ alkenyl substituted by at least one $R^m$, $C_2$-$C_{12}$ alkynyl, $C_2$-$C_{12}$ alkynyl substituted by at least one $R^m$, 3-10 membered heterocycle, 3-10 membered heterocycle substituted by 1 to 4 $R^m$, $C_6$-$C_{10}$ aryl, $C_6$-$C_{10}$ aryl substituted by 1 to 4 $R^m$, 5-10 membered heteroaryl, 5-10 membered heteroaryl substituted by 1 to 4 $R^m$, $C_1$-$C_3$ aralkyl, $C_1$-$C_3$ aralkyl substituted by 1 to 4 $R^m$, $C_1$-$C_3$ heteroaralkyl, $C_1$-$C_3$ heteroaralkyl substituted by 1 to 4 $R^m$, and $C_1$-$C_6$ perfluoroalkyl;

$R^k$ and $R^j$ are each independently selected from —H, —OH, $C_1$-$C_6$ aliphatic, and $C_1$-$C_3$ perfluoroalkyl; and $R^m$ is selected from halide, —OH, —CN, —C(O)$R^k$, —C(O)O$R^k$, —CONR$^k R^j$, oxo, —O$R^k$, —OC(O)$R^k$, —NO$_2$, —N$R^k R^j$, —N($R^k$)C(O)$R^k$, —S$R^k$, —S(O)$R^k$, —S(O)$_2 R^k$, and $C_1$-$C_3$ perfluoroalkyl;

or a pharmaceutically acceptable salt, solvate or hydrate thereof.

In another embodiment, the present invention provides a compound of formula III,

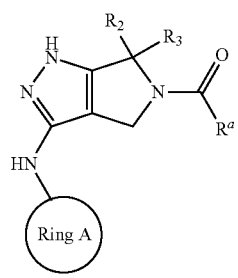

III wherein:

$R^2$ and $R^3$ are each independently chosen from —H, halide, —CN, —OH, —NO$_2$, —NH$_2$, $C_1$-$C_3$ perfluoroalkyl, $C_1$-$C_3$ alkoxy, $C_1$-$C_6$ alkoxyalkyl, unsubstituted $C_1$-$C_6$ aliphatic, $C_1$-$C_6$ alkylamine, $C_1$-$C_{12}$ alkyl, $C_1$-$C_{12}$ alkyl substituted by 1 or 2 groups selected from —OH, —NH$_2$ and —CN, $C_3$-$C_{12}$ cycloalkyl, $C_3$-$C_{12}$ cycloalkyl substituted by 1 or 2 groups selected from —OH, —NH$_2$ and —CN, $C_2$-$C_{12}$ alkenyl, $C_2$-$C_{12}$ alkenyl substituted by 1 or 2 groups selected from —OH, —NH$_2$ and —CN, $C_2$-$C_{12}$ alkynyl, and $C_2$-$C_{12}$ alkynyl substituted by 1 or 2 groups selected from —OH, —NH$_2$ and —CN;

Ring A is selected from $C_6$-$C_{10}$ aryl, $C_6$-$C_{10}$ aryl substituted by at least one $R^5$, 5-10 membered heteroaryl, and 5-10 membered heteroaryl substituted by at least one $R^5$, wherein any two adjacent $R^5$ together with the atoms to which they are attached may form a fused 4-7 membered ring;

$R^5$ is selected from $R^c$, —OH, halide, —CN, —C(O)$R^c$, —C(O)O$R^c$, —C(O)NH$R^c$, —C(O)N$R^c R^d$, —O$R^c$, —OC(O)$R^c$, —NO$_2$, —NH$R^c$, —N$R^c R^d$, —N($R^c$)C(O)$R^d$, —NHC(O)$R^c$, —S$R^c$, —S(O)$R^c$, and —S(O)$_2 R^c$;

$R^a$, $R^c$, and $R^d$ are each independently selected from $C_1$-$C_{12}$ alkyl, $C_1$-$C_{12}$ alkyl substituted by at least one $R^f$, $C_3$-$C_{12}$ cycloalkyl, $C_3$-$C_{12}$ cycloalkyl substituted by at least one $R^f$, $C_2$-$C_{12}$ alkenyl, $C_2$-$C_{12}$ alkenyl substituted by at least one $R^f$, $C_2$-$C_{12}$ alkynyl, $C_2$-$C_{12}$ alkynyl substituted by at least one $R^f$, 3-10 membered heterocycle, 3-10 membered heterocycle substituted by at least one $R^f$, $C_6$-$C_{10}$ aryl, $C_6$-$C_{10}$ aryl substituted by at least one $R^f$, 5-10 membered heteroaryl, 5-10 membered heteroaryl substituted by at least one $R^f$, $C_1$-$C_6$ aralkyl, $C_1$-$C_6$ aralkyl substituted by at least one $R^f$, $C_1$-$C_6$ heteroaralkyl, $C_1$-$C_6$ heteroaralkyl substituted by at least one $R^f$, and $C_1$-$C_6$ perfluoroalkyl; or $R^c$ and $R^d$, together with the atom to which they are attached, form a 3 to 8 membered ring;

each $R^f$, which may be the same or different, is selected from halide, —OH, —CN, —C(O)$R^k$, —C(O)O$R^k$, —C(O)N$R^k R^j$, oxo, —O$R^k$, —OC(O)$R^k$, —NO$_2$, —N$R^k R^j$, —N($R^k$)C(O)$R^j$, —S$R^k$, —S(O)$R^k$, —S(O)$_2 R^k$, $C_1$-$C_{12}$ alkyl, $C_1$-$C_{12}$ alkyl substituted by at least one $R^m$, $C_3$-$C_{12}$ cycloalkyl, $C_3$-$C_{12}$ cycloalkyl substituted by at least one $R^m$, $C_2$-$C_{12}$ alkenyl, $C_2$-$C_{12}$ alkenyl substituted by at least one $R^m$, $C_2$-$C_{12}$ alkynyl, $C_2$-$C_{12}$ alkynyl substituted by at least one $R^m$, 3-10 membered heterocycle, 3-10 membered heterocycle substituted by 1 to 4 $R^m$, $C_6$-$C_{10}$ aryl, $C_6$-$C_{10}$ aryl substituted by 1 to 4 $R^m$, 5-10 membered heteroaryl, 5-10 membered heteroaryl substituted by 1 to 4 $R^m$, $C_1$-$C_3$ aralkyl, $C_1$-$C_3$ aralkyl substituted by 1 to 4 $R^m$, $C_1$-$C_3$ heteroaralkyl, $C_1$-$C_3$ heteroaralkyl substituted by 1 to 4 $R^m$, and $C_1$-$C_6$ perfluoroalkyl;

$R^k$ and $R^j$ are each independently selected from —H, —OH, $C_1$-$C_6$ aliphatic, and $C_1$-$C_3$ perfluoroalkyl; and $R^m$ is selected from halide, —OH, —CN, —C(O)$R^k$, —C(O)O$R^k$, —CONR$^k$R$^j$, oxo, —O$R^k$, —OC(O)$R^k$, —NO$_2$, —N$R^k$R$^j$, —N($R^k$)C(O)$R^k$, —S$R^k$, —S(O)$R^k$, —S(O)$_2$R$^k$, and $C_1$-$C_3$ perfluoroalkyl;

or a pharmaceutically acceptable salt, solvate or hydrate thereof.

In another embodiment, the present invention provides a compound of formula IV,

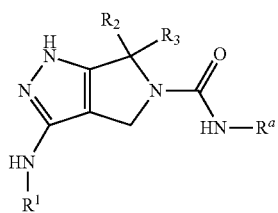

IV wherein:

$R^1$ is chosen from —S(O)$R^a$, —S(O)$_2$R$^a$, $C_1$-$C_{12}$ alkyl, $C_1$-$C_{12}$ alkyl substituted by at least one $R^f$, $C_3$-$C_{12}$ cycloalkyl, $C_3$-$C_{12}$ cycloalkyl substituted by at least one $R^f$, $C_2$-$C_{12}$ alkenyl, $C_2$-$C_{12}$ alkenyl substituted by at least one $R^f$, $C_2$-$C_{12}$ alkynyl, $C_2$-$C_{12}$ alkynyl substituted by at least one $R^f$, 3-10 membered heterocycle, 3-10 membered heterocycle substituted by at least one $R^f$, $C_1$-$C_6$ aralkyl, $C_1$-$C_6$ aralkyl substituted by at least one $R^f$, $C_1$-$C_6$ heteroaralkyl, $C_1$-$C_6$ heteroaralkyl substituted by at least one $R^f$, $C_6$-$C_{10}$ aryl, $C_6$-$C_{10}$ aryl substituted by at least one $R^5$, 5-10 membered heteroaryl, and 5-10 membered heteroaryl substituted by at least one $R^5$, wherein any two adjacent $R^5$ together with the atoms to which they are attached may form a fused 4-7 membered ring;

$R^2$ and $R^3$ are each independently chosen from —H, halide, —CN, —OH, —NO$_2$, —NH$_2$, $C_1$-$C_3$ perfluoroalkyl, $C_1$-$C_3$ alkoxy, $C_1$-$C_6$ alkoxyalkyl, unsubstituted $C_1$-$C_6$ aliphatic, $C_1$-$C_6$ alkylamine, $C_1$-$C_{12}$ alkyl, $C_1$-$C_{12}$ alkyl substituted by 1 or 2 groups selected from —OH, —NH$_2$ and —CN, $C_3$-$C_{12}$ cycloalkyl, $C_3$-$C_{12}$ cycloalkyl substituted by 1 or 2 groups selected from —OH, —NH$_2$ and —CN, $C_2$-$C_{12}$ alkenyl, $C_2$-$C_{12}$ alkenyl substituted by 1 or 2 groups selected from —OH, —NH$_2$ and —CN, $C_2$-$C_{12}$ alkynyl, and $C_2$-$C_{12}$ alkynyl substituted by 1 or 2 groups selected from —OH, —NH$_2$ and —CN;

$R^5$ is selected from $R^c$, —OH, halide, —CN, —C(O)$R^c$, —C(O)O$R^c$, —C(O)NH$R^c$, —C(O)N$R^c$R$^d$, —O$R^c$, —OC(O)$R^c$, —NO$_2$, —NH$R^c$, N$R^c$R$^d$, —N($R^c$)C(O)$R^d$, —NHC(O)$R^c$, —S$R^c$, —S(O)$R^c$, and —S(O)$_2$R$^c$;

$R^a$, $R^c$, and $R^d$ are each independently selected from $C_1$-$C_{12}$ alkyl, $C_1$-$C_{12}$ alkyl substituted by at least one $R^f$, $C_3$-$C_{12}$ cycloalkyl, $C_3$-$C_{12}$ cycloalkyl substituted by at least one $R^f$, $C_2$-$C_{12}$ alkenyl, $C_2$-$C_{12}$ alkenyl substituted by at least one $R^f$, $C_2$-$C_{12}$ alkynyl, $C_2$-$C_{12}$ alkynyl substituted by at least one $R^f$, 3-10 membered heterocycle, 3-10 membered heterocycle substituted by at least one $R^f$, $C_6$-$C_{10}$ aryl, $C_6$-$C_{10}$ aryl substituted by at least one $R^f$, 5-10 membered heteroaryl, 5-10 membered heteroaryl substituted by at least one $R^f$, $C_1$-$C_6$ aralkyl, $C_1$-$C_6$ aralkyl substituted by at least one $R^f$, $C_1$-$C_6$ heteroaralkyl, $C_1$-$C_6$ heteroaralkyl substituted by at least one $R^f$, and $C_1$-$C_6$ perfluoroalkyl; or $R^c$ and $R^d$, together with the atom to which they are attached, form a 3 to 8 membered ring;

each $R^f$, which may be the same or different, is selected from halide, —OH, —CN, —C(O)$R^k$, —C(O)O$R^k$, —C(O)NR$^k$R$^j$, oxo, —O$R^k$, —OC(O)$R^k$, —NO$_2$, —N$R^k$R$^j$, —N($R^k$)C(O)$R^j$, —S$R^k$, —S(O)$R^k$, —S(O)$_2$R$^k$, $C_1$-$C_{12}$ alkyl, $C_1$-$C_{12}$ alkyl substituted by at least one $R^m$, $C_3$-$C_{12}$ cycloalkyl, $C_3$-$C_{12}$ cycloalkyl substituted by at least one $R^m$, $C_2$-$C_{12}$ alkenyl, $C_2$-$C_{12}$ alkenyl substituted by at least one $R^m$, $C_2$-$C_{12}$ alkynyl, $C_2$-$C_{12}$ alkynyl substituted by at least one $R^m$, 3-10 membered heterocycle, 3-10 membered heterocycle substituted by 1 to 4 $R^m$, $C_6$-$C_{10}$ aryl, $C_6$-$C_{10}$ aryl substituted by 1 to 4 $R^m$, 5-10 membered heteroaryl, 5-10 membered heteroaryl substituted by 1 to 4 $R^m$, $C_1$-$C_3$ aralkyl, $C_1$-$C_3$ aralkyl substituted by 1 to 4 $R^m$, $C_1$-$C_3$ heteroaralkyl, $C_1$-$C_3$ heteroaralkyl substituted by 1 to 4 $R^m$, and $C_1$-$C_6$ perfluoroalkyl;

$R^k$ and $R^j$ are each independently selected from —H, —OH, $C_1$-$C_6$ aliphatic, and $C_1$-$C_3$ perfluoroalkyl;

$R^m$ is selected from halide, —OH, —CN, —C(O)$R^k$, —C(O)O$R^k$, —CONR$^k$R$^j$, oxo, —O$R^k$, —OC(O)$R^k$, —NO$_2$, —N$R^k$R$^j$, —N($R^k$)C(O)$R^k$, —S$R^k$, —S(O)$R^k$, —S(O)$_2$R$^k$, and $C_1$-$C_3$ perfluoroalkyl; and when the atoms of any two adjacent $R^5$ groups that are attached directly to $R^1$ are chosen from carbon, nitrogen, oxygen and sulfur, then said adjacent $R^5$ groups may form a fused 4-7 membered ring;

or a pharmaceutically acceptable salt, solvate or hydrate thereof.

In another embodiment, the present invention provides a compound of formula V,

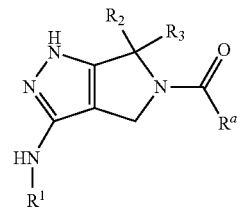

V wherein:

$R^1$ is chosen from —S(O)$R^a$, —S(O)$_2$R$^a$, $C_1$-$C_{12}$ alkyl, $C_1$-$C_{12}$ alkyl substituted by at least one $R^f$, $C_3$-$C_{12}$ cycloalkyl, $C_3$-$C_{12}$ cycloalkyl substituted by at least one $R^f$, $C_2$-$C_{12}$ alkenyl, $C_2$-$C_{12}$ alkenyl substituted by at least one $R^f$, $C_2$-$C_{12}$ alkynyl, $C_2$-$C_{12}$ alkynyl substituted by at least one $R^f$, 3-10 membered heterocycle, 3-10 membered heterocycle substituted by at least one $R^f$, $C_1$-$C_6$ aralkyl, $C_1$-$C_6$ aralkyl substituted by at least one $R^f$, $C_1$-$C_6$ heteroaralkyl, $C_1$-$C_6$ heteroaralkyl substituted by at least one $R^f$, $C_6$-$C_{10}$ aryl, $C_6$-$C_{10}$ aryl substituted by at least one $R^5$, 5-10 membered heteroaryl, and 5-10 membered heteroaryl substituted by at least one $R^5$, wherein any two adjacent $R^5$ together with the atoms to which they are attached may form a fused 4-7 membered ring;

$R^2$ and $R^3$ are each independently chosen from —H, halide, —CN, —OH, —NO$_2$, —NH$_2$, $C_1$-$C_3$ perfluoroalkyl, $C_1$-$C_3$ alkoxy, $C_1$-$C_6$ alkoxyalkyl, unsubstituted $C_1$-$C_6$ aliphatic, $C_1$-$C_6$ alkylamine, $C_1$-$C_{12}$ alkyl, $C_1$-$C_{12}$ alkyl substituted by 1 or 2 groups selected from —OH, —NH$_2$ and —CN, $C_3$-$C_{12}$ cycloalkyl, $C_3$-$C_{12}$ cycloalkyl substituted by 1 or 2 groups selected from —OH, —NH$_2$ and —CN, $C_2$-$C_{12}$ alkenyl, $C_2$-$C_{12}$ alkenyl substituted by 1 or 2 groups selected from —OH, —NH$_2$ and —CN, C$_2$-C$_{12}$ alkynyl, and C$_2$-C$_{12}$ alkynyl substituted by 1 or 2 groups selected from —OH, —NH$_2$ and —CN;

R$^5$ is selected from R$^c$, —OH, halide, —CN, —C(O)R$^c$, —C(O)OR$^c$, —C(O)NHR$^c$, —C(O)NR$^c$R$^d$, —OR$^c$, —OC(O)R$^c$, —NO$_2$, —NR$^c$R$^d$, —N(R$^c$)C(O)R$^d$, —NHC(O)R$^c$, —SR$^c$, —S(O)R$^c$, and —S(O)$_2$R$^c$;

R$^a$, R$^c$, and R$^d$ are each independently selected from C$_1$-C$_{12}$ alkyl, C$_1$-C$_{12}$ alkyl substituted by at least one R$^f$, C$_3$-C$_{12}$ cycloalkyl, C$_3$-C$_{12}$ cycloalkyl substituted by at least one R$^f$, C$_2$-C$_{12}$ alkenyl, C$_2$-C$_{12}$ alkenyl substituted by at least one R$^f$, C$_2$-C$_{12}$ alkynyl, C$_2$-C$_{12}$ alkynyl substituted by at least one R$^f$, 3-10 membered heterocycle, 3-10 membered heterocycle substituted by at least one R$^f$, C$_6$-C$_{10}$ aryl, C$_6$-C$_{10}$ aryl substituted by at least one R$^f$, 5-10 membered heteroaryl, 5-10 membered heteroaryl substituted by at least one R$^f$, C$_1$-C$_6$ aralkyl, C$_1$-C$_6$ aralkyl substituted by at least one R$^f$, C$_1$-C$_6$ heteroaralkyl, C$_1$-C$_6$ heteroaralkyl substituted by at least one R$^f$, and C$_1$-C$_6$ perfluoroalkyl; or R$^c$ and R$^d$, together with the atom to which they are attached, form a 3 to 8 membered ring;

each R$^f$, which may be the same or different, is selected from halide, —OH, —CN, —C(O)R$^k$, —C(O)OR$^k$, —C(O)NR$^k$R$^j$, oxo, —OR$^k$, —OC(O)R$^k$, —NO$_2$, —NR$^k$R$^j$, —N(R$^k$)C(O)R$^j$, —SR$^k$, —S(O)R$^k$, —S(O)$_2$R$^k$, C$_1$-C$_{12}$ alkyl, C$_1$-C$_{12}$ alkyl substituted by at least one R$^m$, C$_3$-C$_{12}$ cycloalkyl, C$_3$-C$_{12}$ cycloalkyl substituted by at least one R$^m$, C$_2$-C$_{12}$ alkenyl, C$_2$-C$_{12}$ alkenyl substituted by at least one R$^m$, C$_2$-C$_{12}$ alkynyl, C$_2$-C$_{12}$ alkynyl substituted by at least one R$^m$, 3-10 membered heterocycle, 3-10 membered heterocycle substituted by 1 to 4 R$^m$, C$_6$-C$_{10}$ aryl, C$_6$-C$_{10}$ aryl substituted by 1 to 4 R$^m$, 5-10 membered heteroaryl, 5-10 membered heteroaryl substituted by 1 to 4 R$^m$, C$_1$-C$_3$ aralkyl, C$_1$-C$_3$ aralkyl substituted by 1 to 4 R$^m$, C$_1$-C$_3$ heteroaralkyl, C$_1$-C$_3$ heteroaralkyl substituted by 1 to 4 R$^m$, and C$_1$-C$_6$ perfluoroalkyl;

R$^k$ and R$^j$ are each independently selected from —H, —OH, C$_1$-C$_6$ aliphatic, and C$_1$-C$_3$ perfluoroalkyl;

R$^m$ is selected from halide, —OH, —CN, —C(O)R$^k$, —C(O)OR$^k$, —CONR$^k$R$^j$, oxo, —OR$^k$, —OC(O)R$^k$, —NO$_2$, —NR$^k$R$^j$, —N(R$^k$)C(O)R$^k$, —SR$^k$, —S(O)R$^k$, —S(O)$_2$R$^k$, and C$_1$-C$_3$ perfluoroalkyl; and when the atoms of any two adjacent R$^5$ groups that are attached directly to R$^1$ are chosen from carbon, nitrogen, oxygen and sulfur, then said adjacent R$^5$ groups may form a fused 4-7 membered ring;

or a pharmaceutically acceptable salt, solvate or hydrate thereof.

In some embodiments, R$^2$ and R$^3$ are —CH$_3$. In some embodiments, R$^4$ is selected from —COR$^a$, —C(O)NHR$^a$, and —C(O)NR$^a$R$^b$; and R$^a$ is selected from C$_1$-C$_{12}$ alkyl, C$_1$-C$_{12}$ alkyl substituted by at least one R$^f$, C$_3$-C$_{12}$ cycloalkyl, C$_3$-C$_{12}$ cycloalkyl substituted by at least one R$^f$, C$_2$-C$_{12}$ alkenyl, C$_2$-C$_{12}$ alkenyl substituted by at least one R$^f$, C$_2$-C$_{12}$ alkynyl, and C$_2$-C$_{12}$ alkynyl substituted by at least one R$^f$. In some embodiments, R$^a$ is selected from cycloalkyl, and cycloalkyl substituted by at least one R$^f$. In some embodiments, R$^a$ is selected from cyclopropyl, and cyclopropyl substituted by at least one R$^f$. In some embodiments, R$^a$ is selected from cyclopropyl, and trans-2-phenylcyclopropyl. In some embodiments, R$^a$ is selected from ethyl and ethyl substituted by at least one R$^f$. In some embodiments, R$^a$ is

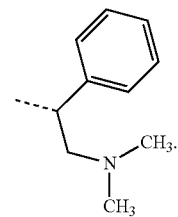

In some embodiments, R$^a$ is

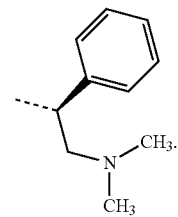

In some embodiments, R$^a$ is selected from ethyl and ethyl substituted by at least one R$^f$. In some embodiments, R$^a$ is

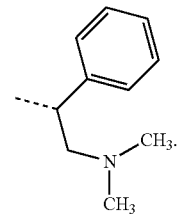

In some embodiments, R$^a$ is

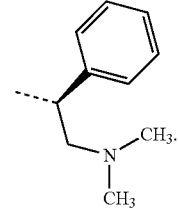

In some embodiments, R$^4$ is

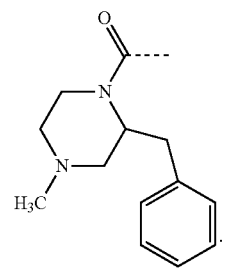

In some embodiments, $R^4$ is

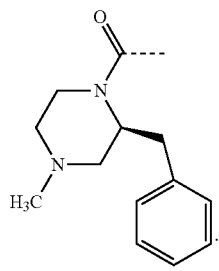

In some embodiments, $R^1$ is selected from 5-10 membered heteroaryl, and 5-10 membered heteroaryl substituted by at least one $R^5$. In some embodiments, Ring A is 5-10 membered heteroaryl. In some embodiments, Ring A is 5-10 membered heteroaryl substituted by at least one $R^5$.

In some embodiments, the 5-10 membered heteroaryl is selected from pyrrole, furan, thiophene, oxazole, thiazole, pryazole, pyridine, pyrimidine, quinoline, isoquinoline, purine, tetrazole, triazine, and carbazole.

In some embodiments, the 5-10 membered heteroaryl substituted by at least one $R^5$ is selected from

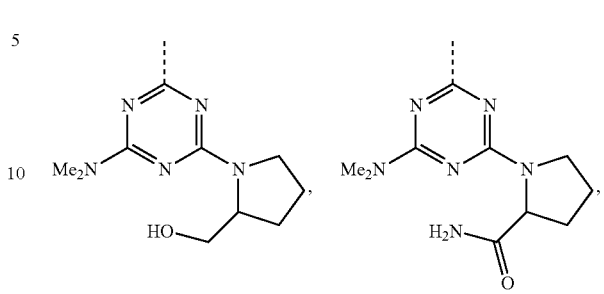

In some embodiments, the 5-10 membered heteroaryl substituted by at least one $R^5$ is selected from

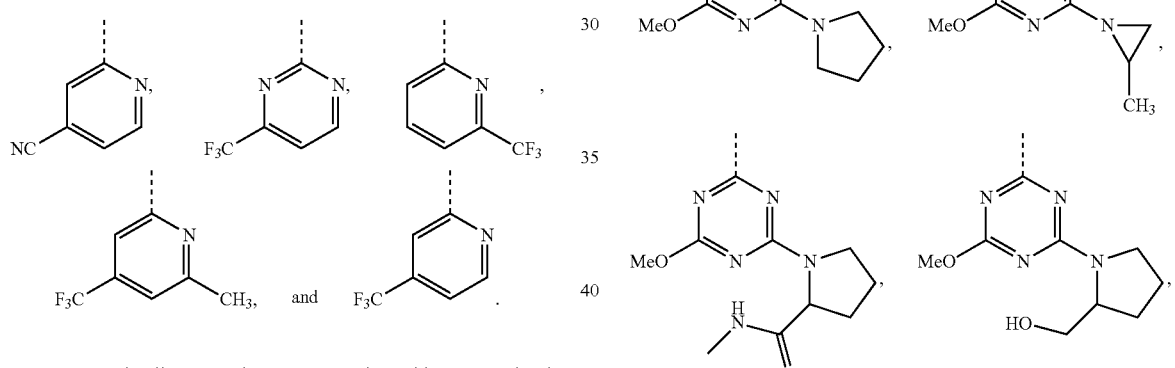

In some embodiments, the 5-10 membered heteroaryl substituted by at least one $R^5$ is selected from

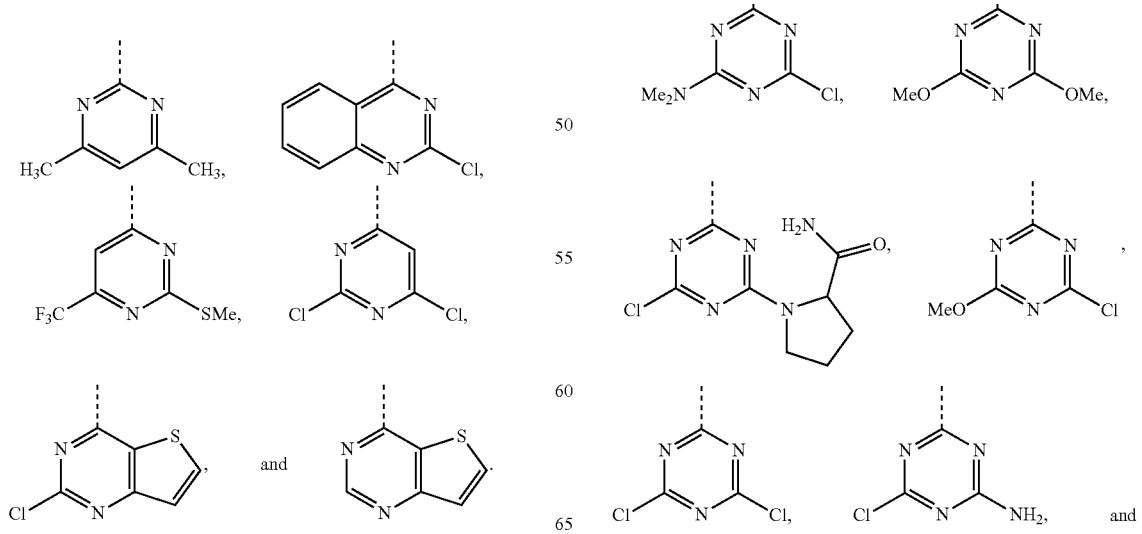

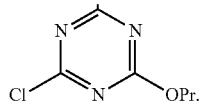

In some embodiments, the 5-10 membered heteroaryl substituted by at least one R⁵ is selected from

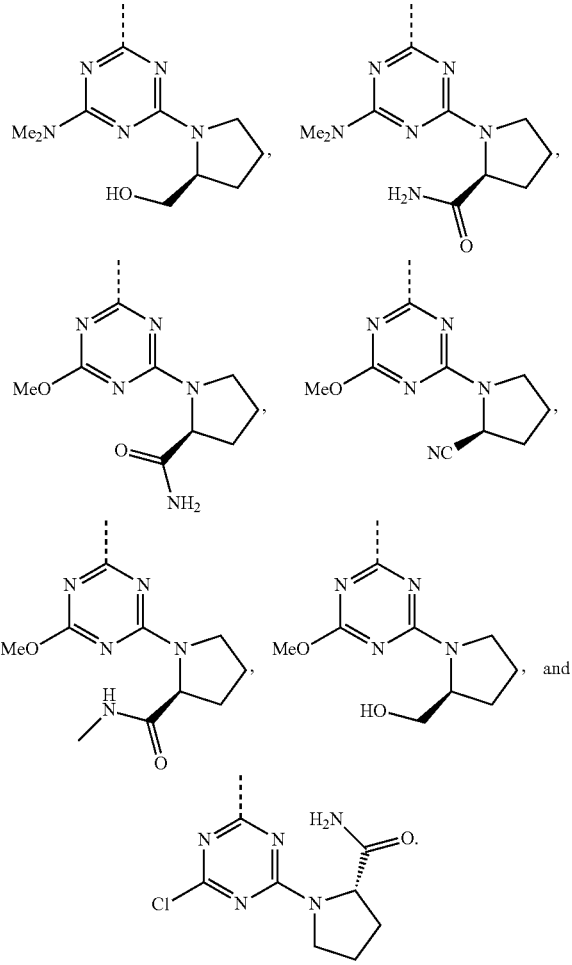

In another embodiment, the current invention provides a compound of formula VI,

VI

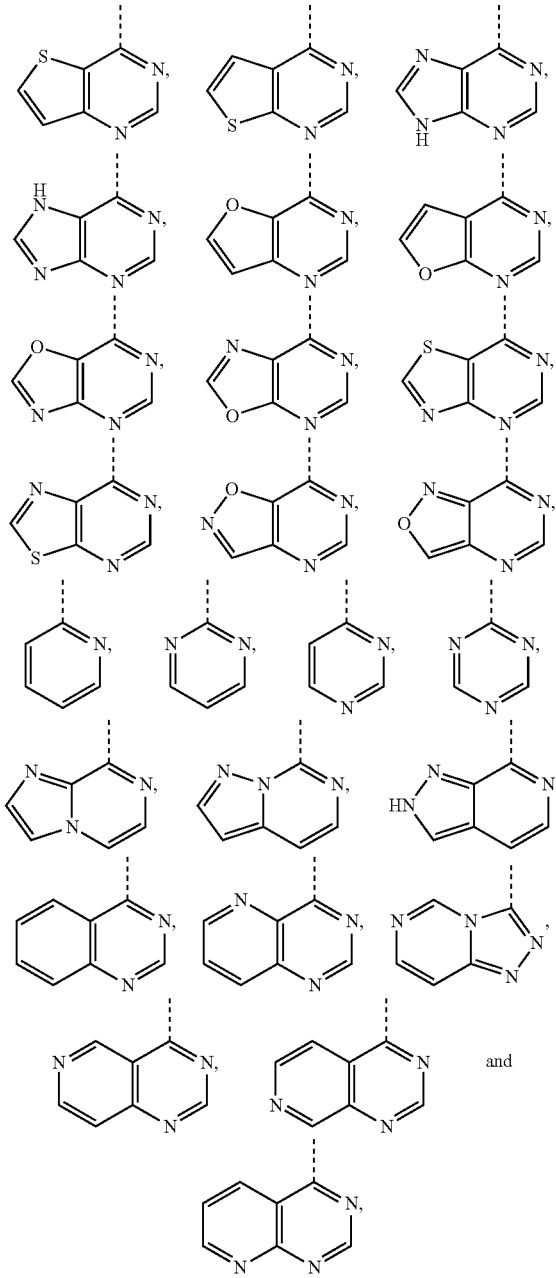

wherein:

B is a bond, —CHR$^t$—, —O— or —NH—, wherein R$^t$ is H or $C_1$-$C_3$ alkyl;

R¹ is selected from and
R¹ is optionally further substituted by 1-5 R⁵;
R² is unsubstituted $C_1$-$C_3$ alkyl, R₃ is unsubstituted $C_1$-$C_3$ alkyl, or R² and R³ forms a ring selected from unsubstituted cyclopropyl and unsubstituted cyclobutyl;
each R⁵ is independently R$^x$;
each R$^x$ is independently -(L¹)$_m$-($C_1$-$C_6$ perfluoalkyl), $C_1$-$C_6$ alkyl, $C_2$-$C_6$ alkenyl, $C_2$-$C_6$ alkynyl, —($C_1$-$C_3$ alkylene)$_m$-($C_3$-$C_4$ cycloalkyl), —($C_1$-$C_3$ alkylene)$_m$-(3-4 member heterocyclyl) optionally substituted by 1-2 $C_1$-$C_3$ alkyl, -(L¹)$_m$-halide, -(L¹)$_m$-CN, -(L¹)$_m$-C(O)R$^k$, -(L¹)$_m$-C(O)OR$^k$, -(L¹)$_m$-C(O)NR$^k$R$^j$, -(L¹)$_m$-C(O)SR$^j$, -(L¹)$_m$-OR$^k$, -(L¹)$_m$-OC(O)R$^k$, -(L¹)$_m$-OC(O)NR$^j$R$^k$, -(L¹)$_m$-NO₂, -(L¹)$_m$-NR$^k$R$^j$, -(L¹)$_m$-N(R$^k$)C(O)R$^j$, -(L¹)$_m$-N(R$^k$)C(O)OR$^j$, -(L¹)$_m$-O-L¹-

$NR^kR^j$, $-(L^1)_m-O-L^1-OR^k$, $-(L^1)_m-NR^j-L^1-OR^k$, $-(L^1)_m-SR^k$, $-(L^1)_m-S(O)R^k$, $-(L^1)_m-S(O)OR^k$, $-(L^1)_m-S(O)NR^jR^k$, $-(L^1)_m-S(O)_2R^k$, $-(L^1)_m-S(O)_2OR^k$ or $-(L^1)_m-S(O)_2NR^jR^k$, wherein each $R^j$ and $R^k$ is independently H, OH, $C_1-C_3$ alkyl or $C_1-C_3$ perfluoroalkyl, or $R^j$ and $R^k$ on the same nitrogen forms a 3-4 member ring selected from aziridinyl and azetidinyl; $L^1$ is a bivalent radical selected from —($C_1-C_3$ alkylene)-, —($C_3-C_4$ cycloalkylene)-, -(3-4 member heterocyclylene)-, —($C_1-C_3$ alkylene)-($C_3-C_4$ cycloalkylene)-, —($C_3-C_4$ cycloalkylene)-($C_1-C_3$ alkylene)-, —($C_1-C_3$ alkylene)-(3-4 member heterocyclylene)- and -(3-4 member heterocyclylene)-($C_1-C_3$alkylene)-;

$R^a$ is selected from —($C_3-C_7$ cycloalkylene)-phenyl, —($C_3-C_7$ cycloalkylene)-(5-12 member heteroaryl), —($C_3-C_7$ cycloalkylene)-(3-12 member heterocyclyl) and —($C_3-C_7$ cycloalkyene)-($C_3-C_{12}$ cycloalkyl), $R^a$ is optionally further substituted by 1-6 groups selected from oxo and $R^x$; and each m is independently 0 or 1;

or a pharmaceutically acceptable salt, solvate or hydrate thereof.

In one particular aspect of this embodiment, and in combination of any other particular aspect not inconsistent, B is —O—, $R^2$ is unsubstituted methyl, $R^3$ is unsubstituted methyl. More particularly, $R^1$ is selected from

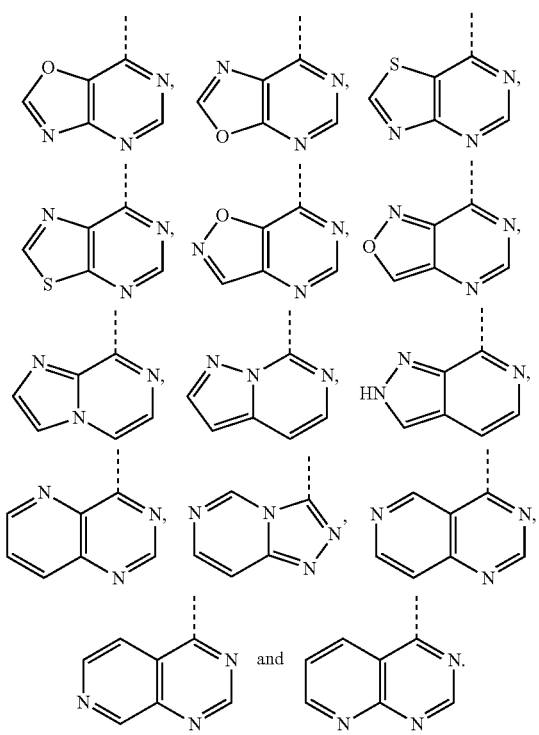

Also more particularly, $R^1$ is selected from

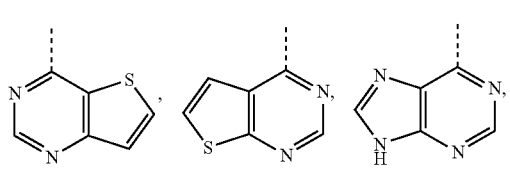

In another particular aspect of the embodiment, and in combination of any other particular aspect not inconsistent, B is —NH—, $R^2$ is unsubstituted methyl, $R^3$ is unsubstituted methyl. More particularly, $R^1$ is selected from

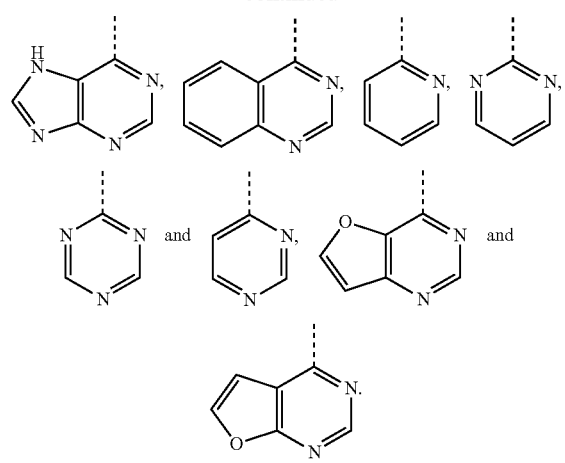

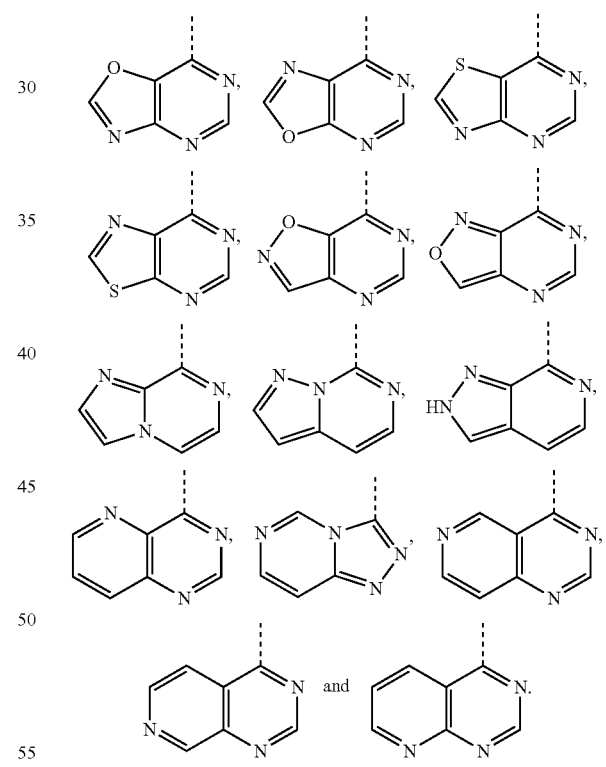

Also more particularly, $R^1$ is selected from

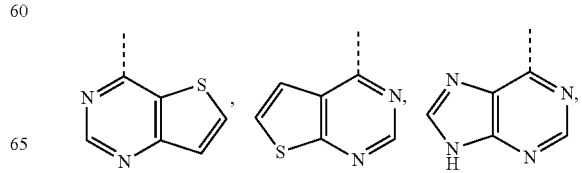

-continued

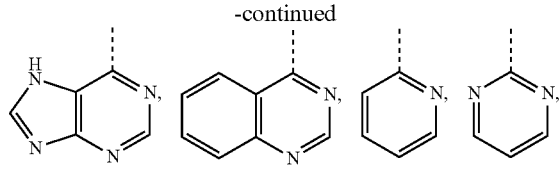

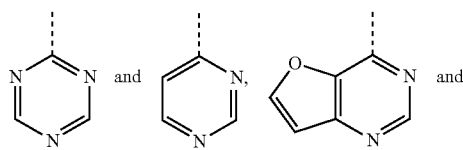

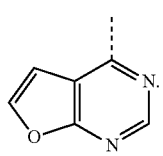

wherein the stereochemistry indicated herein represents that the two substituents of the cyclopropylene group are trans, $R^a$ is optionally further substituted by 1-6 groups selected from oxo and $R^x$. Even more particularly, the stereochemistry indicated herein represents the absolute stereochemistry at the carbon centers of the cyclopropylene group.

In yet another embodiment, the current invention provides a compound of formula VII,

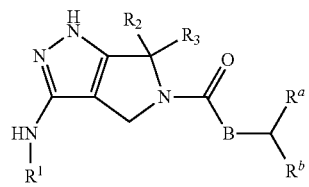

VII wherein:

B is a bond, —CHR$^t$—, —O— or —NH—, wherein R$^t$ is H or $C_1$-$C_3$ alkyl;

$R^1$ is selected from

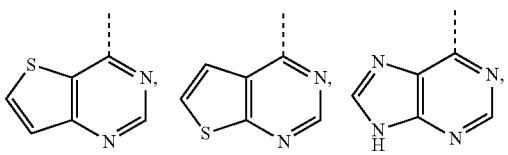

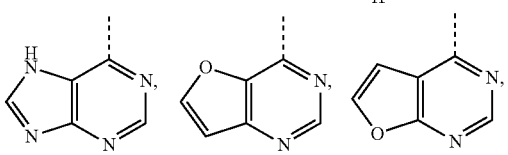

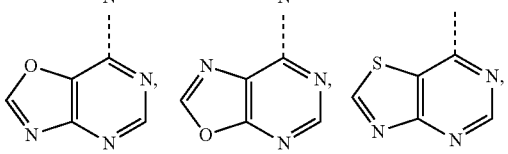

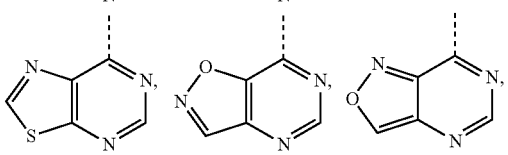

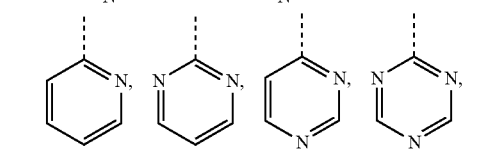

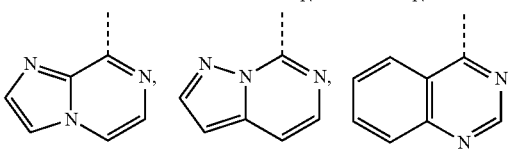

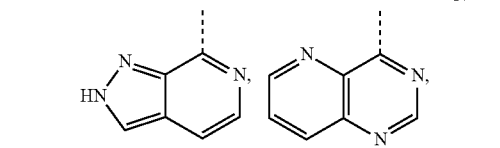

In another particular aspect of the embodiment, and in combination of any other particular aspect not inconsistent, $R^a$ is selected from -cyclopropylene-phenyl, -cyclopropylene-(5-12 member heteroaryl) and -cyclopropylene-(3-12 member heterocyclyl), $R^a$ is optionally further substituted by 1-6 groups selected from oxo and $R^x$. More particularly, $R^a$ is selected from

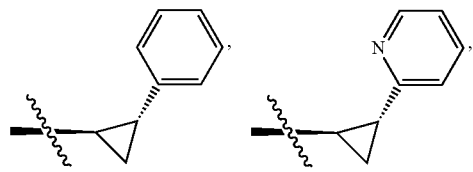

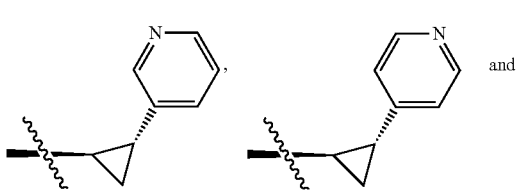

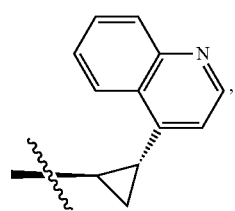

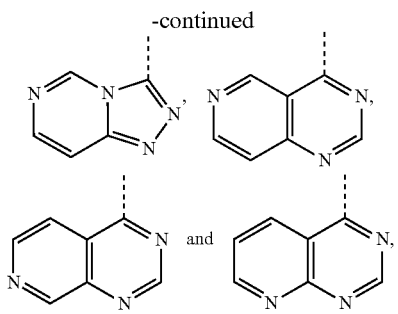

and

R$^1$ is optionally further substituted by 1-5 R$^5$;

R$^2$ is unsubstituted C$_1$-C$_3$ alkyl, R$_3$ is unsubstituted C$_1$-C$_3$ alkyl, or R$^2$ and R$^3$ form a ring selected from unsubstituted cyclopropyl and unsubstituted cyclobutyl;

R$^a$ is selected from -(L$^2$)$_m$-phenyl, -(L$^2$)$_m$-(5-12 member heteroaryl), -(L$^2$)$_m$-(C$_3$-C$_{12}$ cycloalkyl), and -(L$^2$)$_m$-(3-12 member heterocyclyl), wherein L$^2$ is a bivalent radical selected from —(C$_1$-C$_3$ alkylene)-, —(C$_3$-C$_4$ cycloalkylene)-, —(C$_1$-C$_3$ alkylene)-(C$_3$-C$_4$ cycloalkylene)-, —(C$_3$-C$_4$ cycloalkylene)-(C$_1$-C$_3$ alkylene)-, —O—, —(C$_1$-C$_3$ alkylene)-O— and —O—(C$_1$-C$_3$ alkylene)-, and R$^a$ is optionally further substituted by 1-6 groups selected from oxo and R$^x$;

R$^b$ is —(C$_1$-C$_6$ alkylene)$_m$-NR$^p$R$^q$, wherein each R$^p$ and R$^q$ is independently H, C$_1$-C$_3$ alkyl, or R$^p$ and R$^q$ forms a 3-7 member heterocyclyl containing 1-2 heteroatoms selected from O and N, the said 3-7 member heterocyclyl is optionally further substituted by 1-3 groups selected from halide and C$_1$-C$_3$ alkyl;

each R$^5$ is independently R$^x$;

each R$^x$ is independently -(L$^1$)$_m$-(C$_1$-C$_6$ perfluoalkyl), C$_1$-C$_6$ alkyl, C$_2$-C$_6$ alkenyl, C$_2$-C$_6$ alkynyl, —(C$_1$-C$_3$ alkylene)$_m$-(C$_3$-C$_4$ cycloalkyl), —(C$_1$-C$_3$ alkylene)$_m$-(3-4 member heterocyclyl) optionally substituted by 1-2 C$_1$-C$_3$ alkyl, -(L$^1$)$_m$-halide, -(L$^1$)$_m$-CN, -(L$^1$)$_m$-C(O)R$^k$, -(L$^1$)$_m$-C(O)OR$^k$, -(L$^1$)$_m$-C(O)NR$^k$R$^j$, -(L$^1$)$_m$-C(O)SR$^j$, -(L$^1$)$_m$-OR$^k$, -(L$^1$)$_m$-OC(O)R$^k$, -(L$^1$)$_m$-OC(O)NR$^j$R$^k$, -(L$^1$)$_m$-NO$_2$, -(L$^1$)$_m$-NR$^k$R$^j$, -(L$^1$)$_m$-N(R$^k$)C(O)R$^j$, -(L$^1$)$_m$-N(R$^k$)C(O)OR$^j$, -(L$^1$)$_m$-O-L$^1$-NR$^k$R$^j$, -(L$^1$)$_m$-O-L$^1$-OR$^k$, -(L$^1$)$_m$-NR$^j$-L$^1$-OR$^k$, -(L$^1$)$_m$-SR$^k$, -(L$^1$)$_m$-S(O)R$^k$, -(L$^1$)$_m$-S(O)OR$^k$, -(L$^1$)$_m$-S(O)NR$^j$R$^k$, -(L$^1$)$_m$-S(O)$_2$R$^k$, -(L$^1$)$_m$-S(O)$_2$OR$^k$ or -(L$^1$)$_m$-S(O)$_2$NR$^j$R$^k$, wherein each R$^j$ and R$^k$ is independently H, OH, C$_1$-C$_3$ alkyl or C$_1$-C$_3$ perfluoroalkyl, or R$^j$ and R$^k$ on the same nitrogen forms a 3-4 member ring selected from aziridinyl and azetidinyl; L$^1$ is a bivalent radical selected from —(C$_1$-C$_3$ alkylene)-, —(C$_3$-C$_4$ cycloalkylene)-, -(3-4 member heterocyclylene)-, —(C$_1$-C$_3$ alkylene)-(C$_3$-C$_4$ cycloalkylene)-, —(C$_3$-C$_4$ cycloalkylene)-(C$_1$-C$_3$ alkylene)-, —(C$_1$-C$_3$ alkylene)-(3-4 member heterocyclylene)- and -(3-4 member heterocyclylene)-(C$_1$-C$_3$alkylene)-; and each m is independently 0 or 1;

or a pharmaceutically acceptable salt thereof.

In one particular aspect of the embodiment, and in combination of any other particular aspect not inconsistent, B, R$^a$, R$^b$ and the carbon that connects them form a S chiral center at the carbon. More particularly, the compound is no less than 90% enantiomerically pure regarding the S chiral center.

In another particular aspect of the embodiment, and in combination of any other particular aspect not inconsistent, B is —O—, R$^2$ is unsubstituted methyl, R$^3$ is unsubstituted methyl. More particularly, R$^1$ is selected from

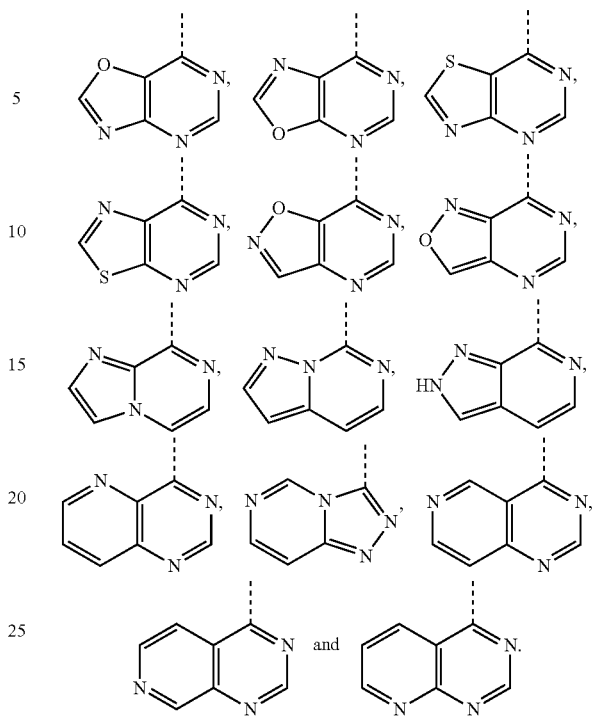

Also more particularly, R$^1$ is selected from

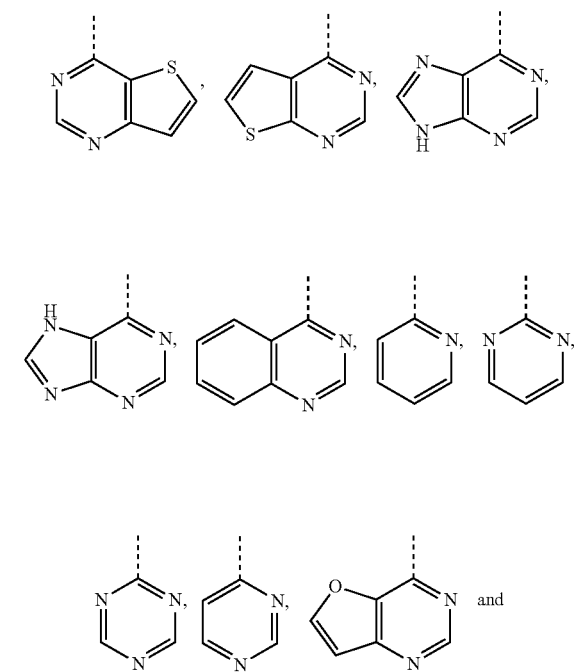

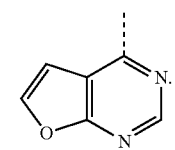

In another particular aspect of the embodiment, and in combination of any other particular aspect not inconsistent, B is —NH—, $R^2$ is unsubstituted methyl, $R^3$ is unsubstituted methyl. More particularly, $R^1$ is selected from

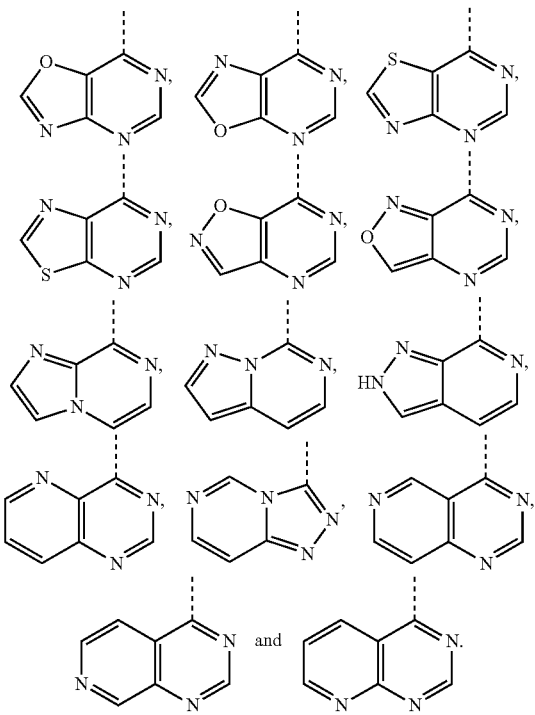

Also more particularly, $R^1$ is selected from

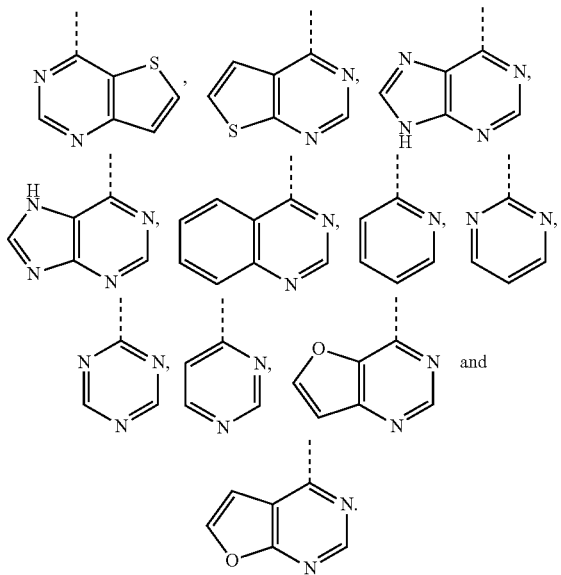

In another particular aspect of the embodiment, and in combination of any other particular aspect not inconsistent, $R^b$ is selected from —CH$_2$—N(CH$_3$)CH$_3$, —CH$_2$NHCH$_3$, —CH$_2$NH$_2$ and pyrrolyl.

In another particular aspect of the embodiment, and in combination of any other particular aspect not inconsistent, $R^a$ is selected from phenyl, 5-12 member heteroaryl, 3-12 member heterocyclyl and 3-12 member cycloalkyl, $R^a$ is optionally further substituted by 1-6 groups selected from oxo and $R^x$.

In yet another embodiment, the current invention provides a pharmaceutical composition comprising a compound of the invention.

In yet another embodiment, the current invention provides a pharmaceutical composition comprising a compound of the invention and a pharmaceutically acceptable carrier.

In yet another embodiment, the current invention provides a method of treating a mammalian disease condition mediated by protein kinase activity, comprising administering to a mammal a therapeutically acceptable amount of a compound, salt, hydrate or solvate of the invention. In one aspect of this embodiment, mammalian disease condition is tumor growth or abnormal cell proliferation.

In yet another embodiment, the current invention provides a method of modulating the activity of a protein kinase, comprising contacting the protein kinase with an effective amount of a compound, or pharmaceutically acceptable salt, solvate of any of the invention. In one aspect of this embodiment, the protein kinase is a PAK4 protein kinase.

In some embodiments, the present teachings provide pharmaceutical compositions comprising any of the compounds described herein and a pharmaceutically acceptable carrier. Examples of such compositions are described below.

In some embodiments, the present teachings provide a method of treating abnormal cell growth in a mammal, including a human, the method comprising administering to the mammal any of compound or pharmaceutical composition of the present teachings.

In some embodiments, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In some embodiments, said abnormal cell growth is a benign proliferative disease, including, but not limited to, psoriasis, benign prostatic hypertrophy or restinosis.

In some embodiments, the method further comprises administering to the mammal an amount of one or more substances selected from anti-tumor agents, anti-angiogenesis agents, signal transduction inhibitors, and antiproliferative agents, which amounts are together effective in treating said abnormal cell growth. Such substances include those disclosed in PCT Publication Nos. WO 00/38715, WO 00/38716, WO 00/38717, WO 00/38718, WO 00/38719, WO 00/38730, WO 00/38665, WO 00/37107 and WO 00/38786, the disclosures of which are incorporated herein by reference in their entireties.

Examples of anti-tumor agents include mitotic inhibitors, for example vinca alkaloid derivatives such as vinblastine vinorelbine, vindescine and vincristine; colchines allochochine, halichondrine, N-benzoyltrimethyl-methyl ether colchicinic acid, dolastatin 10, maystansine, rhizoxine, taxanes such as taxol (paclitaxel), docetaxel (Taxotere), 2'-N-[3-(dimethylamino)propyl]glutaramate (taxol derivative), thiocholchicine, trityl cysteine, teniposide, methotrexate, azathioprine, fluorouricil, cytocine arabinoside, 2'2'-difluorodeoxycytidine (gemcitabine), adriamycin and mitamycin. Alkylating agents, for example cis-platin, carboplatin oxiplatin, iproplatin, Ethyl ester of N-acetyl-DL-sarcosyl-L-leucine (Asaley or Asalex), 1,4-cyclohexadiene-1,4-dicarbamic acid, 2,5-bis(1-azirdinyl)-3,6-dioxo-, diethyl ester (diaziquone), 1,4-bis(methanesulfonyloxy)butane (bisulfan or leucosulfan) chlorozotocin, clomesone, cyanomorpholinodoxorubicin, cyclodisone, dianhydroglactitol, fluorodopan, hepsulfam, mitomycin C, hycantheonemitomycin C, mitozolamide, 1-(2-chloroethyl)-4-(3-chloropropyl)-piperazine dihydrochloride, piperazinedione, pipobroman, porfiromycin, spirohydantoin mustard, teroxirone, tetraplatin, thiotepa, triethylenemelamine, uracil nitrogen mustard, bis(3-mesyloxypropyl)amine hydrochloride, mitomycin, nitrosoureas agents such as cyclohexyl-chloroethylnitrosourea, methylcyclohexyl-chloroethylnitrosourea 1-(2-chloroethyl)-3-(2,6-dioxo-3-piperidyl)-1-nitroso-urea, bis(2-chloroethyl)nitrosourea, procarbazine, dacarbazine, nitrogen mustard-related compounds such as mechloroethamine, cyclophosphamide, ifosamide, melphalan, chlorambucil, estramustine sodium phosphate, strptozoin, and temozolamide. DNA anti-metabolites, for example 5-fluorouracil, cytosine arabinoside, hydroxyurea, 2-[(3hydroxy-2-pyrinodinyl)methylene]-hydrazinecarbothioamide, deoxyfluorouridine, 5-hydroxy-2-formylpyridine thiosemicarbazone, alpha-2'-deoxy-6-thioguanosine, aphidicolin glycinate, 5-azadeoxycytidine, beta-thioguanine deoxyriboside, cyclocytidine, guanazole, inosine glycodialdehyde, macbecin II, pyrazolimidazole, cladribine, pentostatin, thioguanine, mercaptopurine, bleomycin, 2-chlorodeoxyadenosine, inhibitors of thymidylate synthase such as raltitrexed and pemetrexed disodium, clofarabine, floxuridine and fludarabine. DNA/RNA antimetabolites, for example, L-alanosine, 5-azacytidine, acivicin, aminopterin and derivatives thereof such as N-[2-chloro-5-[[(2,4-diamino-5-methyl-6-quinazolinyl)-methyl]amino]benzoyl]-L-aspartic acid, N-[4-[[(2,4-diamino-5-ethyl-6-quinazolinyl)methyl]amino]-benzoyl]-L-aspartic acid, N-[2-chloro-4-[[(2,4-diaminopteridinyl) methyl]amino]benzoyl]-L-aspartic acid, soluble Baker's antifol, dichloroallyl lawsone, brequinar, ftoraf, dihydro-5-azacytidine, methotrexate, N-(phosphonoacetyl)-L-aspartic acid tetrasodium salt, pyrazofuran, trimetrexate, plicamycin, actinomycin D, cryptophycin, and analogs such as cryptophycin-52 or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; proteins, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

Anti-angiogenesis agents include MMP-2 (matrix-metalloprotienase 2) inhibitors, MMP-9 (matrix-metalloproteinase 9) inhibitors, and COX-II (cyclooxygenase II) inhibitors. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases MMP-1, MMP-3, MMP-4, MMP-5, MMP-6, MMP-7, MMP-8, MMP-10, MMP-11, MMP-12, and MMP-13).

Examples of MMP inhibitors include AG-3340, RO 32-3555, RS 13-0830, and the following compounds: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxy-carbamoyltetrahydro-pyran-4-yl)-amino]-propionic acid; 3-exo-3-[4-(4-chloro-phenoxy) benzene-sulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1] octane-3-carboxylic acid hydroxyamide; 3-[4-(4-fluoro-phenoxy)-benzenesulfonylamino]-tetrahydro-furan-3-carboxylic acid hydroxyamide; and pharmaceutically acceptable salts, solvates and hydrates thereof.

Examples of signal transduction inhibitors include agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

VEGF inhibitors, for example SU-5416 and SU-6668 (Sugen Inc. of South San Francisco, Calif., USA), can also be combined or co-administered with the composition. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody bevacizumab (Genentech, Inc. of South San Francisco, Calif.); and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with the composition. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used include inhibitors of the enzyme farnesyl protein transferase and inhibitors of the receptor tyrosine kinase PDGFr, including the compounds disclosed and claimed in the following U.S. patent applications: Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

Compositions of the invention can also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors. Specific CTLA4 antibodies that can be used in the present invention include those described in U.S. Provisional Application 60/113,647 (filed Dec. 23, 1998) which is herein incorporated by reference in its entirety.

Unless otherwise stated, the following terms used in the specification and claims have the meanings discussed below. Variables defined in this section, such as R, X, n and the like, are for reference within this section only, and are not meant to have the save meaning as may be used outside of this definitions section. Further, many of the groups defined herein can be optionally substituted. The listing in this definitions section of typical substituents is exemplary and is not intended to limit the substituents defined elsewhere within this specification and claims.

As used herein, the symbol [------] when incorporated into the chemical structure of a substituent means that the atom to which [------] is attached is the point of attachment of that substitutent to some position on another molecule. For example, X in the hypothetical molecule CH$_3$CH$_2$—X might be defined as X is

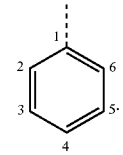

In which case, the placement of [------] attached to the arbitrarily numbered position C-1, means that C-1 of the phenyl ring is attached to the methylene carbon.

The symbols "ıllll" and "◢", when used together in a single molecule without further indication otherwise, merely indicate relative stereochemistry of trans or cis where applicable. The symbol "ıllll" and the symbol "◢", used together or separately, in combination with an indication of them representing the absolute stereochemistry, or an indication of "S" or "R" in the corresponding chemical structure or the accompanying chemical name, indicate the absolute stereochemistry of the corresponding chiral center.

"Aliphatic" refers to straight-chain, branched or cyclic $C_1$-$C_{12}$ hydrocarbons which are completely saturated or which contains one or more units of unsaturation but which are not aromatic. Examples of aliphatic groups include linear, branched or cyclic alkyl, alkenyl, alkynyl groups and hybrids thereof such as (cycloalkyl)alkyl, (cycloalkenyl)alkyl, etc. An aliphatic group may be optionally substituted by 1-6 substituents. Suitable substituents on an aliphatic group include: 3-12 member heterocyclyl, $C_6$-$C_{10}$ aryl, 5-12 member heteroaryl, halide, —NO$_2$, NH$_2$, NR$_2$, —CN, —COR, —COOR, —CONR$_2$, —OH, —OR, —OCOR, —SR, —SOR, —SO$_2$R, —SONR$_2$, —SO$_2$NR$_2$, wherein R is H, $C_1$-$C_{10}$ alkyl, 3-10 member heterocyclyl, $C_6$-$C_{10}$ aryl, 5-12 member heteroaryl.

"$C_1$-$C_{12}$ alkyl" refers to a straight chain or branched saturated hydrocarbon radical having from 1 to 12 carbon atoms.

A $C_1$-$C_{12}$ alkyl group may be optionally substituted by at least one substituent. Suitable substituents on a $C_1$-$C_{12}$ alkyl group include, but are not limited to, 3-12 member heterocyclyl, $C_6$-$C_{10}$ aryl, 5-12 member heteroaryl, halide, —$NO_2$, —$NR_2$, —CN, —COR, —COOR, —$CONR_2$, —OH, —OR, —OCOR, —SR, —SOR, —$SO_2R$, —$SONR_2$, —$SO_2NR_2$, wherein each R is independently —H, $C_1$-$C_{10}$ alkyl, 3-12 member heterocyclyl, $C_6$-$C_{10}$ aryl, 5-12 member heteroaryl. Examples of $C_1$-$C_{12}$ alkyl groups include, but are not limited to methyl, ethyl, propyl, isopropyl, butyl, sec-butyl, iso-butyl, tert-butyl, pentyl, neo-pentyl, sec-pentyl, hexyl, heptyl, octyl, and the like, including substituted forms thereof. Further, the term "alkyl" refers to a straight chain or branched saturated hydrocarbon radical of 1 to 20 carbon atoms, or 1 to 12 carbon atoms, or 1 to 8 carbon atoms, or 1 to 6 carbon atoms, or 1 to 4 carbon atoms. "Lower alkyl" refers specifically to an alkyl group having 1 to 4 carbon atoms. Alkyl may be substituted or unsubstituted. Suitable substituents on an alkyl group are the same as those described for a $C_1$-$C_{12}$ alkyl group.

"Cycloalkyl" refers to a cyclic saturated hydrocarbon radical having from 3 to 20 carbon atoms. A cycloalkyl group may be monocyclic and where permissible may be bicyclic or polycyclic. A cycloalkyl group may be optionally substituted by at least one substituent. Suitable substituents on a cycloalkyl group are the same as those described for an alkyl group. Examples of cycloalkyl groups include, but are not limited to cyclopropyl, cyclobutyl, cyclopentyl, cyclohexyl, cycloheptyl, cyclooctyl, nobornyl, adamantyl, and the like, including substituted forms thereof.

"Nonaromatic carbocyclyl" refers to a 3 to 12 member all-carbon monocyclic ring group, all-carbon bicyclic or multicyclic ring system group wherein one or more of the rings may contain one or more double bonds but none of the rings has a completely conjugated pi-electron system. Examples, without limitation, of nonaromatic carbocyclyl are cyclopropyl, cyclobutyl, cyclopentyl, cyclopentenyl, cyclohexyl, cyclohexadienyl, adamantanyl, cycloheptyl, cycloheptatrienyl, and the like. A nonaromatic carbocyclyl may be substituted or unsubstituted. Typical substituent groups are the same with those of alkyl group, as defined herein. Illustrative examples of nonaromatic carbocyclyl are derived from, but not limited to, the following:

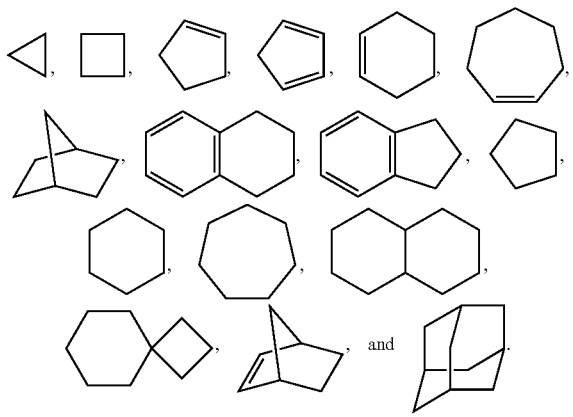

"Unsaturated nonaromatic carbocyclyl" refers to a nonaromatic carbocyclyl, as defined herein, that contains at least one carbon carbon double bond, one carbon carbon triple bond or a benzene ring.

"$C_2$-$C_{12}$ alkenyl" refers to a straight chain or branched unsaturated hydrocarbon radical having from 2 to 12 carbon atoms. A $C_2$-$C_{12}$ alkenyl group may have one or more points of unsaturation (i.e.—one or more carbon-carbon double bonds). In the case where $C_2$-$C_{12}$ alkenyl has more than one carbon-carbon double bond, the carbon-carbon double bonds can be conjugated or unconjugated. A $C_2$-$C_{12}$ alkenyl group may be optionally substituted by at least one substituent. Suitable substituents on a $C_2$-$C_{12}$ alkenyl group are the same as those described for a $C_1$-$C_{12}$ alkyl group. Examples of $C_2$-$C_{12}$ alkenyl include, but are not limited to, ethenyl, 1-propenyl, 2-propenyl, 1-butenyl, 2-butenyl, iso-butenyl, and the like, including substituted forms thereof. Further, the term "alkenyl" refers to a straight chain or branched unsaturated hydrocarbon radical having from 2 to 20 carbon atoms, or 2 to 12 carbon atoms, or 2 to 8 carbon atoms, or 2 to 6 carbon atoms, or 2 to 4 carbon atoms. An alkenyl group may have one or more points of unsaturation (i.e.—one or more carbon-carbon double bonds). In the case where an alkenyl group has more than one carbon-carbon double bond, the carbon-carbon double bonds can be conjugated or unconjugated. An alkenyl group may be substituted or unsubstituted. Suitable substituents on an alkenyl group are the same as those described for a $C_1$-$C_{12}$ alkyl group.

"Alkoxy" refers to —$OR^c$ wherein $R^c$ is $C_1$-$C_{12}$ alkyl, $C_2$-$C_{12}$ alkenyl, $C_2$-$C_{12}$ alkynyl, $C_3$-$C_{12}$ cycloalkyl or ($C_1$-$C_6$ alkylene)-($C_3$-$C_{12}$ cycloalkyl). A "$C_1$-$C_{12}$ alkoxy" refers to an alkoxy group, as defined herein, wherein $R^c$ has 1 to 12 total carbon atoms.

"Alkoxyalkyl" refers to an alkyl, as defined herein, that is substituted by at least one alkoxy group as defined herein. A "$C_2$-$C_6$ alkylalkoxy" refers an alkylalkoxy wherein the total carbon number of the alkyl and its alkoxy substituents are from 2 to 6.

"Alkylamino" refers to —$NR^pR^q$ wherein each $R^p$ and $R^q$ is independently H, $C_1$-$C_{12}$ alkyl, $C_2$-$C_{12}$ alkenyl, $C_2$-$C_{12}$ alkynyl, $C_3$-$C_{12}$ cycloalkyl, ($C_1$-$C_6$ alkylene)-($C_3$-$C_{12}$ cycloalkyl) provided $R^p$ and $R^q$ are not both H. A "monoalkylamino" refers to an alkylamino group, as defined herein, wherein one of $R^p$ and $R^q$ is H. A "dialkylamino" refers to an alkylamino group, as defined herein, wherein none of $R^p$ and $R^q$ is H. A "$C_{1-12}$ alkylamino" refers to an alkylamino group that contains 1 to 10 carbon atoms.

"$C_2$-$C_{12}$ alkynyl" refers to a straight chain or branched hydrocarbon radical having from 2-12 carbon atoms and at least one carbon-carbon triple bond. In the case where $C_2$-$C_{12}$ alkynyl has more than one carbon-carbon double bond, the carbon-carbon double bonds can be conjugated or unconjugated. A $C_2$-$C_{12}$ alkynyl group may be optionally substituted by at least one substituent. Suitable substituents on a $C_2$-$C_{12}$ alkynyl group are the same as those described for a $C_1$-$C_{12}$ alkyl group. Examples of $C_2$-$C_{12}$ alkynyl include, but are not limited to, ethynyl, 1-propynyl, 2-propynyl, 1-butynyl, 2-butynyl, and the like, including substituted forms thereof. Further, the term "alkynyl" refers to a straight chain or branched hydrocarbon radical of 2 to 20 carbon atoms, or 2 to 12 carbon atoms, or 2 to 8 carbon atoms, or 2 to 6 carbon atoms, or 2 to 4 carbon atoms, and having at least one carbon-carbon triple bond. Alkynyl may be substituted or unsubstituted. Suitable substituents on an alkynyl group are the same as those described for a $C_1$-$C_{12}$ alkyl group.

"Amino" refers to —$NH_2$.

"$C_6$-$C_{10}$ aryl" refers to an all-carbon monocyclic ring or polycyclic ring of 6 to 10 carbon atoms having a completely conjugated pi-electron system. A $C_6$-$C_{10}$ aryl group may be optionally substituted by at least one substituent. Suitable substituents on a $C_6$-$C_{10}$ aryl group are the same as those described for a $C_1$-$C_{12}$ alkyl group. Examples of $C_6$-$C_{10}$ aryl include, but are not limited to, phenyl and naphthyl. Further, the term "aryl" refers to an all-carbon monocyclic ring or polycyclic ring of 6 to 20 carbon atoms having a completely conjugated pi-electron system. The aryl group may be substituted or unsubstituted. Examples of aryl include, but are not limited to, anthracenyl, phenanthreneyl and perylenyl.

"Aralkyl" refers to alkyl, as defined herein, that is substituted with an $C_{6-10}$ aryl group as defined above; e.g., —$CH_2$-phenyl, —$(CH_2)_2$-phenyl, —$(CH_2)_3$-phenyl, $CH_3CH(CH_3)$ $CH_2$-phenyl, and the like and derivatives thereof. A $C_1$-$C_6$ aralkyl refers to a $C_1$-$C_6$ alkyl that is substituted with a $C_6$-$C_{10}$ aryl group.

"Heteroaralkyl" group means alkyl, as defined herein, that is substituted with a 5-12 membered heteroaryl group; e.g., —$CH_2$pyridinyl, —$(CH_2)_2$pyrimidinyl, —$(CH_2)_3$imidazolyl, and the like, and derivatives thereof. A $C_1$-$C_6$ heteroaralkyl refers to a $C_1$-$C_6$ alkyl that is substituted with an 5-12 membered heteroaryl group.

"Heteroaryl" refers to a monocyclic or fused ring group of 5 to 12 ring atoms containing one, two, three or four ring heteroatoms selected from N, O, and S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. Typical substituents include $C_{1-12}$ aliphatic, 3-10 membered heterocycle, 6-10 membered aryl, halide, —$NO_2$, $NH_2$, $NR_2$, —CN, —COR, —COOR, —$CONR_2$, —OH, —OR, —OCOR, —SR, —SOR, —$SO_2R$, —$SONR_2$, —$SO_2NR_2$, wherein R is a $C_{1-10}$ aliphatic, 3-10 membered heterocycle, $C_{6-10}$ aryl, 5-10 membered heteroaryl.

A "pharmaceutically acceptable heteroaryl" is one that is sufficiently stable to be attached to a compound of the invention, formulated into a pharmaceutical composition and subsequently administered to a patient in need thereof.

Examples of typical monocyclic heteroaryl groups include, but are not limited to:

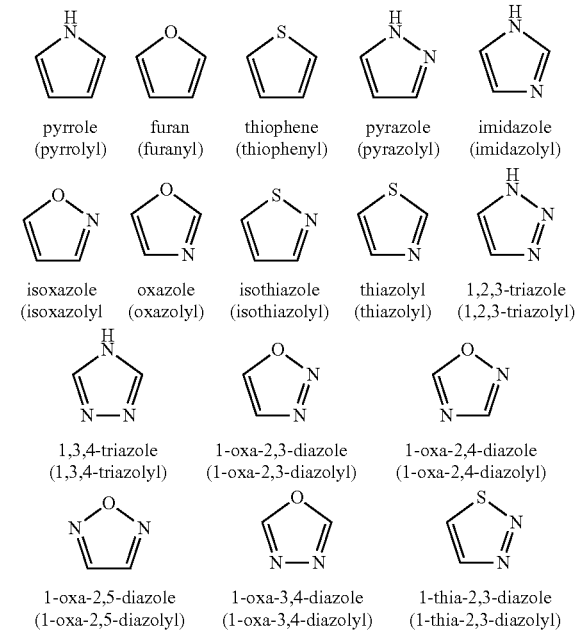

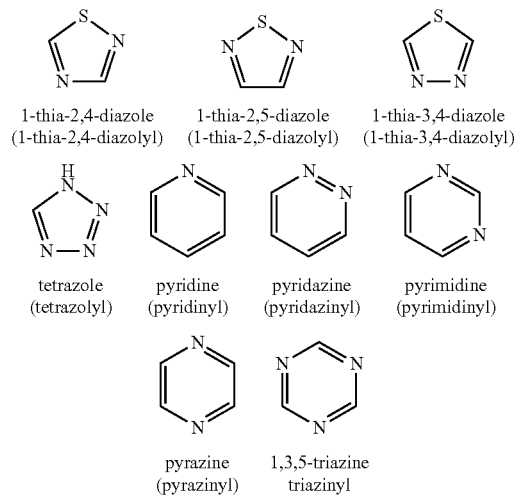

Examples of bicyclic heteroaryl groups include, but are not limited to:

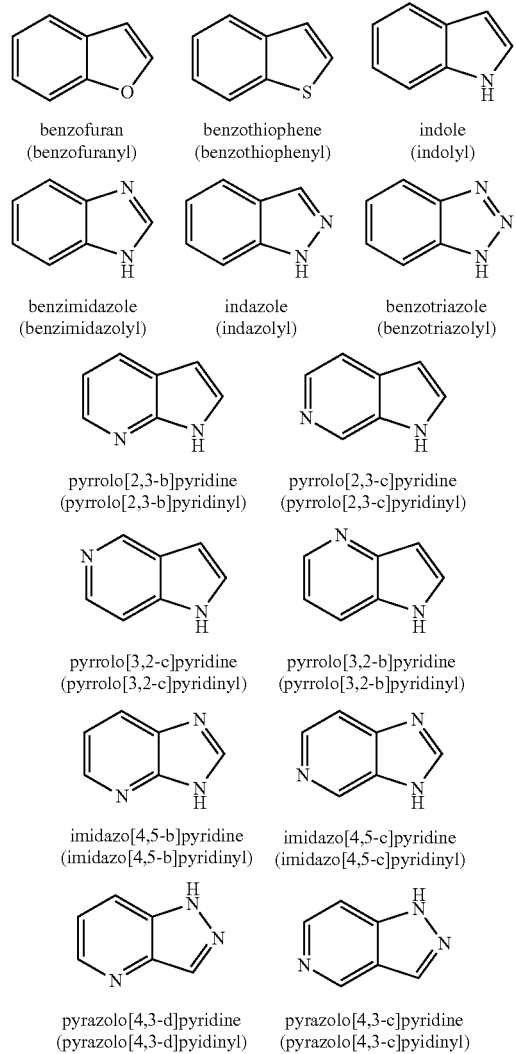

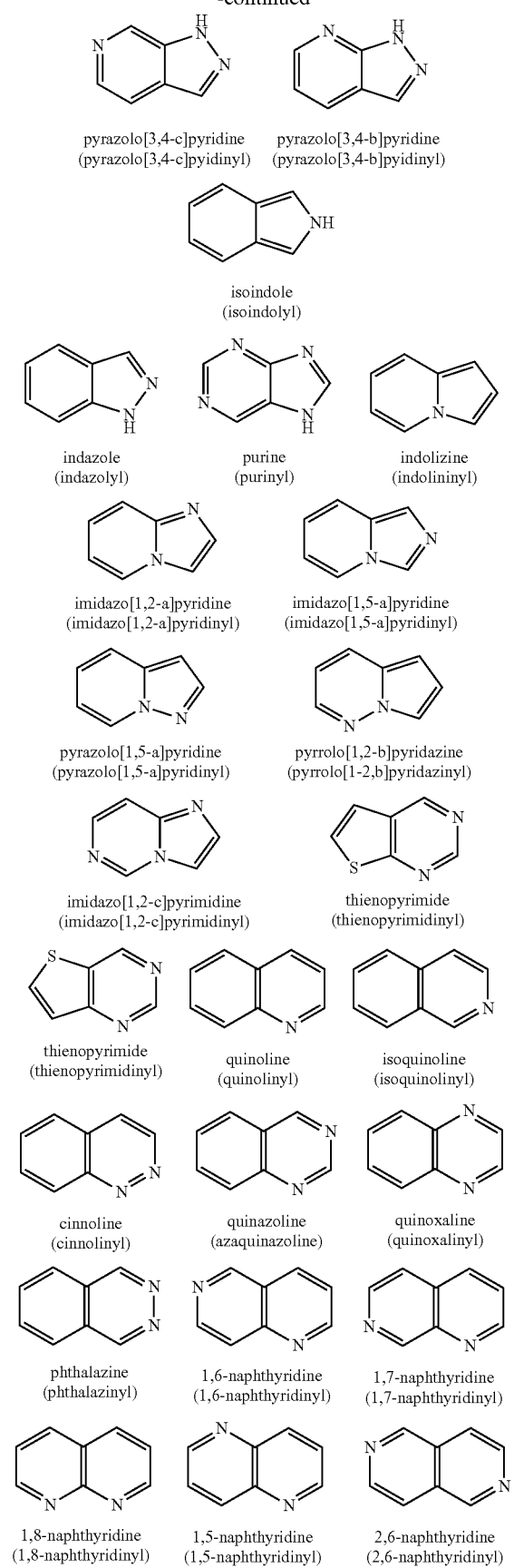
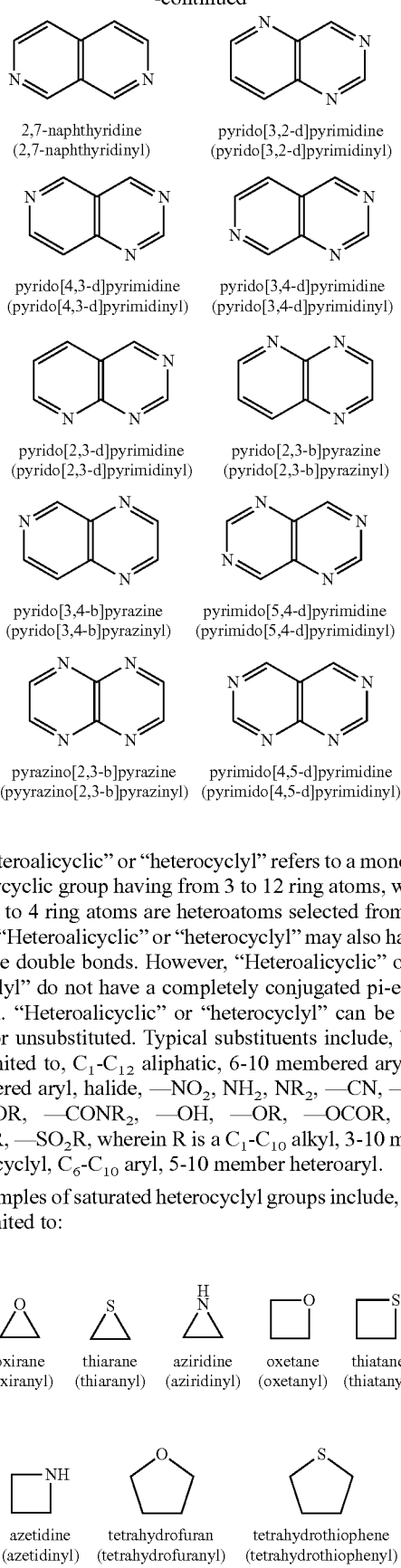

"Heteroalicyclic" or "heterocyclyl" refers to a monocyclic or polycyclic group having from 3 to 12 ring atoms, wherein from 1 to 4 ring atoms are heteroatoms selected from N, O, and S. "Heteroalicyclic" or "heterocyclyl" may also have one or more double bonds. However, "Heteroalicyclic" or "heterocyclyl" do not have a completely conjugated pi-electron system. "Heteroalicyclic" or "heterocyclyl" can be substituted or unsubstituted. Typical substituents include, but are not limited to, $C_1$-$C_{12}$ aliphatic, 6-10 membered aryl, 6-10 membered aryl, halide, —$NO_2$, $NH_2$, $NR_2$, —CN, —COR, —COOR, —$CONR_2$, —OH, —OR, —OCOR, —SR, —SOR, —$SO_2R$, wherein R is a $C_1$-$C_{10}$ alkyl, 3-10 member heterocyclyl, $C_6$-$C_{10}$ aryl, 5-10 member heteroaryl.

Examples of saturated heterocyclyl groups include, but are not limited to:

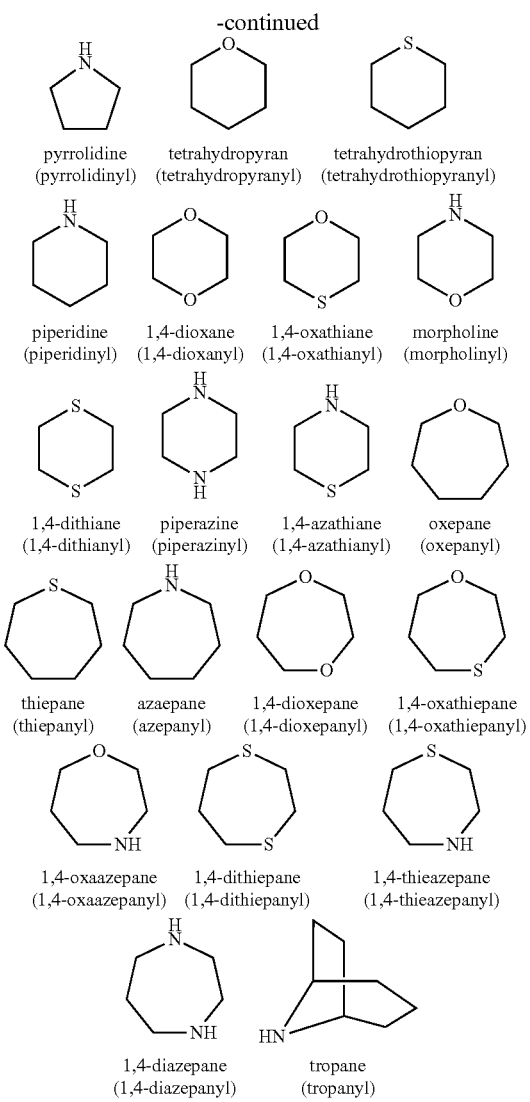

Examples of partially unsaturated heterocyclyl groups include, but are not limited to:

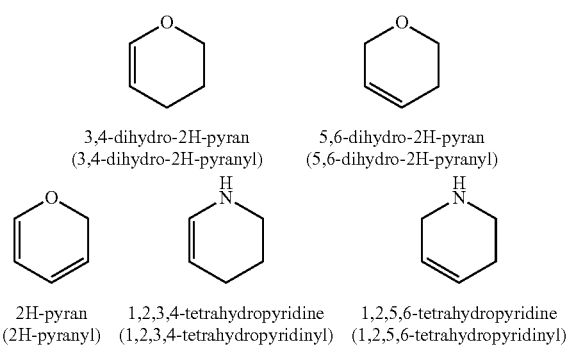

When "ene" is added after "yl" at the end a term to form a new term, the new term refers to a diradical formed by removing one hydrogen atom from the original term of which the new term derived from. For example, an alkylene refers to a diradical group formed by removing one hydrogen atom from an alkyl group and that a "methylene" refers to a divalent radical —$CH_2$— derived from removing one hydrogen atom from methyl. More examples of such diradicals include, but are not limited to: alkenylene, alkynylene, cycloalkylene, phenylene, heterocyclylene, heteroarylene and (nonaromatic unsaturated carbocyclylene), which are derived from alkenyl, alkynyl, cycloalkyl, phenyl, heterocyclyl, heteroaryl and (nonaromatic unsaturated carbocyclyl), respectively. For example, "cyclopropylene" refers to both

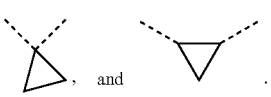

For example, "$C_1$-$C_3$ alkylene" refers to all of the following: —$CH_2$—, —$CH(CH_3)$—, —$CH_2$—$CH_2$—, —$CH_2$—$CH_2$—$CH_2$—, —$CH(CH_3)$—$CH_2$— and —$CH(CH_2CH_3)$—.

"oxo" refers to an oxygen double bond "=O" substitution.

"Hydroxy" refers to —OH.

"Perfluoroalkyl" refers to an alkyl group in which all of its hydrogen atoms are replaced by fluorine atoms.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts that retain the biological effectiveness and properties of the parent compound. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"PK" refers to receptor protein tyrosine kinase (RTKs), non-receptor or "cellular" tyrosine kinase (CTKs) and serine-threonine kinases (STKs).

"Modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

"Catalytic activity" refers to the rate of phosphorylation of tyrosine under the influence, direct or indirect, of RTKs and/or CTKs or the phosphorylation of serine and threonine under the influence, direct or indirect, of STKs.

"Contacting" refers to bringing a compound of the present teachings and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, can be determined before use of compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium.

"In vivo" refers to procedures performed within a living organism such as, without limitation, a mouse, rat or rabbit.

"PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukariotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has at least one of the following effects:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and
(4) relieving to some extent (or, preferably, eliminating) one or more symptoms associated with the cancer.

"Monitoring" means observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art. The effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

"Natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

DETAILED DESCRIPTION

Compounds of formulas I-VII can be made following the synthetic routes in Scheme 1 and Scheme 2. In Scheme 1 and Scheme 2 and the descriptions following, "BOC", "Boc" or "boc" means N-tert-butoxycarbonyl, DCM means $CH_2Cl_2$, DIPEA (also known as Hunig's base) means diisopropyl ethyl amine, DMA means N,N-dimethylacetamide, "DMF" means dimethyl formamide, "DMSO" means dimethylsulfoxide, Et means —$CH_2CH_3$, "MTBE" means methyl t-butyl ether, NMP means 1-methyl-2-pyrrolidinone, TEA means triethyl amine, TFA means trifluoro acetic acid, THF means tetrahydrofuran. While schemes 1 and 2 and the description refer to compound I, schemes 1 and 2 and the description are equally applicable to compounds II, III, IV, V, VI and VII.

Scheme 1
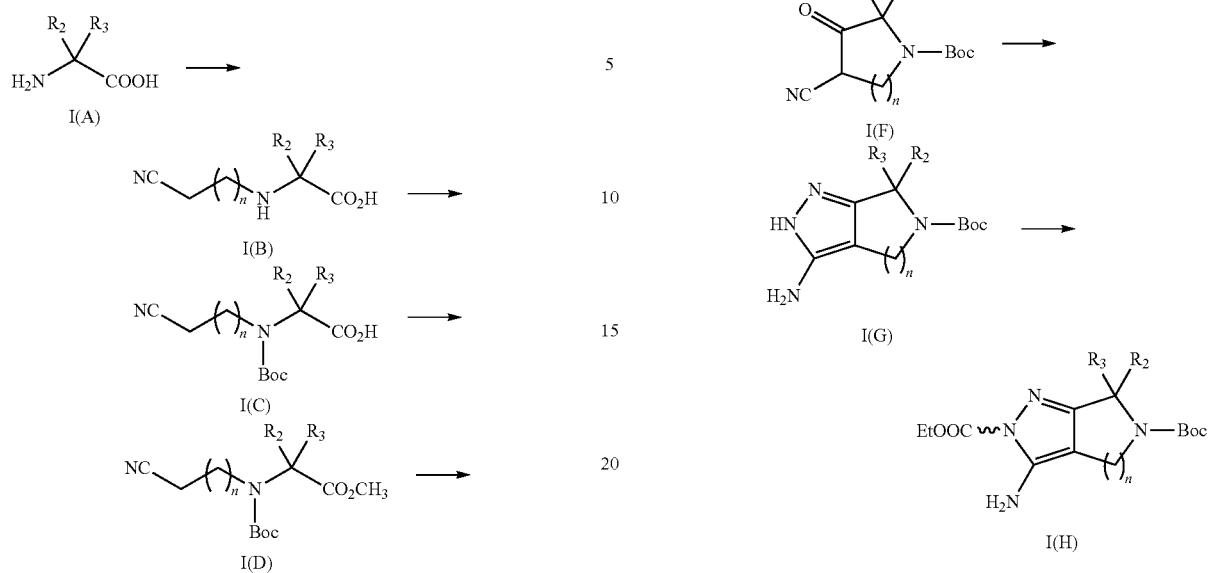
Scheme 2
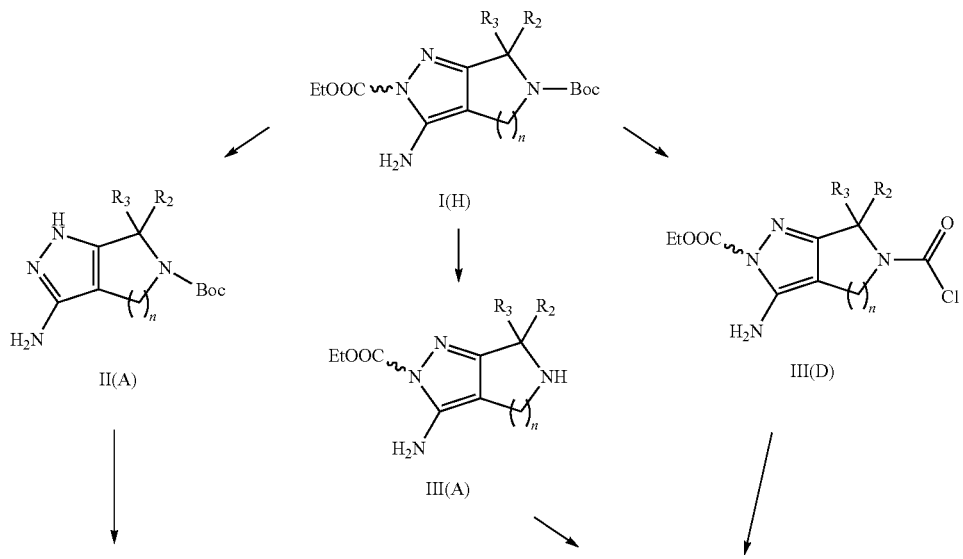
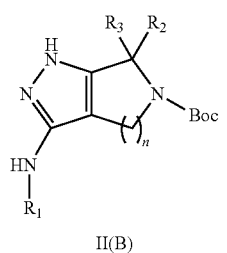
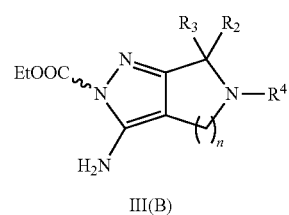

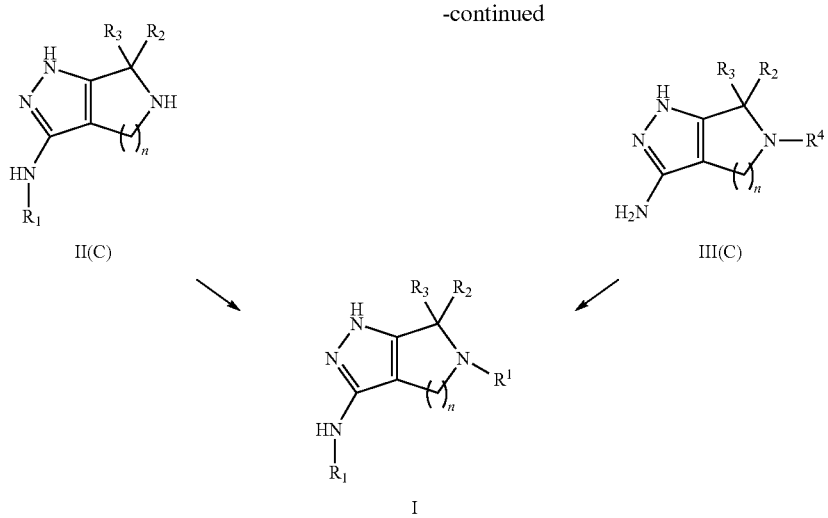

Scheme 1 illustrates the synthesis of the intermediate I(H) used to make compounds of formula I. The amino group of the substituted amino acid I(A) is alkylated to give compound I(B). This can typically be done by treating compound I(A) with an alkylating agent in the presence of a base. An activated electrophilic double bond moiety is a commonly used alkylating reagent. A typical reaction condition of alkylating I(A) with an activated electrophilic double bond moiety is to treat I(A) with the activated double bond moiety in the presence of a strong base. Subsequent aqueous work up affords compound I(B). The amino group of compound I(B) is then protected with a boc group to give compound I(C). This can typically be done by treating compound I(B) with Boc agent in the presence of a base. A typical condition is to treat compound I(B) with $(Boc)_2O$ in the presence of $Me_4NOH$ in MeCN as a solvent. The carboxylic acid group of compound I(C) is then converted into a methyl ester of compound I(D). A typical condition of converting the carboxylic acid group into the methyl ester group is to treat I(C) with methyl iodide in DMF in the presence of a base. Compound I(D) then undergoes an intramolecular aldol condensation to give compound I(F). This can typically be done by treating compound I(D) with a strong base in an aprotic solvent. A typical condition is to treat compound I(D) with t-BuOK in toluene. Subsequent aqueous workup gives compound I(F). Compound I(F) then undergoes a 2+3 cyclization with a hydrazine moiety to form compound I(G). A typical condition of the cyclization is to reflux compound I(F) with hydrazine and acetic acid in EtOH. The free base pyrazole nitrogen of compound I(G) is then acylated to give compound I(H). A typical condition of the acylation is to treat compound I(G) with chloro ethyl carbonate in THF.

More detailed synthetic conditions of Scheme 1 can be found in U.S. Patent Application Publication No. 2003/0171357 and PCT Publication WO 02/12242, the disclosure of which are incorporated herein by reference.

Scheme 2 illustrates two routes through which compounds of formula I can be made from intermediate I(H). In the first route of Scheme 2, the ethyl ester protecting group of the pyrazole nitrogen of I(H) is cleaved to give compound II(A). This reaction can typically be carried out by treating the substrate I(H) with a base. A typical reaction condition is to reflux the substrate I(H) in dioxane and DCM in the presence of 2-3 equivalents of LiOH followed by aqueous workup.

Compound II(A) undergoes a nucleophilic reaction with an electrophilic $R^1$ moiety to give compound II(B). This nucleophilic reaction can be alkylation, acylation, sulfonylation, reductive amination, and many other reactions that can be carried out for the pyrazole amino group of compound II(A). A typical alkylation condition for the transformation of II(A) to II(B) is to react II(A) with $R^1$—Cl in the presence of excess base, such as DMA and TEA at an elevated temperature of 80-140° C., and optionally under microwave radiation. Subsequent aqueous workup gives compound II(B). The Boc group on the pyrrole nitrogen of compound II(B) is then removed to give compound II(C). This can typically be done by treating II(B) with a strong acid. A typical condition is to treat compound II(B) with 1:1 TFA:DCM at room temperature for two hours. Subsequent aqueous work up affords compound II(C). Alternatively, the transformation of compound II(A) to compound II(C) can be carried out in a single step. The alkylation of compound II(A) and the removal of the boc protecting group of the pyrrole nitrogen can be carried out in an one pot reaction. A typical reaction condition is to mix substrate II(A) with the alkylating reagent $R^1$—Cl, excess DMA, one equivalent HCl, in dioxane at an elevated temperature and under microwave radiation. Compound II(C) then undergoes a nucleophilic reaction with an $R^4$ electrophile to give compound I. The nucleophilic reaction can be alkylation, acylation, sulfonylation, reductive amination and other reactions that a secondary alkyl amine can carry out. An acylation reaction of compound II(C) can be carried out by reacting compound II(C) with an acylating $R^4$ moiety. A typical acylation reaction condition is to react II(C) with an isocyanate $R^4$ moiety in the presence of TEA at room temperature. Subsequent aqueous workup gives compound I.

In the second route of Scheme 2, the boc group on the pyrrole nitrogen is removed to give compound III(A). The can typically be carried out by treating compound I(H) with a strong acid. A typical reaction condition is to treat compound I(H) with 4N HCl in dioxane and DCM. Subsequent aqueous workup affords compound III(A). Compound III(A) can then undergoes a nucleophilic reaction with an $R^4$ electrophile give compound III(B). Because the —$NH_2$ group attached to the pyrazole in compound III(A) is less reactive than the pyrrole nitrogen of III(A), the transformation of III(A) to III(B) can be carried out without protecting the pyrazole —$NH_2$ group of compound III(A). The nucleophilic reaction carried out for this transformation can be an alkylation, acylation, sulfonylation, reductive amination. Relative mild reaction conditions are preferred to achieve the reaction selectivity. An acylation reaction of III(A) to give III(B) is carried out by treating compound III(A) with an acylating reagent in the presence of base. A typical reaction condition is to mix compound III(A) with excess of base, such as DIPEA in DCM and adding the resulting solution to an isocyanate at 0° C. The reaction mixture is held at 0° C. for about two hours for the reaction to go complete. Subsequent aqueous workup gives compound III(B).

Selective acylation of the pyrrole nitrogen in the presence of the unprotected —$NH_2$ attached to the pyrazole to obtain compound III(B) can also be done from compound I(H), through the intermediate of III(D). The pyrrole nitrogen of I(H) is deprotected and further acylated to give compound III(D). This can be done by treating compound I(H) with a strong acid, reducing the reaction mixture to a residue and then reacting the residue with an acylating agent. A typical reaction condition is to treat compound I(H) with 4N HCl in dioxane at room temperature for two hours and subsequently remove all solvent. The residue is dissolved and basified by a base such as DIPEA. The resulting solution is then added to triphosgene at 0° C. The reaction mixture is allowed to stir at 0° C. for an hour. Subsequent aqueous work up affords compound III(D). The crude compound III(D) then reacts with a nucleophile to give compound III(B). A typical reaction condition is to mix compound III(D) with a $R^4$ nucleophilic amine moiety in the presence of a non-nucleophilic amine in DCM at room temperature. The reaction mixture is be held at room temperature for about two hours. Subsequent aqueous workup afford compound III(B).

The ethyl ester protecting group on the pyrazole nitrogen of compound III(B) is removed to give the free base compound III(C). This can typically be done by treating compound III (B) with a base. A typical reaction condition is to reflux compound III(B) in dioxane and DCM in the presence of 2-3 equivalents of LiOH. Subsequent aqueous workup affords compound III(C). Compound III(C) then undergoes a nucleophilic reaction with an $R^1$ electrophile moiety. This nucleophilic reaction can be an acylation, alkylation, sulfonylation, reductive amination or one of many other reactions that an amine functionality carries out. A typical alkylation reaction condition is to treating compound III(C) with an alkylating agent such as $R^1$—Cl, in the presence of a base such as 2 equivalents of DMA, in a solvent such as NMP, the reaction mixture is then heated under microwave radiation to 140° C. for hour hours. Subsequent aqueous workup and purification gives compound of formula I.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Pharmaceutically acceptable salts include acid addition and base salts (including disalts). Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002), the disclosure of which is incorporated herein by reference in its entirety.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

Also within the scope of the invention are polymorphs, prodrugs, and isomers (including optical, geometric and tautomeric isomers) of the inventive compounds Derivatives of compounds of the invention which may have little or no pharmacological activity themselves but can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some examples of prodrugs in accordance with the invention include:

(i) where the compound contains a carboxylic acid functionality (—COOH), an ester thereof, for example, replacement of the hydrogen with ($C_1$-$C_8$)alkyl;

(ii) where the compound contains an alcohol functionality (—OH), an ether thereof, for example, replacement of the hydrogen with ($C_1$-$C_6$)alkanoyloxymethyl; and (iii) where the compound contains a primary or secondary amino functionality (—NH$_2$ or —NHR where R≠H), an amide thereof, for example, replacement of one or both hydrogens with (C$_1$-C$_{10}$)alkanoyl.

Further examples of replacement groups in accordance with the foregoing examples and examples of other prodrug types may be found in the aforementioned references.

Finally, certain inventive compounds may themselves act as prodrugs of other of the inventive compounds.

Compounds of the invention containing one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

Included within the scope of the invention are all stereoisomers, geometric isomers and tautomeric forms of the inventive compounds, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$O, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Pharmaceutically acceptable solvates in accordance with the invention include those wherein the solvent of crystallization may be isotopically substituted, e.g. D$_2$O, d$_6$-acetone, d$_6$-DMSO.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds can be administered alone or in combination with one or more other compounds of the invention, or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and microneedle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 μL to 100 μL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Rectal/Intravaginal Administration

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

In the following examples and preparations, "BOC", "Boc" or "boc" means N-tert-butoxycarbonyl, DCM means $CH_2Cl_2$, DIPEA or DIEA means diisopropyl ethyl amine, DMA means N,N-dimethylacetamide, "DMF" means dimethyl formamide, "DMSO" means dimethylsulfoxide, "DPPP" means 1,3-bis(diphenylphosphino)propane, "HOAc" means acetic acid, "IPA" means isopropyl alcohol. "MTBE" means methyl t-butyl ether, "NMP" means 1-methyl 2-pyrrolidinone, TEA means triethyl amine, TFA means trifluoro acetic acid.

Specific Examples

Example 1

6,6-dimethyl-N-[trans-2-phenylcyclopropyl]-3-(thieno[3,2-d]pyrimidin-4-ylamino)-4,6-dihydropyrrolo[3,4-c]pyrazole-5(1H)-carboxamide

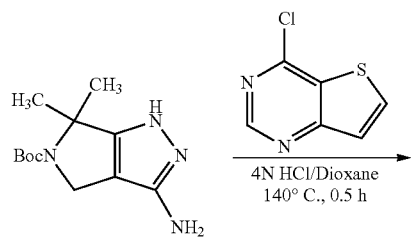

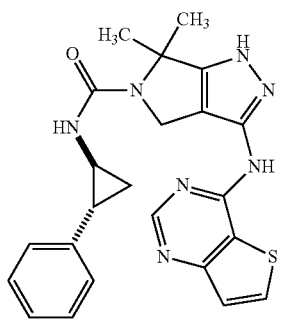

1

Preparation of Compound 1a: N-(6,6-dimethyl-1,4,5,6-tetrahydropyrrolo[3,4-c]pyrazol-3-yl)thieno[3,2-d]pyrimidin-4-amine To a stirring solution of tert-butyl 3-amino-6,6-dimethyl-4,6-dihydropyrrolo[3,4-c]pyrazole-5(1H)-carboxylate (0.62 g, 2.46 mmol) in DMA (3 mL) was added 4-chlorothieno[3,2-d]pyrimidine (0.44 g, 1.05 eq) and 4N HCl solution in 1,4-dioxane (0.65 ml, 1.05 eq). The resulting mixture was heated to 140° C. for 0.5 hours in microwave reactor. It was cooled to room temperature and the compound 1a was precipitated. Filtration and washing with $CH_2Cl_2$ provided compound 1a as a yellow solid (0.48 g, 68% yield). Compound 1a was directly carried onto the next reaction without further purification. LCMS (API-ES, M+H$^+$): 287.0.

To a stirring mixture compound 1a (0.12 g, 0.42 mmol), and TEA (0.117 ml, 2 eq) in DMSO (1 ml) and $CH_2Cl_2$ (2 ml) was added trans-2-phenylcyclopropyl isocyanate (0.068 ml, 1.1 eq). The resulting mixture was stirred at room temperature for 2 h. The reaction mixture was purified by prep-HPLC to provide the title compound 1 as a white solid (0.019 g, 10%). $^1$H NMR (CD$_3$OD) δ: 1.06 (m, 1H), 1.11 (m, 1H), 1.68 (d, J=4.04 Hz, 6H), 1.98 (m, 1H), 2.69 (m, 1H), 4.43 (s, 2H), 7.01-7.07 (m, 3H), 7.11-7.17 (m, 2H), 7.34 (d, J=5.56 Hz, 1H), 8.04 (d, J=5.31 Hz, 1H), 8.59 (s, 1H). Anal. ($C_{23}H_{23}N_7OS.0.3HOAc.0.8H_2O$) C, H, N. HPLC: >95% purity.

Example 2

3-[(2-chlorothieno[3,2-d]pyrimidin-4-yl)amino]-6,6-dimethyl-N-[trans-2-phenylcyclopropyl]-4,6-dihydropyrrolo[3,4-c]pyrazole-5(1H)-carboxamide

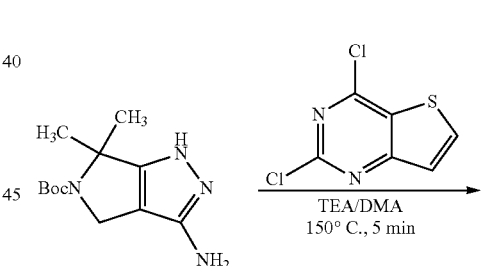

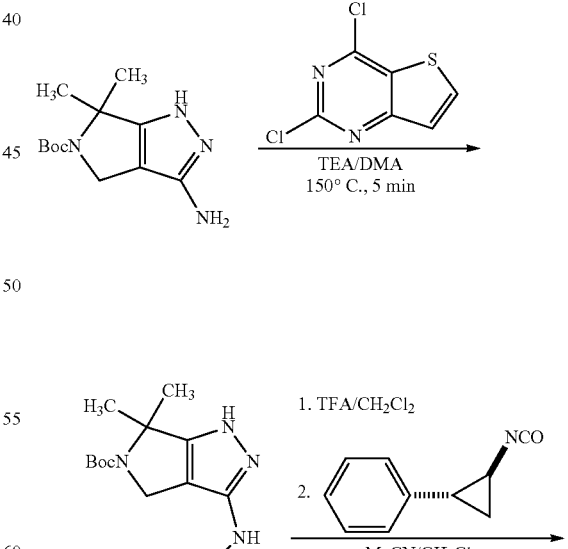

-continued

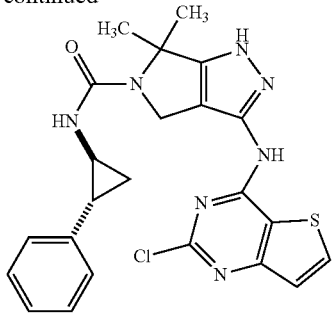

2

Preparation of Compound 2a: Tert-butyl-3-[(2-chlorothieno[3,2-d]pyrimidin-4-yl)amino]-6,6-dimethyl-4,6-dihydropyrrolo[3,4-c]pyrazole-5(1H)-carboxylate To a stirring solution of tert-butyl 3-amino-6,6-dimethyl-4,6-dihydropyrrolo[3,4-c]pyrazole-5(1H)-carboxylate (2.4 g, 9.5 mmol) in DMA (10 mL) was added 2,4-dichlorothieno[3,2-d]pyrimidine (2.05 g, 1.05 eq) and triethylamine (2.64 ml, 2 eq). The resulting mixture was heated to 150° C. for 5 minutes in microwave reactor. Saturated NaHCO$_3$ was added and the mixture was extracted with ethyl acetate. The organic layer was dried over sodium sulfate, concentrated in vacuo. The residue was washed with methylene chloride. Compound 2a (2.71 g, 68%) was obtained as a brown solid and directly carried onto the next without further purification. LCMS (API-ES, M+H$^+$): 421.

To a stirring mixture of compound 2a (0.102 g, 0.24 mmol) in CH$_2$Cl$_2$ (2 ml), was added TFA (2 ml). The resulting mixture was stirred at room temperature for 2 h. After the reaction mixture was concentrated in vacuo, a solution of TEA (135 ul, 4 eq) in MeCN (1 ml) CH$_2$Cl$_2$ (1 ml) was added and followed by trans-2-phenylcyclopropyl isocyanate. The resulting mixture was stirred at room temperature for 1 h. The reaction mixture was purified by prep-HPLC to provide compound 2 as a white solid (0.021 g, 18%). $^1$H NMR (CD$_3$OD) δ: 1.04-1.12 (m, 2H), 1.69 (d, J=3.28 Hz, 2H), 1.95 (m, 1H), 2.67-2.73 (m, 1H), 4.48 (s, 2H), 7.01-7.06 (m, 3H), 7.11-7.17 (m, 2H), 7.25 (d, J=5.31 Hz, 1H), 8.05 (d, J=4.55 Hz, 1H). Anal. (C$_{23}$H$_{22}$N$_7$OSCl.0.4HOAc.0.4H$_2$O) C, H, N. HPLC: >95% purity.

Example 3

N-(5-{[(2S)-2-benzyl-4-methylpiperazin-1-yl]carbonyl}-6,6-dimethyl-1,4,5,6 tetrahydropyrrolo[3,4-c]pyrazol-3-yl)-2-chlorothieno[3,2-d]pyrimidin-4-amine

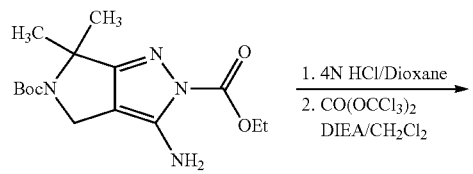

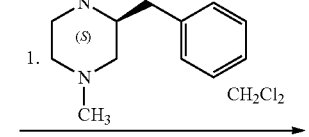

3a

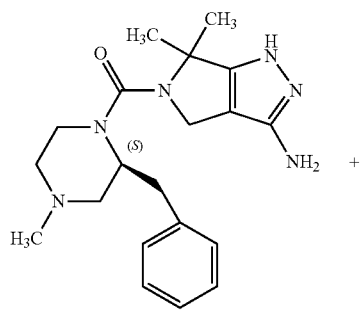

3b

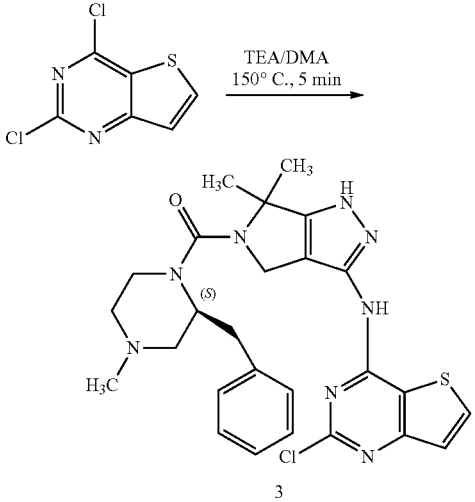

3

Preparation of 3a: ethyl 3-amino-5-(chlorocarbonyl)-6,6-dimethyl-5,6-dihydropyrrolo[3,4-c]pyrazole-2(4H)-carboxylate To a stirring mixture of 5-tert-butyl 2-ethyl 3-amino-6,6-dimethylpyrrolo[3,4-c]pyrazole-2,5(4H,6H)-dicarboxylate (5.65 g, 17.4 mmol) in CH$_2$Cl$_2$ (20 ml) was added 4.0M HCl in dioxane (30 ml). The resulting mixture was stirred at room temperature for 2 h. After the reaction mixture was concentrated in vacuo, a portion of residue (1.53 g, 5.15 mmol) was dissolved into a solution of DIPEA (3.6 ml, 4 eq) in CH$_2$Cl$_2$ (10 ml). The resulting solution was slowly added to a solution of triphosgene (628 mg, 0.41 eq) in CH$_2$Cl$_2$ (10 ml) at 0° C. and the resulting mixture was stirred at 0° C. for 1 h. The reaction mixture was diluted with ethyl acetate and washed with saturated NaHCO$_3$, dried over sodium sulfate. The organic layer was filtered and evaporated in vacuo to give a residue, compound 3a. Compound 3a was directly carried onto the next reaction without further purification.

Preparation of 3b: 5-{[(2S)-2-benzyl-4-methylpiperazin-1-yl]carbonyl}-6,6-dimethyl-1,4,5,6-tetrahydropyrrolo[3,4-c]pyrazol-3-amine A portion of above residue (525 mg) was added into a solution of (3S)-3-benzyl-1-methylpiperazine (552 mg, 1.5 eq) in CH$_2$Cl$_2$ (4 ml). The resulting mixture was stirred at reflux for 4 h. The reaction mixture was then cooled to room temperature, and the solvent was removed in vaccuo. To the residue was added 2N LiOH (3 ml) and methanol (2 ml). The resulting mixture was stirred at reflux for 4 hours. The reaction mixture was purified by prep-HPLC to provide compound 3b as a white solid (150 mg). To a stirring solution of compound 3b (0.15, 0.41 mmol) in NMP (1 mL) was added 2,4-dichlorothieno[3,2-d]pyrimidine (0.084 g, 1 eq) and triethylamine (0.11 ml, 2 eq). The resulting mixture was heated to 140° C. for 5 minutes in microwave reactor. The reaction mixture was purified by prep-HPLC to provide compound 3 as a white solid (0.014 g, 15%). $^1$H NMR (CD$_3$OD) δ: 1.58 (s, 3H), 1.66 (s, 3H), 2.22 (s, 3H), 2.38 (m, 2H), 2.45 (m, 1H), 2.60 (m, 1H), 2.78 (dd, J=13.26, 8.21 Hz, 1H), 2.99 (dd, J=13.52, 6.44 Hz, 1H), 3.15 (s, 1H), 3.35 (m, 1H), 3.75 (m, 1H), 4.28 (d, J=11.12, 1H), 4.65 (m, 1H), 6.99 (t, J=7.01, 1H), 7.08 (t, J=7.58 Hz, 2H) 7.10-7.13 (m, 2H) 7.27 (d, J=5.31 Hz, 1H) 8.07 (d, J=5.31 Hz, 1H). Anal. (C$_{26}$H$_{29}$N$_8$OSCl.0.5HOAc.0.5H$_2$O) C, H, N. HPLC: >95% purity.

Example 4

3-[(2,6-dichloropyrimidin-4-yl)amino]-6,6-dimethyl-N-[trans-2-phenyl cyclopropyl]-4,6-dihydropyrrolo[3,4-c]pyrazole-5(1H)-carboxamide

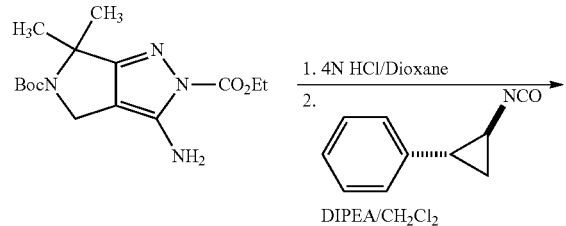

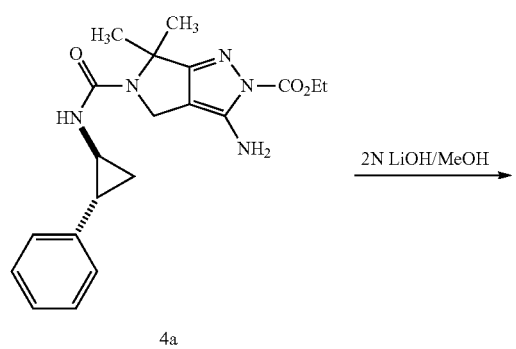

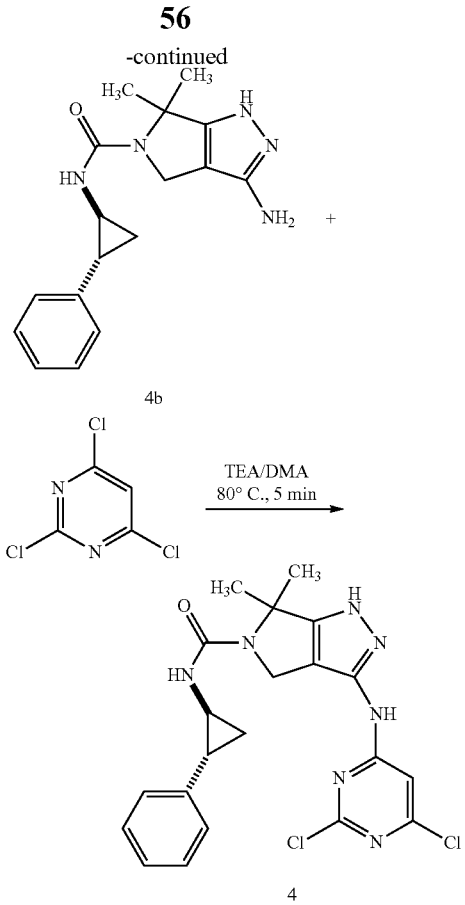

Preparation of Compound 4a: ethyl-3-amino-6,6-dimethyl-5-({[trans-2-phenyl cyclopropyl]amino}carbonyl)-5,6-dihydropyrrolo[3,4-c]pyrazole-2(4H)-carboxylate To a stirring mixture of 5-tert-butyl 2-ethyl 3-amino-6,6-dimethylpyrrolo[3,4-c]pyrazole-2,5(4H,6H)-dicarboxylate (5.65 g, 17.4 mmol) in CH$_2$Cl$_2$ (20 ml) was added 4.0M HCl in dioxane (30 ml). After the reaction mixture was concentrated in vacuo, a portion of residue (3.45 g, 11.6 mmol) was dissolved into a solution of DIPEA (8.1 ml, 4 eq) in CH$_2$Cl$_2$ (50 ml). To the resulting solution was slowly added to trans-2-phenylcyclopropyl isocyanate at 0° C. and the resulting mixture was stirred at 0° C. for 30 minutes then warmed up and stirred at room temperature for 1 h. The reaction mixture was diluted with CH$_2$Cl$_2$, and washed with saturated NaHCO$_3$, dried over sodium sulfate, concentrated in vacuo, purified by flash chromatography. Elution with 60-80% EtOAc/hexane provided the compound 4a as a white solid (4.24 g, 95%). $^1$H NMR (CD$_3$OD) δ: 1.03-1.16 (m, 2H) 1.60 (d, J=3.79 Hz, 6H) 1.98 (s, 1H) 2.71 (s, 1H) 4.12 (s, 1H) 7.01-7.10 (m, 3H) 7.13-7.21 (m, 2H)

Preparation of Compound 4b: 3-amino-6,6-dimethyl-N-[trans-2-phenylcyclopropyl]-4,6-dihydropyrrolo[3,4-c]pyrazole-5(1H)-carboxamide To a stirring solution of ethyl 3-amino-6,6-dimethyl-5-({[trans-2-phenylcyclopropyl]amino}carbonyl)-5,6-dihydropyrrolo[3,4-c]pyrazole-2(4H)-carboxylate (613 mg, 1.60 mmol) in MeOH (3 mL) was added 2N LiOH (1 ml, 1.25 eq).

The resulting mixture was stirred under reflux for 4 hours, cooled, and concentrated. The residue was partitioned between ethyl acetate and saturated NaHCO$_3$, dried, and concentrated to give compound 4b as a white solid (0.42 g, 79%). $^1$H NMR (CD$_3$OD) δ: 1.03-1.16 (m, 2H) 1.60 (d, J=3.79 Hz, 6H) 1.98 (s, 1H) 2.71 (s, 1H) 4.12 (s, 2H) 7.01-7.10 (m, 3H) 7.13-7.21 (m, 2H).

To a stirring solution of compound 4b (0.10 g, 0.32 mmol) in DMA (0.5 mL) was added 2,4,6-trichloropyrimidine (0.041 ml, 1.1 eq) and triethylamine (0.089 ml, 2 eq). The resulting mixture was heated to a temperature of 80° C. for 5 minutes in microwave reactor. The reaction mixture was purified by prep-HPLC to provide the compound 4 as a white solid (0.025 g, 17 $^1$H NMR (CD$_3$OD) δ: 1.05-1.11 (m, 2H), 1.66 (d, J=3.54 Hz, 6H), 1.95 (m, 1H), 2.68-2.72 (m, 1H), 4.42 (b, 2H), 7.05 (d, J=7.83 Hz, 4H), 7.15 (t, J=7.58 Hz, 2H). Anal. (C$_{21}$H$_{21}$N$_7$OCl$_2$.0.4HOAc.0.2H$_2$O) C, H, N. HPLC: >95% purity.

| Structure and Example # | Chemical name, Analytical data and comments |
|---|---|
| 5 | 5  N-[(1S)-2-(dimethylamino)-1-phenylethyl]-6,6-dimethyl-3-(thieno[3,2-d]pyrimidin-4-ylamino)-4,6-dihydropyrrolo[3,4-c]pyrazole-5(1H)-carboxamide. $^1$H NMR (400 MHz, CD$_3$OD) δ: 1.63 (s, 3 H), 1.70 (s, 3 H), 2.38 (s, 6 H), 2.54 (dd, J = 12.63, 4.55 Hz, 1 H), 2.80-2.95 (m, 1 H), 4.45-4.70 (m, 2 H), 4.94-5.08 (m, 1 H), 7.09-7.41 (m, 6 H), 7.95-8.09 (m, 1 H), 8.59 (s, 1 H). Anal. (C$_{24}$H$_{28}$N$_8$OS•0.75 HOAc) C, H, N. Method of Example 1. [(2S)-2-isocyanato-2-phenyl ethyl] dimethylamine was used in place of trans-2-phenylcyclopropyl isocyanate. |
| 6 | 6  3-[(2-chlorothieno[3,2-d]pyrimidin-4-yl)amino]-N-[(1S)-2-(dimethylamino)-1-phenylethyl]-6,6-dimethyl-4,6-dihydropyrrolo[3,4-c]pyrazole-5(1H)-carboxamide. $^1$H NMR (400 MHz, CD$_3$OD) δ: 1.62 (s, 3 H), 1.68 (s, 3 H), 2.38 (s, 6 H), 2.56-2.66 (m, 1 H), 2.79-2.89 (m, 1 H), 4.69-4.73 (m, 1 H), 4.80-4.85 (m, 1 H), 4.93 (dd, J = 10.2, 4.4 Hz, 1 H), 7.07-7.38 (m, 6 H), 8.05 (d, J = 5.31 Hz, 1 H). Anal. (C$_{24}$H$_{27}$N$_8$OSCl•1.0 HOAc•0.6H$_2$O) C, H, N. Method of Example 2. [(2S)-2-isocyanato-2-phenylethyl] dimethylamine was used in place of trans-2-phenylcyclopropyl isocyanate 2. |
| 7 | 7  3-[(4-chloro-6-propoxy-1,3,5-triazin-2-yl)amino]-6,6-dimethyl-N-[trans-2-phenyl cyclopropyl]-4,6-dihydropyrrolo[3,4-c]pyrazole-5(1H)-carboxamide $^1$H NMR (CD$_3$OD) δ: 0.94 (t, J = 7.33 Hz, 3 H) 1.02-1.13 (m, 2 H) 1.65 (d, J = 3.54 Hz, 6 H) 1.68-1.77 (m, 2 H) 1.90-2.00 (m, 1 H) 2.65-2.73 (m, 1 H) 4.27 (t, J = 6.19 Hz, 2 H) 4.39 (d, J = 23.75 Hz, 2 H) 6.99-7.08 (m, 3 H) 7.10-7.19 (m, 2 H). Anal. (C$_{23}$H$_{27}$N$_8$O$_2$Cl•0.2HOAc•0.6H$_2$O) C, H, N. Method of Example 4. 2,4-dichloro-6-propoxy-1,3,5 triazine was used in place of 2,4,6-trichloropyrimidine while the reaction mixture was heated to 120° C. |
| 8 | 8  3-[(4-amino-6-chloro-1,3,5-triazin-2-yl)amino]-6,6-dimethyl-N-[trans-2-phenylcyclopropyl]-4,6-dihydropyrrolo[3,4-c]pyrazole-5(1H)-carboxamide. $^1$H NMR (CD$_3$OD) δ: 1.02-1.16 (m, 2 H) 1.58-1.69 (m, 4 H) 1.88 (d, J = 4.04 Hz, 2 H) 1.91-2.01 (m, 1 H) 2.63-2.75 (m, 1 H) 4.12 (d, 1 H) 4.36 (b, 1 H) 6.98-7.09 (m, 3 H) 7.10-7.20 (m, 2 H). Anal. (C$_{20}$H$_{22}$N$_9$OCl•0.3HOAc•1.1H$_2$O)C, H, N. Method of example 4. 2,4-dichloro-6-amino-1,3,5-triazine was used in place 2,4,6-trichloropyrimidine and the reaction mixture was heated to 120° C. |

| Structure and Example # | Chemical name, Analytical data and comments |
| --- | --- |
| 9 | 9 3-[(4,6-dichloro-1,3,5-triazin-2-yl)amino]-6,6-dimethyl-N-[trans-2-phenylcyclopropyl]-4,6-dihydropyrrolo[3,4-c]pyrazole-5(1H)-carboxamide.<br>$^1$H NMR (CD$_3$OD) δ: 1.02-1.14 (m, 2 H) 1.66 (d, J = 3.54 Hz, 6 H) 1.91-1.99 (m, 1 H) 2.65-2.74 (m, 1 H) 4.44 (s, 2 H) 7.00-7.08 (m, 3 H) 7.10-7.18 (m, 2 H). Anal. (C$_{20}$H$_{20}$N$_8$OCl$_2$•0.1HOAc•0.4H$_2$O) C, H, N.<br>Method of example 4. 2,4,6- trichloro-1,3,5-triazine was used in place of 2,4,6-trichloropyrimidine and the reaction mixture was stirred at room temperature overnight. |
| 10 | 10 3-[(4-chloro-6-methoxy-1,3,5-triazin-2-yl)amino]-6,6-dimethyl-N-[trans-2-phenylcyclopropyl]-4,6-dihydropyrrolo[3,4-c]pyrazole-5(1H)-carboxamide.<br>$^1$H NMR (CD$_3$OD) δ: 1.02-1.16 (m, 2 H) 1.66 (d, J = 3.54 Hz, 6 H) 1.92-1.99 (m, 1 H) 2.70 (b, 1 H) 3.92 (s, 3 H) 4.38 (d, J = 33.85 Hz, 2 H) 6.99-7.09 (m, 3 H) 7.11-7.19 (m, 2 H). Anal. (C$_{21}$H$_{23}$N$_8$O$_2$Cl•0.1 HOAc•0.3H$_2$O) C, H, N.<br>Method of example 4. 2,4-dichloro-6-methoxy-1,3,5-triazine was used in place of 2,4,6-trichloropyrimidine and the reaction mixture was stirred at room temperature for 1 hr. |
| 11 | 11 6,6-dimethyl-3-{[2-(methylthio)-6-(trifluoromethyl)pyrimidin-4-yl]amino}-N-[trans-2-phenylcyclopropyl]-4,6-dihydropyrrolo[3,4-c]pyrazole-5(1H)-carboxamide.<br>$^1$H NMR (400 MHz, DMSO-d$_6$) δ ppm 1.00-1.09 (m, 1 H) 1.14-1.21 (m, 1 H) 1.63 (d, J = 1.52 Hz, 6 H) 1.87-1.94 (m, 1 H) 2.69-2.79 (m, 1 H) 3.32 (s, 3 H) 4.34 (s, 2 H) 6.12 (s, 1 H) 6.81 (s, 1 H) 7.07-7.17 (m, 3 H) 7.24 (t, J = 7.58 Hz, 2 H) 10.52 (s, 1 H). Anal. (C$_{23}$H$_{24}$N$_7$OSF$_3$•0.6H$_2$O) C, H, N.<br>Method of Example 4. 4-chloro-2-(methylthio)-6-(trifluoromethyl) pyrimidine was used in place of 2,4,6-trichloropyrimidine while the reaction mixture was stirred at 100° C. for 10 minutes in microwave reactor. |
| 12 | 12 3-[(2-chloroquinazolin-4-yl)amino]-6,6-dimethyl-N-[(trans-2-phenylcyclopropyl]-4,6-dihydropyrrolo[3,4-c]pyrazole-5(1H)-carboxamide.<br>$^1$H NMR (CD$_3$OD) δ: 1.04-1.15 (m, 2 H) 1.70 (d, J = 3.28 Hz, 6 H) 1.92-2.00 (m, 1 H) 2.67-2.77 (m, 1 H) 4.56 (s, 2 H) 6.08 (s, 1 H) 7.00-7.09 (m, 3 H) 7.10-7.19 (m, 2 H) 7.54 (t, J = 7.45 Hz, 1 H) 7.64 (d, J = 8.34 Hz, 1 H) 7.79 (t, J = 7.33 Hz, 1 H) 8.26 (d, J = 8.08 Hz, 1 H). Anal. (C$_{25}$H$_{24}$N$_7$OCl•0.2HOAc•0.5H$_2$O) C, H, N.<br>Method of Example 4. 2,4-dichloroquinazoline was used in place of 2,4,6-trichloropyrimidine while the reaction mixture was stirred at 160° C. for 10 minutes in a microwave reactor. |

Example 13

3-({4-[(2S)-2-(aminocarbonyl)pyrrolidin-1-yl]-6-chloro-1,3,5-triazin-2-yl}amino)-6,6-dimethyl-N-[trans-2-phenylcyclopropyl]-4,6-dihydropyrrolo[3,4-c]pyrazole-5(1H)-carboxamide

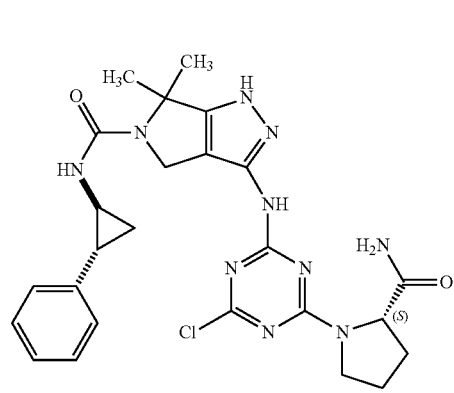

13

To a stirring mixture of Compound 9 (0.039 g, 0.085 mmol) and DIEPA (0.030 ml, 2 eq) in THF (1 ml) was added L-prolinamide (9.7 mg, 1 eq). The resulting mixture was stirred at room temperature for 1 hr and purified by prep-HPLC to provide the compound 13 as a white solid (23 mg). $^1$H NMR (CD$_3$OD) δ: 1.01-1.16 (m, 2H) 1.57-1.71 (m, 6H) 1.88-2.09 (m, 4H) 2.12-2.35 (m, 1H) 2.65-2.76 (m, 1H) 3.50-3.78 (m, 2H) 4.27-4.53 (m, 3H) 6.99-7.08 (m, 3H) 7.10-7.19 (m, 2H). Anal. (C$_{26}$H$_{29}$N$_{10}$O$_2$Cl.0.4HOAc.1.3H$_2$O) C, H, N. HPLC: >95% purity.

Example 14

3-[(4,6-dimethoxy-1,3,5-triazin-2-yl)amino]-6,6-dimethyl-N-[trans-2-phenyl cyclopropyl]-4,6-dihydropyrrolo[3,4-c]pyrazole-5(1H)-carboxamide

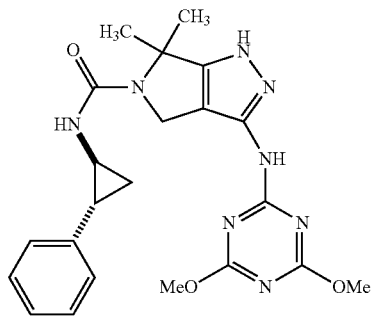

14

To a stirring solution of compound 4b (0.150 g, 0.48 mmol) in DMA (1 mL) was added 2,4,6-trichlorotriazene (98 mg, 1.1 eq) and DIPEA (0.168 ml, 2 eq). The resulting mixture was stirred at room temperature for 1 hr. To the reaction mixture was added 25% NaOMe in methanol (0.549 ml, 5 eq). The resulting mixture was stirred at room temperature for 2 hours and purified by prep-HPLC to provide compound 14 as a white solid (45 mg). $^1$H NMR (CD$_3$OD) δ: 1.02-1.14 (m, 2H) 1.65 (d, J=3.79 Hz, 6H) 1.91-1.99 (m, 1H) 2.64-2.72 (m, 1H) 3.89 (s, 6H) 4.32 (s, 2H) 6.99-7.08 (m, 3H) 7.09-7.18 (m, 2H). Anal. (C$_{22}$H$_{26}$N$_8$O$_3$.0.2HOAc.0.6H$_2$O) C, H, N. HPLC: >95% purity.

| Structure and Example # | Chemical name, Analytical data and Comments |
|---|---|
| 15 | 3-{[4-chloro-6-(dimethylamino)-1,3,5-triazin-2-yl]amino}-6,6-dimethyl-N-[trans-2-phenyl cyclopropyl]-4,6-dihydropyrrolo[3,4-c]pyrazole-5(1H)-carboxamide. $^1$H NMR (CD$_3$OD) δ: 1.02-1.15 (m, 2 H) 1.64 (d, J = 3.79 Hz, 6 H) 1.91-1.98 (m, 1 H) 2.65-2.74 (m, 1 H) 3.07 (s, 6 H) 4.33 (s, 2 H) 7.00-7.09 (m, 3 H) 7.10-7.18 (m, 2 H). Anal. (C$_{22}$H$_{26}$N$_9$OCl•0.2HOAc•0.1H$_2$O) C, H, N. Method of Example 14, DMA was used in place of NaOMe. |

Example 16

3-({4-[(2S)-2-(hydroxymethyl)pyrrolidin-1-yl]-6-methoxy-1,3,5-triazin-2-yl}amino)-6,6-dimethyl-N-[trans-2-phenylcyclopropyl]-4,6-dihydropyrrolo[3,4-c]pyrazole-5(1H)-carboxamide

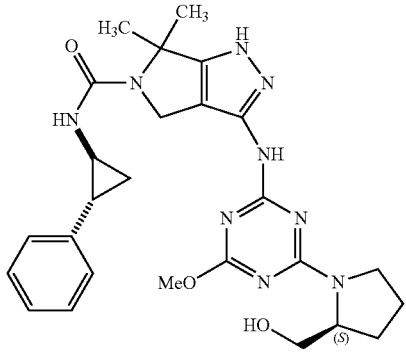

To a stirring solution of compound 4b (0.152 g, 0.488 mmol) in DMA (2 mL) was added 2,4-dichloro-6-methoxy-1,3,5-triazine (92 mg, 1.05 eq) and DIPEA (0.170 ml, 2 eq). The resulting mixture was stirred at room temperature for 1 hr. To the reaction mixture was added pyrrolidin-2-ylmethanol (0.072 ml, 1.5 eq). The resulting mixture was stirred at room temperature for 1 hr and purified by prep-HPLC to provide compound 16 as a white solid (64.9 mg). $^1$H NMR (CD$_3$OD) δ: 1.02-1.14 (m, 2H) 1.63 (d, J=3.54 Hz, 6H) 1.84 (b, 1H) 1.90-2.00 (m, 4H) 2.66-2.74 (m, 1H) 3.48-3.71 (m, 4H) 3.84 (s, 3H) 4.10-4.22 (m, 1H) 4.28 (s, 2H) 7.00-7.08 (m, 3H) 7.11-7.18 (m, 2H). Anal. (C$_{26}$H$_{33}$N$_9$O$_3$·0.1HOAc·0.7H$_2$O) C, H, N. HPLC: >95% purity.

| Structure and Example # | Chemical name, Analytical data and comments |
|---|---|
| 17 | 3-[(4-methoxy-6-{(2S)-2-[(methylamino)carbonyl]pyrrolidin-1-yl}-1,3,5-triazin-2-yl)amino)-6,6-dimethyl-N-[(trans-2-phenylcyclopropyl)]-4,6-dihydropyrrolo[3,4-c]pyrazole-5(1H)-carboxamide.<br>$^1$H NMR (CD$_3$OD) δ: 1.03-1.16 (m, 2 H) 1.64 (d, J = 3.79 Hz, 6 H) 1.89-2.04 (m, 4 H) 2.14-2.28 (m, 1 H) 2.58-2.67 (m, 3 H) 2.71 (s, 1 H) 3.54-3.74 (m, 2 H) 3.82 (d, J = 37.14 Hz, 3 H) 4.26 (d, J = 21.73 Hz, 2 H) 4.36-4.48 (m, 1 H) 7.01-7.09 (m, 3 H) 7.11-7.19 (m, 2 H). Anal. (C$_{27}$H$_{34}$N$_{10}$O$_3$·0.2HOAc·0.9H$_2$O) C, H, N.<br>Method of Example 16 using N-methyl-L-prolinamide in place of pyrrolidin-2-ylmethanol. |
| 18 | 3-{[4-methoxy-6-(2-methylaziridin-1-yl)-1,3,5-triazin-2-yl]amino}-6,6-dimethyl-N-[trans-2-phenylcyclopropyl]-4,6-dihydropyrrolo[3,4-c]pyrazole-5(1H)-carboxamide.<br>$^1$H NMR (CD$_3$OD) δ: 1.04-1.14 (m, 5 H) 1.64 (d, J = 3.79 Hz, 6 H) 1.93-2.01 (m, 1 H) 2.66-2.75 (m, 1 H) 3.26-3.46 (m, 2 H) 3.79-3.89 (m, 4 H) 4.30 (s, 2 H) 6.99-7.09 (m, 3 H) 7.15 (t, J = 7.45 Hz, 2 H). Anal. (C$_{24}$H$_{29}$N$_9$O$_2$·0.2HOAC·1.6H$_2$O) C, H, N.<br>Method of Example 16 using 2-methylaziridine instead of pyrrolidin-2-ylmethanol |

| Structure and Example # | Chemical name, Analytical data and comments |
|---|---|
| 19 | 3-[(4-methoxy-6-pyrrolidin-1-yl-1,3,5-triazin-2-yl) amino]-6,6-dimethyl-N-[trans-2-phenylcyclopropyl]-4,6-dihydropyrrolo[3,4-c]pyrazole-5(1H)-carboxamide.<br>$^1$H NMR (CD$_3$OD) δ: 1.03-1.14 (m, 2 H) 1.64 (d, J = 3.79 Hz, 6 H) 1.88-2.00 (m, 5 H) 2.65-2.74 (m, 1 H) 3.43-3.56 (m, 4 H) 3.84 (s, 3 H) 4.28 (s, 2 H) 6.99-7.10 (m, 3 H) 7.10-7.19 (m, 2 H). Anal. (C$_{25}$H$_{31}$N$_9$O$_2$•0.2HOAc•0.6H$_2$O) C, H, N.<br>Method of Example 16. Pyrrolidine was used in place of pyrrolidin-2-ylmethanol. |
| 20 | 3-({4-[(2S)-2-cyanopyrrolidin-1-yl]-6-methoxy-1,3,5-triazin-2-yl}amino)-6,6-dimethyl-N-[trans-2-phenylcyclopropyl]-4,6-dihydropyrrolo[3,4-c]pyrazole-5(1H)-carboxamide.<br>$^1$H NMR (CD$_3$OD) δ: 1.02-1.15 (m, 2 H) 1.64 (d, J = 3.54 Hz, 6 H) 1.91-2.01 (m, 1 H) 2.01-2.14 (m, 2 H) 2.21-2.80 (m, 2 H) 2.65-2.73 (m, 1 H) 3.46-3.57 (m, 1 H) 3.62-3.72 (m, 1 H) 3.89 (d, J = 13.39 Hz, 3 H) 4.30 (s, 2 H) 4.87 (t, J = 5.18 Hz, 1 H) 7.00-7.08 (m, 3 H) 7.11-7.19 (m, 2 H). Anal. (C$_{26}$H$_{30}$N$_{10}$O$_2$•0.3HOAc•0.1H$_2$O) C, H, N.<br>Method of Example 16. (2S)-pyrrolidine-2-carbonitrile was used in place of pyrrolidin-2-ylmethanol. |
| 21 | 3-({4-[(2S)-2-(amino carbonyl)pyrrolidin-1-yl]-6-methoxy-1,3,5-triazin-2-yl}amino)-6,6-dimethyl-N-[trans-2-phenylcyclopropyl]-4,6-dihydropyrrolo[3,4-c]pyrazole-5(1H)-carboxamide.<br>$^1$H NMR (CD$_3$OD) δ: 1.02-1.16 (m, 2 H) 1.63 (s, 6 H) 1.90-2.08 (m, 4 H) 2.25 (s, 1 H) 2.71 (s, 1 H) 3.56-3.75 (m, 2 H) 3.84 (d, J = 21.73 Hz, 3 H) 4.21-4.37 (m, 2 H) 4.44 (d, J = 9.09 Hz, 1 H) 7.00-7.08 (m, 3 H) 7.10-7.19 (m, 2 H). Anal. (C$_{26}$H$_{32}$N$_{10}$O$_3$•0.2HOAc•0.9H$_2$O) C, H, N.<br>Method of Example 16 using L-prolinamide (2eq) instead of pyrrolidin-2-ylmethanol. |

Example 22

3-{[4-[(2S)-2-(aminocarbonyl)pyrrolidin-1-yl]-6-(dimethylamino)-1,3,5-triazin-2-yl]amino}-6,6-dimethyl-N-[(trans-2-phenylcyclopropyl]-4,6-dihydropyrrolo[3,4-c]pyrazole-5(1H)-carboxamide

Example 24

3-[(4,6-dimethylpyrimidin-2-yl)amino]-6,6-dimethyl-N-[(trans-2-phenyl cyclopropyl]-4,6-dihydropyrrolo[3,4-c]pyrazole-5(1H)-carboxamide

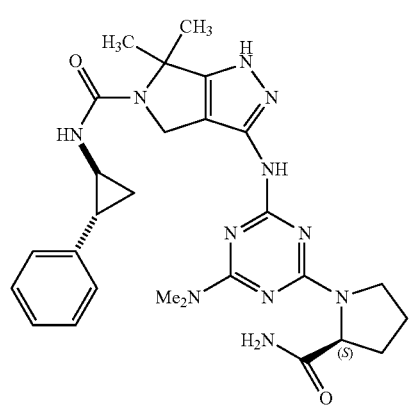

22

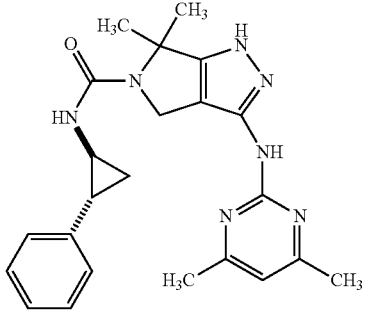

24

To a stirring solution of compound 4b (0.103 g, 0.33 mmol) in DMA (1 mL) was added 2,4,6-trichloropyrimidine (55 mg, 0.9 eq) and DIPEA (0.115 ml, 2 eq). The resulting mixture was stirred at room temperature for 1 hr. To the reaction mixture was added L-prolinamide (34 mg, 0.9 eq). After the resulting mixture was stirred at room temperature for 2 hours, 2N dimethylamine (0.330 ml, 2 eq) was added into reaction mixture. The resulting mixture was stirred at 60° C. for 1 hour and purified by prep-HPLC to provide compound 22 as a white solid (74.8 mg). $^1$H NMR (CD$_3$OD) δ: 1.04-1.17 (m, 2H) 1.62 (d, J=3.28 Hz, 6H) 1.92 (m, 4H) 2.22 (s, 1H) 2.67-2.76 (m, 1H) 3.03 (d, 6H) 3.55-3.75 (m, 2H) 4.21 (d, J=14.15 Hz, 2H) 4.35-4.43 (m, 1H) 7.01-7.09 (m, 3H) 7.11-7.19 (m, 2H). Anal. (C$_{27}$H$_{35}$N$_{11}$O$_2$·0.3HOAc·1.0H$_2$O) C, H, N. HPLC: >95% purity.

A re-sealable tube was charged with compound 4b (0.115 g, 0.30 mmol), 2-chloro-4,6-dimethyl-pyrimidine (0.043 g, 1 eq), Pd(OAc)$_2$ (1.3 mg, 0.02 eq), DPPP (5.0 mg, 0.04 eq), CsCO$_3$ (137 mg, 1.4 eq) and DME (1 ml). The tube was capped and carefully subjected to three cycles of evacuation-backfilling with N$_2$. The resulting mixture was stirred at 150° C. for 10 minutes in microwave reactor, filtered, and purified by prep-HPLC to provide compound 24 as a white solid (12 mg). $^1$H NMR (CD$_3$OD) δ: 1.03-1.14 (m, 2H) 1.65 (d, J=3.79 Hz, 6H) 1.92-2.00 (m, 1H) 2.30 (s, 6H) 2.68-2.75 (m, 1H) 4.33 (s, 2H) 6.58 (s, 1H) 7.00-7.09 (m, 3H) 7.11-7.19 (m, 2H). Anal. (C$_{23}$H$_{27}$N$_7$O·0.3HOAc·0.3H$_2$O) C, H, N. HPLC: >95% purity.

| Structure and Example # | Chemical name, Analytical data and comments |
|---|---|
| 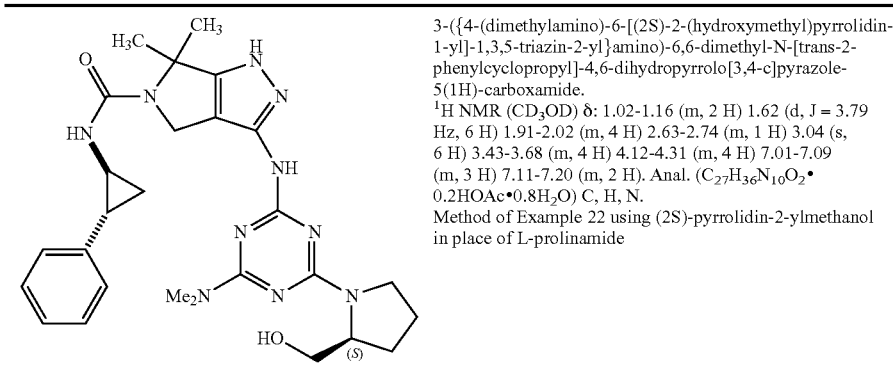<br>23 | 3-({4-(dimethylamino)-6-[(2S)-2-(hydroxymethyl)pyrrolidin-1-yl]-1,3,5-triazin-2-yl}amino)-6,6-dimethyl-N-[trans-2-phenylcyclopropyl]-4,6-dihydropyrrolo[3,4-c]pyrazole-5(1H)-carboxamide.<br>$^1$H NMR (CD$_3$OD) δ: 1.02-1.16 (m, 2 H) 1.62 (d, J = 3.79 Hz, 6 H) 1.91-2.02 (m, 4 H) 2.63-2.74 (m, 1 H) 3.04 (s, 6 H) 3.43-3.68 (m, 4 H) 4.12-4.31 (m, 4 H) 7.01-7.09 (m, 3 H) 7.11-7.20 (m, 2 H). Anal. (C$_{27}$H$_{36}$N$_{10}$O$_2$·0.2HOAc·0.8H$_2$O) C, H, N.<br>Method of Example 22 using (2S)-pyrrolidin-2-ylmethanol in place of L-prolinamide |

| Structure and Example # | Chemical name, Analytical data and comments |
|---|---|
| 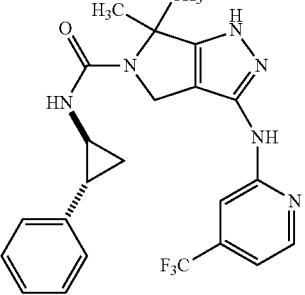<br>25 | 3-[(4-trifluoromethylpyridin-2-yl)amino]-6,6-dimethyl-N-[trans-2-phenylcyclopropyl]-4,6-dihydropyrrolo[3,4-c]pyrazole-5(1H)-carboxamide.<br>$^1$H NMR (CD$_3$OD) δ: 1.01-1.17 (m, 2 H) 1.65 (d, J = 3.79 Hz, 6 H) 1.93-2.01 (m, 1 H) 2.64-2.74 (m, 1 H) 4.35 (s, 2 H) 6.90 (d, J = 5.31 Hz, 1 H) 6.98 (s, 1 H) 7.00-7.09 (m, 3 H) 7.10-7.18 (m, 2 H) 8.32 (d, J = 5.31 Hz, 1 H). Anal. (C$_{23}$H$_{23}$N$_6$OF$_3$•0.1HOAc•0.4H$_2$O) C, H, N.<br>Method of Example 24. 4,5-bis (diphenylphosphino)-9,9-dimethylxanthene was used in place of DPPP and 2-chloro-4-trifluoromethyl-pyridine was used in place of 2-chloro-4,6-dimethyl-pyrimidine. |
| 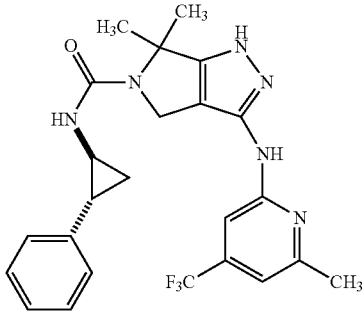<br>26 | 3-[(4-trifluoromethyl-6-methylpyridin-2-yl)amino]-6,6-dimethyl-N-[trans-2-phenylcyclopropyl]-4,6-dihydropyrrolo[3,4-c]pyrazole-5(1H)-carboxamide.<br>$^1$H NMR (CD$_3$OD) δ: 1.02-1.14 (m, 2 H) 1.65 (d, J = 3.54 Hz, 6 H) 1.90-2.00 (m, 1 H) 2.45 (s, 3 H) 2.66-2.73 (m, 1 H) 4.34 (s, 2 H) 6.79 (s, 2 H) 6.99-7.09 (m, 3 H) 7.10-7.18 (m, 2 H). Anal. (C$_{24}$H$_{25}$N$_6$OF$_3$•0.2HOAc•0.1H$_2$O) C, H, N.<br>Method of Example 24. 4,5-bis (diphenylphosphino)-9,9-dimethylxanthene was used in place of DPPP and 2-chloro-4-trifluoromethyl-6-methylpyridine was used in place of 2-chloro-4,6-dimethyl-pyrimidine. |
| 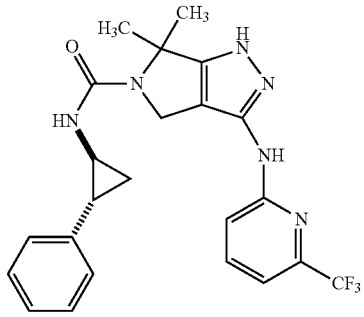<br>27 | 3-[(6-trifluoromethylpyridin-2-yl)amino]-6,6-dimethyl-N-[trans-2-phenylcyclopropyl]-4,6-dihydropyrrolo[3,4-c]pyrazole-5(1H)-carboxamide.<br>$^1$H NMR (CD$_3$OD) δ: 1.05-1.13 (m, 2 H) 1.65 (d, J = 3.79 Hz, 6 H) 1.89-1.98 (m, 1 H) 2.67-2.76 (m, 1 H) 4.40 (s, 2 H) 6.96 (d, J = 8.08 Hz, 1 H) 7.01-7.11 (m, 4 H) 7.11-7.19 (m, 2 H) 7.66 (t, J = 7.45 Hz, 1 H). Anal. (C$_{23}$H$_{23}$N$_6$OF$_3$•0.1HOAc•0.3H$_2$O) C, H, N.<br>Method of Example 24. 4,5-bis (diphenylphosphino)-9,9-dimethylxanthene was used in place of DPPP and 2-chloro-6-trifluoromethylpyridine was used in place of 2-chloro-4,6-dimethyl-pyrimidine. |
| 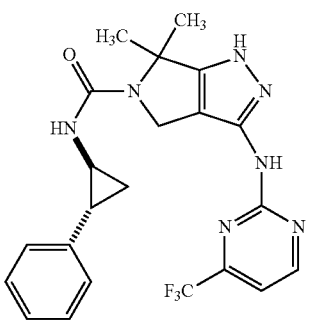<br>28 | 6,6-dimethyl-N-[trans-2-phenylcyclopropyl]-3-{[4-(trifluoromethyl)pyrimidin-2-yl]amino}-4,6-dihydropyrrolo[3,4-c]pyrazole-5(1H)-carboxamide.<br>$^1$H NMR (CD$_3$OD) δ: 1.03-1.15 (m, 2 H) 1.65 (d, J = 3.54 Hz, 6 H) 1.93-2.00 (m, 1 H) 2.67-2.76 (m, 1 H) 4.40 (b, 2 H) 6.98-7.11 (m, 4 H) 7.12-7.19 (m, 2 H) 8.67 (b, 1 H). Anal. (C$_{22}$H$_{22}$N$_7$OF$_3$•0.1 H$_2$O) C, H, N.<br>Method of Example 24. 2-chloro-4-trifluoromethyl-pyrimidine was used in place of 2-chloro-4,6-dimethyl-pyrimidine. |

| Structure and Example # | Chemical name, Analytical data and comments |
|---|---|
| 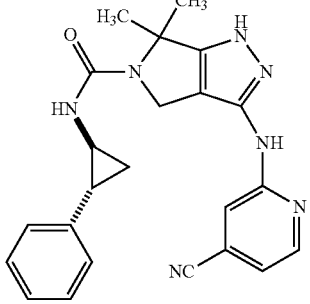<br>29 | 3-[(4-cyanopyridin-2-yl)amino]-6,6-dimethyl-N-[trans-2-phenylcyclopropyl]-4,6-dihydropyrrolo[3,4-c]pyrazole-5(1H)-carboxamide.<br>$^1$H NMR (CD$_3$OD) δ: 1.02-1.15 (m, 2 H) 1.65 (d, J = 3.79 Hz, 6 H) 1.94-2.01 (m, 1 H) 2.66-2.74 (m, 1 H) 4.34 (s, 2 H) 6.91 (d, J = 4.80 Hz, 1 H) 6.99-7.08 (m, 4 H) 7.11-7.19 (m, 2 H) 8.29 (d, J = 5.05 Hz, 1 H). Anal. (C$_{23}$H$_{23}$N$_7$O•0.3HOAc•0.4H$_2$O) C, H, N.<br>Method of Example 24. 4,5-bis (diphenylphosphino)-9,9-dimethylxanthene was used in place of DPPP and 2-chloro-4-cyanopyridine was used in place of 2-chloro-4,6-dimethyl-pyrimidine. |

Example 30

6,6-dimethyl-N-[trans-2-phenylcyclopropyl]-3-{[2-(trifluoromethyl)pyrimidin-4-yl]amino}-4,6-dihydro-pyrrolo[3,4-c]pyrazole-5(1H)-carboxamide

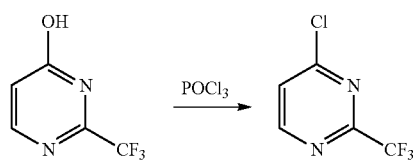
30a

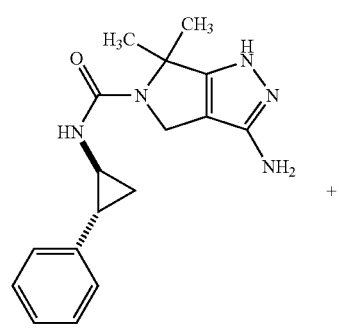
4b

+

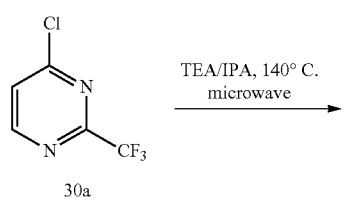
30a

TEA/IPA, 140° C.
microwave
→

-continued

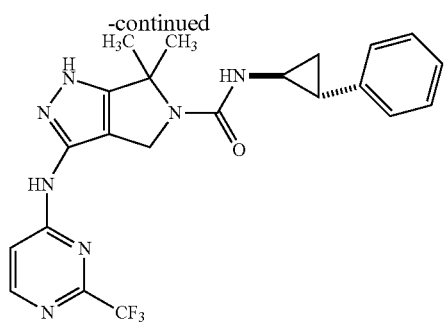
30

Preparation of Compound 30a:
4-chloro-2-(trifluoromethyl)pyrimidine

To 2-(trifluoromethyl)pyrimidin-4-ol (2 g, 12 mmol) was added POCl$_3$ (15 mL). It was refluxed overnight. The solvent was removed. 1N NaOH was added to the reaction mixture slowly until pH=10. The mixture was extracted with DCM (3×80 mL). Combined DCM layer dried over Na$_2$SO$_4$ and taken to dryness. The crude product was vacuum distilled. 4-chloro-2(trifluoromethyl)pyrimidine was obtained as a clear oil. (94%). $^1$H NMR (400 MHz, DCM) δ: 7.60 (d, J=3 Hz, 1H), 8.80 (d, J=3 Hz, 1H), To a mixture of compound 30a (137 mg, 0.75 mmol) and compound 4b (235 mg, 0.75 mmol) in IPA (1 mL), was added TEA (210 mL, 1.5 mmol). The reaction was heated in microwave oven at 140° C. for 20 min. HPLC yielded the desired product as a white powder (28 mg, 6.4%). $^1$H NMR (400 MHz, DMSO) δ: 1.04 (m, 2H), 1.62 (m, 6H), 1.88 (m, 1H), 2.73 (m, 1H), 4.34 (m, 2H), 7.09-7.37 (m, 6H), 8.41 (s, 1H). Anal. (C$_{22}$H$_{22}$N$_7$OF$_3$.0.52TFA.0.54H$_2$O) C, H, N. APCI-MS: [M+H] 458.

Example 31

6,6-dimethyl-3-[(2-methylthieno[2,3-d]pyrimidin-4-yl)amino]-N-[trans-2-phenylcyclopropyl]-4,6-dihydropyrrolo[3,4-c]pyrazole-5(1H)-carboxamide

Example 32

6,6-Dimethyl-3-[(2-methylthieno[3,2-d]pyrimidin-4-yl)amino]-N-[(1R,2S)-2-phenylcyclopropyl]-4,6-dihydropyrrolo[3,4-c]pyrazole-5(1H)-carboxamide

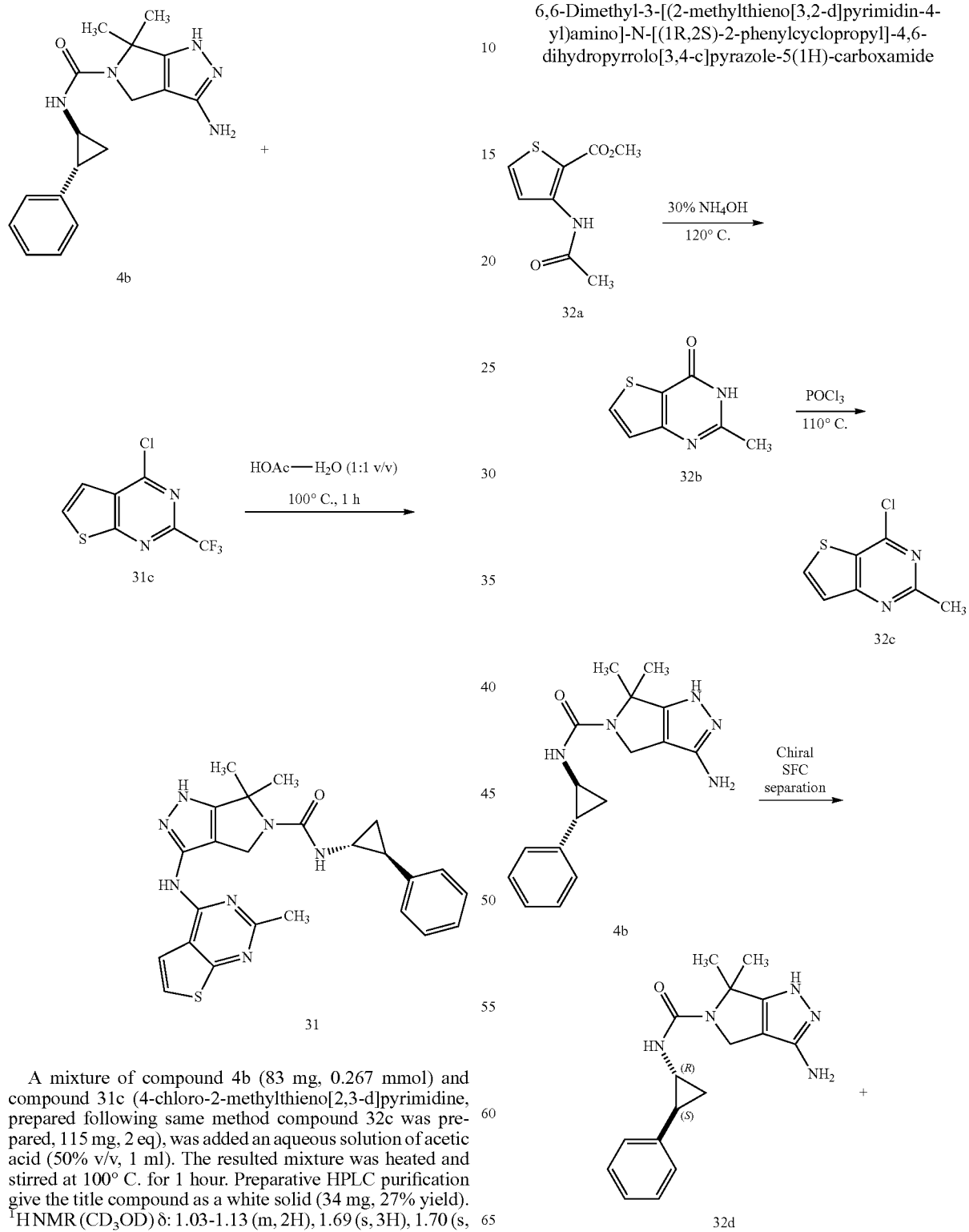

A mixture of compound 4b (83 mg, 0.267 mmol) and compound 31c (4-chloro-2-methylthieno[2,3-d]pyrimidine, prepared following same method compound 32c was prepared, 115 mg, 2 eq), was added an aqueous solution of acetic acid (50% v/v, 1 ml). The resulted mixture was heated and stirred at 100° C. for 1 hour. Preparative HPLC purification give the title compound as a white solid (34 mg, 27% yield). $^1$H NMR (CD$_3$OD) δ: 1.03-1.13 (m, 2H), 1.69 (s, 3H), 1.70 (s, 3H), 1.90-1.99 (m, 1H), 2.66 (s, 3H), 2.67-2.75 (m, 1H), 4.46 (s, 2H), 6.98-7.19 (m, 5H), 7.55-7.61 (m, 1H) 7.63-7.69 (m, 1H), 8.20 (d, J=6.06 Hz, 1H). LCMS (APCI, M+H$^+$): 460.1. Anal. (C$_{24}$H$_{26}$N$_7$OS.1.51TFA.0.15H$_2$O): C, H, N. HPLC-UV Detection: 95% purity.

-continued

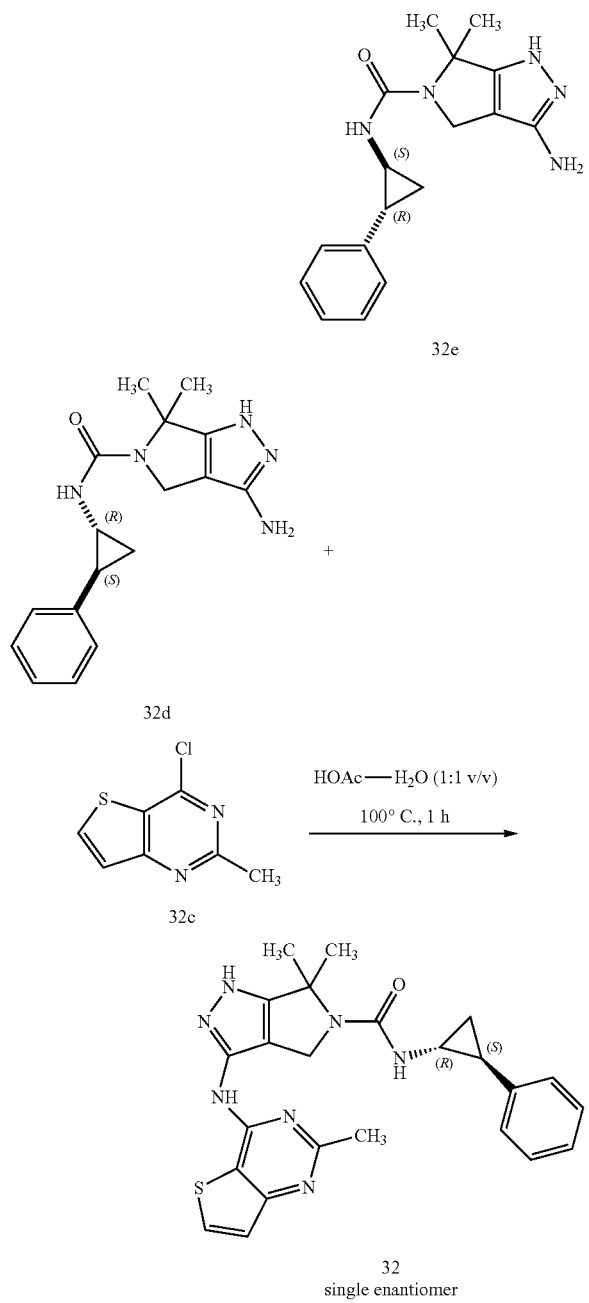

Preparation of Compound 32b:
2-Methylthieno[3,2-d]pyrimidin-4(3H)-one

Methyl 3-(acetylamino)thiophene-2-carboxylate (32a, 3.00 g, 15.08 mmol) was suspended in 30% $NH_4OH$ (43 mL) in a sealed tube. The reaction was stirred at 120° C. for 5 hours and then overnight at ambient temperature. The reaction was brought to pH 8-9 with concentrated HCl. The resulting white precipitate was filtered and washed with water, then dried to give compound 32b (1.56 g, 62%) as a white solid. Compound 32b was used without further purification. $^1$H NMR (400 MHz, DMSO-$d_6$) δ 2.35 (s, 3H), 7.30 (d, J=5.3 Hz, 1H), 8.12 (d, J=5.3 Hz, 1H), 12.38 (s, 1H). LCMS 167 (M+H).

Preparation of Compound 32c:
4-Chloro-2-methylthieno[3,2-d]pyrimidine

2-Methylthieno[3,2-d]pyrimidin-4(3H)-one (compound 32b, 0.18 g, 1.13 mmol) was heated to 110° C. in $POCl_3$ overnight. The solvent was removed under reduced pressure, and the residue was neutralized with saturated $NaHCO_3$ solution. The product was extracted into $CH_2Cl_2$, and the organic phase separated, washed with brine, and dried ($MgSO_4$). After removal of the solvent compound 32c was obtained as a yellow-orange solid (0.21 g, 88%). Compound 32c was used without further purification. $R_f$=0.16 (10% EtOAc/hexane). $^1$H NMR (400 MHz, DMSO-$d_6$): δ 2.71 (s, 3H), 7.66 (d, J=5.6 Hz, 1H), 8.54 (d, J=5.6 Hz, 1H). LCMS 185 (M+H). Anal. ($C_{23}H_{29}N_8OF.0.35H_2O.0.35$ hexane) C, H, N. HPLC>98% purity.

Preparation of Enantiomer 32d (3-amino-6,6-dimethyl-N-((1R,2S)-2-phenylcyclopropyl)pyrrolo[3,4-c]pyrazole-5(1H,4H,6H)-carboxamide) and enantiomer 32e (3-amino-6,6-dimethyl-N-((1S,2R)-2-phenyl cyclopropyl)pyrrolo[3,4-c]pyrazole-5(1H,4H, 6H)-carboxamide)

An enantioseparation purification method was developed for compound 4b using supercritical fluid chromatography (SFC) technology, with supercritical carbon dioxide providing the bulk of the mobile phase. The separation and isolation of enantiomers was carried out on a Berger SFC Multi-Gram™ Purification System (Mettler Toledo AutoChem, Inc.). The preparative chromatography conditions used to separate the enantiomers consisted of a (S,S) Whelk-O 1 (Regis Technologies, Inc.), 10/100 FEC, 250×21.1 mm column as the chiral stationary phase. Column temperature was maintained at 35° C. The mobile phase used was supercritical $CO_2$ with 35% methanol as the modifier, maintained isocratically at a flow rate of 55 mL/min and a constant pressure of 140 bar. Sample was solubilized in methanol, and a column loadability of 50 mg per 1 mL injection was attained, and the total run time for each injection was 7.0 minutes. Retention times for the two enantiomers were 4.3 and 5.8 minutes, respectively. The specific optical rotation, [α]$_D$, for the pure enantiomers was determined to be −126.7° for Enantiomer 32d and +124.4° for Enantiomer 32e

Preparation of Title Compound 32

4-Chloro-2-methylthieno[3,2-d]pyrimidine (0.091 g, 0.49 mmol) and chiral aminopyrazole enantiomer 32d (0.10 g, 0.33 mmol) were mixed in 1:1 HOAc/$H_2O$ (1.40 mL) and heated to 100° C. for 1 hour. The material was then purified directly by preparative HPLC to give title compound 32 as a white solid (0.136 g, 65%). Mp>148° C. (dec). $^1$H NMR (400 MHz, $CH_3OD$): δ 1.15-1.19 (m, 2H), 1.79 (s, 3H), 1.80 (s, 3H), 2.01-2.05 (m, 1H), 2.76-2.78 (m, 1H), 2.80 (s, 3H), 4.50-4.51 (m, 2H), 7.11-7.15 (m, 3H), 7.22-7.25 (m, 2H), 7.46 (d, J=5.5 Hz, 1H), 8.44 (d, J=5.3 Hz, 1H). LCMS 460 (M+H). Anal. ($C_{24}H_{26}N_7OS.1.50$ TFA.0.25$H_2O$) C,H,N. HPLC>99% purity.

| Structure and Example # | Chemical name, Analytical data and comments |
|---|---|
| 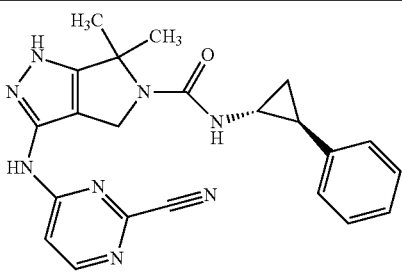<br>33 | 3-[(2-cyanopyrimidin-4-yl)amino]-6,6-dimethyl-N-[trans-2-phenylcyclopropyl]-4,6-dihydropyrrolo[3,4-c]pyrazole-5(1H)-carboxamide<br>$^1$H NMR (CD$_3$OD) δ: 1.03-1.15 (m, 2 H), 1.66 (s, 6 H), 1.75-2.01 (m, 1 H), 2.51-2.75 (m, 1 H), 4.59 (s, 2 H), 6.81-6.96 (b, 1 H), 7.00-7.07 (m, 3 H), 7.10-7.17 (m, 2 H), 8.20 (d, J = 6.06 Hz, 1 H).<br>LCMS (APCI, M + H$^+$): 415.1.<br>HPLC-UV Detection: >95% purity<br>Method of Example 31 using 4-chloropyrimidine-2-carbonitrile in place of 31c. |
| 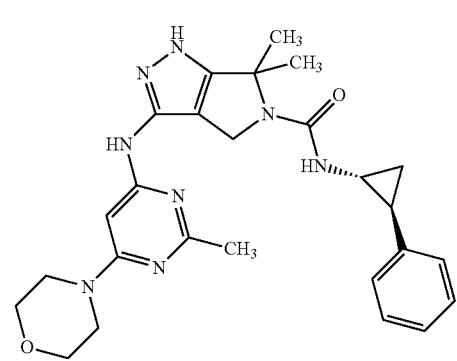<br>34 | 6,6-dimethyl-3-[(2-methyl-6-morpholin-4-ylpyrimidin-4-yl)amino]-N-[trans-2-phenylcyclopropyl]-4,6-dihydropyrrolo[3,4-c]pyrazole-5(1H)-carboxamide<br>$^1$H NMR (400 MHz, DMSO) δ: 1.04-1.21 (m, 2 H), 1.63 (s, 6 H), 2.42 (s, 3 H), 2.75 (m, 1 H), 4.28 (m, 2 H), 6.05 (s, 1 H), 6.31 (m, 1 H) 7.09-7.27(m, 5H).<br>Anal. (C$_{26}$H$_{32}$N$_8$O$_8$•1.6TFA•2.2H$_2$O) C, H, N. APCI-MS: [M + H] 489.<br>Method of Example 31 using 4-chloro-2-methyl-6-morpholinopyrimidine in place of 31c. |
| 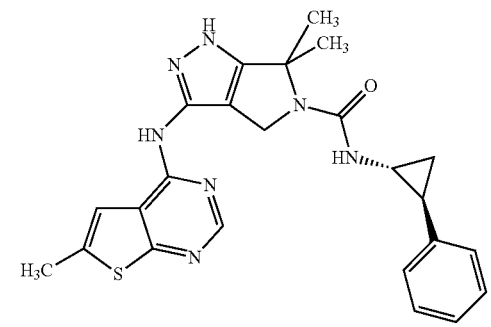<br>35 | 6,6-dimethyl-3-[(6-methylthieno[2,3-d]pyrimidin-4-yl)amino]-N-[trans-2-phenylcyclopropyl]-4,6-dihydropyrrolo[3,4-c]pyrazole-5(1H)-carboxamide<br>$^1$H NMR (CD$_3$OD) δ: 1.04-1.17 (m, 2 H), 1.69 (s, 3 H), 1.70 (s, 3 H), 1.95-2.01 (m, 1 H), 2.57 (s, 3 H), 2.67-2.74 (m, 1 H) 4.45 (s, 2 H), 7.01-7.08 (m, 3 H), 7.11-7.18 (m, 2 H), 7.32 (s, 1 H), 8.52 (s, 1 H).<br>LCMS (APCI, M + H$^+$): 460.3. Anal. (C$_{24}$H$_{25}$N$_7$OS•1.34TFA•0.47H$_2$O): C, H, N.<br>HPLC-UV Detection: 94% purity.<br>Method of Example 31 using 4-chloro-6-methylthieno[2,3-d]pyrimidine in place of 31c. |
| 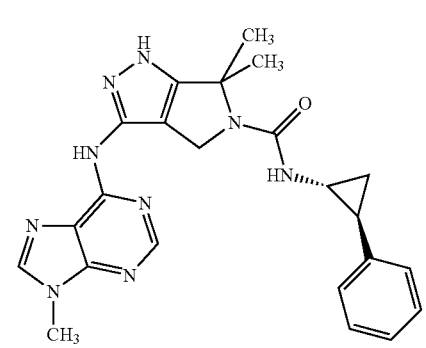<br>36 | 6,6-dimethyl-3-[(9-methyl-9H-purin-6-yl)amino]-N-[trans-2-phenylcyclopropyl]-4,6-dihydropyrrolo[3,4-c]pyrazole-5(1H)-carboxamide<br>$^1$H NMR (CD$_3$OD) δ: 1.01-1.17 (m, 2 H), 1.69 (s, 3 H), 1.70 (s, 3 H), 1.94-2.03 (m, 1 H), 2.65-2.74 (m, 1 H), 3.83 (s, 3 H), 4.43 (s, 2 H), 6.98-7.09 (m, 3 H), 7.11-7.18 (m, 2 H), 8.21 (s, 1 H), 8.53 (s, 1 H).<br>LCMS (APCI, M + H$^+$): 444.2. Anal. (C$_{23}$H$_{25}$N$_9$O•1.15TFA•0.59H$_2$O): C, H, N.<br>HPLC-UV Detection: 90% purity.<br>Method of Example 31 using 6-chloro-9-methyl-9H-purine in place of 31c. |

| Structure and Example # | Chemical name, Analytical data and comments |
|---|---|
| 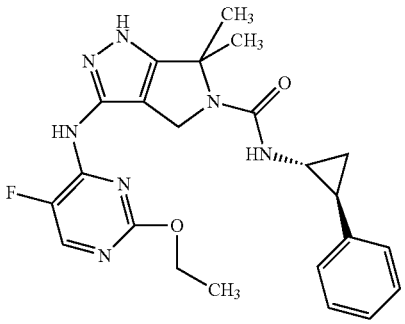<br>37 | 3-[(2-ethoxy-5-fluoropyrimidin-4-yl)amino]-6,6-dimethyl-N-[trans-2-phenylcyclopropyl]-4,6-dihydropyrrolo[3,4-c]pyrazole-5(1H)-carboxamide<br>$^1$H NMR (CD$_3$OD) δ: 1.02-1.12 (m, 2 H), 1.30 (t, J = 10.21 Hz, 3H), 1.66 (s, 3 H), 1.67 (s, 3 H), 1.90-1.99 (m, 1 H), 2.65-2.72 (m, 1 H), 4.29 (q, J = 7.07 Hz, 2 H), 4.35 (s, 2 H), 6.99-7.07 (m, 3 H), 7.11-7.19 (m, 2 H), 8.08 (d, J = 3.39 Hz, 1 H). LCMS (APCI, M + H$^+$): 452.2. Anal. (C$_{23}$H$_{26}$FN$_7$O$_2$•1.22TFA•0.59H$_2$O): C, H, N. HPLC-UV Detection: 89% purity.<br>Method of Example 31 using 4-chloro-2-ethoxy-5-fluoropyrimidine in place of 31c. |
| 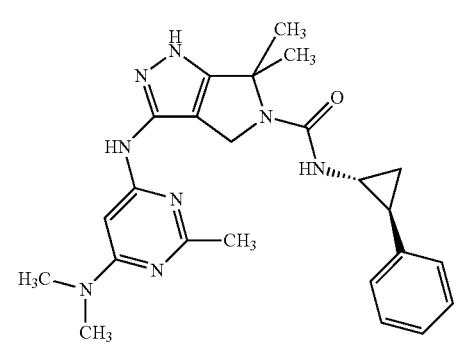<br>38 | 3-{[6-(dimethylamino)-2-methylpyrimidin-4-yl]amino}-6,6-dimethyl-N-[trans-2-phenylcyclopropyl]-4,6-dihydropyrrolo[3,4-c]pyrazole-5(1H)-carboxamide<br>$^1$H NMR (400 MHz, DMSO) δ: 1.06-1.21 (m, 2 H), 1.62 (s, 6 H), 2.35 (s, 3 H), 2.67 (m, 1 H), 3.28 (m, 7 H), 4.41 (s, 2 H), 7.10-7.27(m, 5H).<br>APCI-MS: [M + H] 447.<br>Method of Example 31 using 6-chloro-N,N,2-trimethylpyrimidin-4-amine in place of 31c. |
| 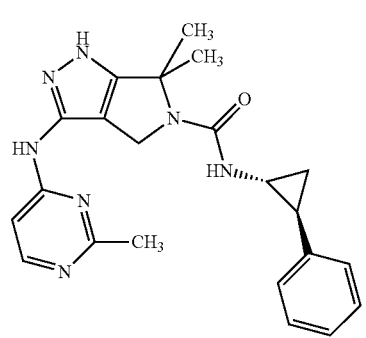<br>39 | 6,6-dimethyl-3-[(2-methylpyrimidin-4-yl)amino]-N-[trans-2-phenylcyclopropyl]-4,6-dihydropyrrolo[3,4-c]pyrazole-5(1H)-carboxamide<br>$^1$H NMR (400 MHz, DMSO) δ: 1.03 (m, 2 H), 1.87 (s, 3 H), 2.09 (s, 3H), 2.40 (s, 3 H), 4.00 (m, 2 H), 5.30 (s, 2 H), 6.49 (m, 1H) 7.09-7.27(m, 7H), 8.18 (m, 1 H),.<br>APCI-MS: [M + H] 404.<br>Method of Example 31 using 4-chloro-2-methylpyrimidine in place of 31c. |
| 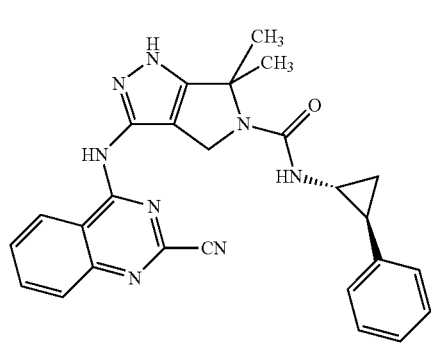<br>40 | 3-[(2-cyanoquinazolin-4-yl)amino]-6,6-dimethyl-N-[trans-2-phenylcyclopropyl]-4,6-dihydropyrrolo[3,4-c]pyrazole-5(1H)-carboxamide<br>R$_f$ = 0.11 (7% methanolic NH$_3$/CHCl$_3$). $^1$H NMR (400 MHz, CD$_3$OD): δ 1.15-1.25 (m, 2H), 1.79 (s, 6H), 2.06-2.11 (m, 1H), 2.80-2.84 (m, 1H), 4.76-4.77 (m, 2H), 7.11-7.15 (m, 3H), 7.22-7.25 (m, 2H), 7.75-7.79 (m, 1H), 7.88-7.90 (m, 1H), 7.95-7.98 (m, 1H), 8.41 (d, J = 7.5 Hz, 1H). LCMS 465 (M + H).<br>Anal. (C$_{26}$H$_{24}$N$_8$O•0.70 H$_2$O•0.05 hexane) C, H, N.<br>Method of Example 31 using 4-Chloroquinazoline-2-carbonitrile 40c in place of 31c. |

| Structure and Example # | Chemical name, Analytical data and comments |
|---|---|
| 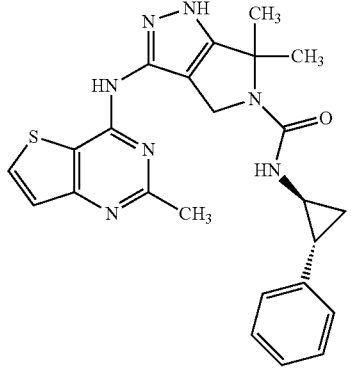<br>41 | 6,6-dimethyl-3-[(2-methylthieno[3,2-d]pyrimidin-4-yl)amino]-N-[trans-2-phenylcyclopropyl]-4,6-dihydropyrrolo[3,4-c]pyrazole-5(1H)-carboxamide<br>$^1$H NMR (400 MHz, CD$_3$OD): δ 1.15-1.19 (m, 2H), 1.79 (s, 3H), 1.80 (s, 3H), 2.01-2.05 (m, 1H), 2.76-2.78 (m, 1H), 2.80 (s, 3H), 4.50-4.51 (m, 2H), 7.11-7.15 (m, 3H), 7.22-7.25 (m, 2H), 7.46 (d, J = 5.5 Hz, 1H), 8.44 (d, J = 5.3 Hz, 1H). LCMS 460 (M + H).<br>Anal. (C$_{24}$H$_{25}$N$_7$OS•1.70 TFA•0.25 H$_2$O) C, H, N.<br>Method of Example 31 using 4-Chloro-2-methylthieno[3,2-d]pyrimidine (32c) in place of 31c. |
| 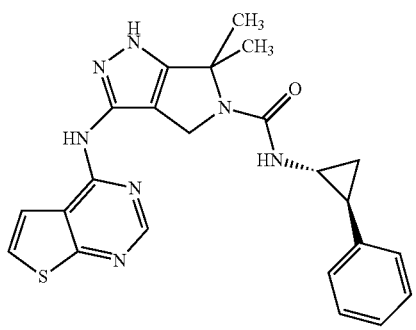<br>42 | 6,6-dimethyl-N-[trans-2-phenylcyclopropyl]-3-(thieno[2,3-d]pyrimidin-4-ylamino)-4,6-dihydropyrrolo[3,4-c]pyrazole-5(1H)-carboxamide<br>$^1$H NMR (CD$_3$OD) δ: 1.03-1.17 (m, 2 H), 1.69 (s, 3 H), 1.70 (s, 3 H), 1.93-2.03 (m, 1 H), 2.67-2.75 (m, 1 H), 4.47 (s, 2 H), 7.01-7.11 (m, 3 H), 7.15 (t, J = 7.58 Hz, 2 H), 7.44 (d, J = 5.56 Hz, 1 H), 8.30 (d, J = 5.30 Hz, 1 H), 8.77 (s, 1 H). LCMS (APCI, M + H$^+$): 446.2.<br>Anal. (C$_{23}$H$_{23}$N$_7$OS•1.86TFA•0.29H$_2$O•0.49TEA): C, H, N. HPLC-UV Detection: 87% purity<br>Method of Example 31 using 4-chlorothieno[2,3-d]pyrimidine in place of 31c. |
| 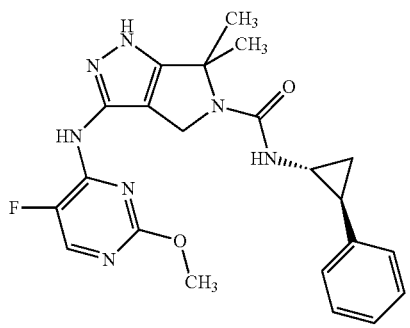<br>43 | 3-[(5-fluoro-2-methoxypyrimidin-4-yl)amino]-6,6-dimethyl-N-[trans-2-phenylcyclopropyl]-4,6-dihydropyrrolo[3,4-c]pyrazole-5(1H)-carboxamide.<br>$^1$H NMR (400 MHz, CD$_3$OD): δ 1.13-1.21 (m, 2H), 1.75 (s, 3H), 1.76 (s, 3H), 2.01-2.06 (m, 1H), 2.76-2.79 (m, 1H), 3.96 (s, 3H), 4.42-4.43 (m, 2H), 7.11-7.14 (m, 3H), 7.21-7.25 (m, 2H), 8.13 (d, J = 3.8 Hz, 1H). LCMS 438 (M + H). Anal. (C$_{22}$H$_{24}$N$_7$O$_2$F•1.00 TFA•0.10 H$_2$O) C, H, N.<br>Method of Example 31 using 4-Chloro-5-fluoro-2-methoxypyrimidine 43b in place of 31c. |
| 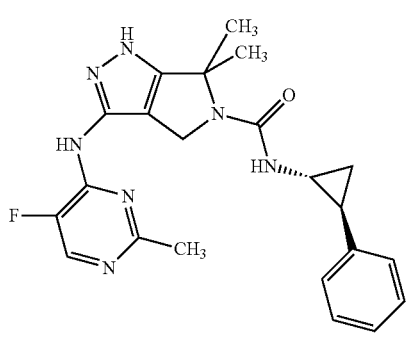<br>44 | 3-[(5-fluoro-2-methylpyrimidin-4-yl)amino]-6,6-dimethyl-N-[trans-2-phenylcyclopropyl]-4,6-dihydropyrrolo[3,4-c]pyrazole-5(1H)-carboxamide.<br>$^1$H NMR (400 MHz, CD$_3$OD): δ 1.16-1.21 (m, 2H), 1.76 (s, 3H), 1.77 (s, 3H), 2.01-2.06 (m, 1H), 2.67 (s, 3H), 2.77-2.80 (m, 1H), 4.52-4.53 (m, 2H), 7.11-7.15 (m, 3H), 7.22-7.26 (m, 2H), 8.43 (d, J = 5.0 Hz, 1H). LCMS 422 (M + H). Anal. (C$_{22}$H$_{24}$N$_7$OF•1.50 TFA) C, H, N. HPLC = 87% purity.<br>Method of Example 31 using 4-Chloro-5-fluoro-2-methylpyrimidine 44b in place of 31c. |

| Structure and Example # | Chemical name, Analytical data and comments |
|---|---|
| 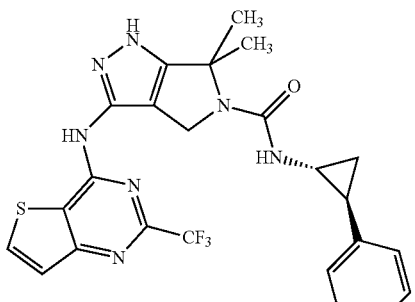<br>45 | 6,6-dimethyl-N-[trans-2-phenylcyclopropyl]-3-{[2-(trifluoromethyl)thieno[3,2-d]pyrimidin-4-yl]amino}-4,6-dihydropyrrolo[3,4-c]pyrazole-5(1H)-carboxamide<br>$^1$H NMR (400 MHz, MeOD) δ ppm: 1.18 (t, 2 H), 1.79 (d, J = 3.27 Hz, 6 H), 1.98-2.06 (m, 1 H), 2.77-2.82 (m, 1 H), 4.52 (s, 2 H), 7.11-7.16 (m, 3 H), 7.24 (t, J = 7.68 Hz, 2 H), 7.54 (d, J = 5.04 Hz, 1 H), 8.24 (d, J = 4.78 Hz, 1 H). Anal. $C_{24}H_{22}N_7OF_3S$•0.5HOAc•0.1H$_2$O) C, H, N. HPLC: >95% purity.<br>Method of Example 31 using 4-chloro-2-(trifluoromethyl)thieno[3,2-d]pyrimidine 45c in place of 31c. |
| 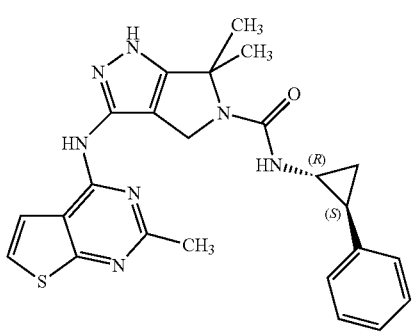<br>46 | 6,6-dimethyl-3-[(2-methylthieno[2,3-d]pyrimidin-4-yl)amino]-N-[(1R,2S)-2-phenylcyclopropyl]-4,6-dihydropyrrolo[3,4-c]pyrazole-5(1H)-carboxamide<br>$^1$H NMR (CD$_3$OD) δ: 1.02-1.15 (m, 2 H), 1.68 (s, 3 H), 1.69 (s, 3 H), 1.90-1.99 (m, 1 H), 2.56 (s, 3 H), 2.66-2.76 (m, 1 H), 4.43 (s, 2 H), 6.99-7.10 (m, 3 H), 7.14 (t, J = 6.06 Hz, 2 H), 7.40 (d, J = 6.06 Hz, 1 H), 7.51 (d, J = 6.06 Hz, 1 H). LCMS (APCI, M + H$^+$): 460.2. Anal. ($C_{24}H_{25}N_7OS$•0.76H$_2$O•0.22HOAc): C, H, N. HPLC-UV Detection: 94% purity.<br>Method of Example 32 using 4-chloro-2-methylthieno[2,3-d]pyrimidine (31c) in place of 32c. |
| 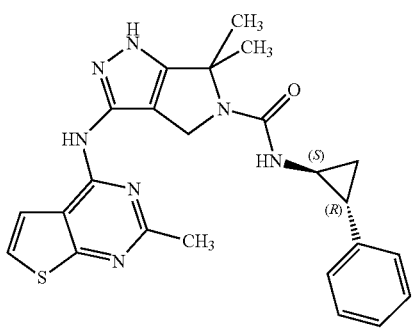<br>47 | 6,6-dimethyl-3-[(2-methylthieno[2,3-d]pyrimidin-4-yl)amino]-N-[(1S,2R)-2-phenylcyclopropyl]-4,6-dihydropyrrolo[3,4-c]pyrazole-5(1H)-carboxamide<br>$^1$H NMR (CD$_3$OD) δ: 1.02-1.17 (m, 2 H), 1.68 (s, 3 H), 1.69 (s, 3 H), 1.92-2.02 (m, 1 H), 2.56 (s, 3 H), 2.67-2.79 (m, 1 H), 4.43 (s, 2 H), 7.01-7.11 (m, 3 H), 7.14 (t, J = 8.08 Hz, 2 H), 7.40 (d, J = 6.06 Hz, 1 H), 7.51 (d, J = 6.06 Hz, 1 H). LCMS (APCI, M + H$^+$): 460.2. Anal. Calcd for ($C_{24}H_{25}N_7OS$•0.82H$_2$O•0.22HOAc): C, H, N. HPLC-UV Detection: 93% purity<br>Method of Example 32 using 4-chloro-2-methylthieno[2,3-d]pyrimidine (31c) in place of 32c, and 32e in place of 32d. |
| 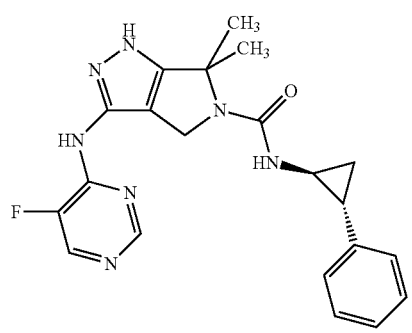<br>48 | 3-[(5-fluoropyrimidin-4-yl)amino]-6,6-dimethyl-N-[trans-2-phenylcyclopropyl]-4,6-dihydropyrrolo[3,4-c]pyrazole-5(1H)-carboxamide<br>$^1$H NMR (400 MHz, CD$_3$OD): δ 1.13-1.25 (m, 2H), 1.75 (s, 3H), 1.76 (s, 3H), 2.04-2.10 (m, 1 H), 2.76-2.80 (m, 1H), 4.50-4.53 (m, 2H), 7.11-7.25 (m, 5H), 8.25 (s, 1H), 8.51 (s, 1 H). LCMS 408 (M + H). HPLC >99% purity.<br>Method of Example 31 using 4-Chloro-5-fluoropyrimidine 48b in place of 31c. |

| Structure and Example # | Chemical name, Analytical data and comments |
|---|---|
| 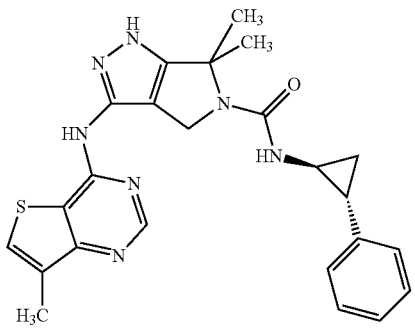<br>49 | 6,6-dimethyl-3-[(7-methylthieno[3,2-d]pyrimidin-4-yl)amino]-N-[trans-2-phenylcyclopropyl]-4,6-dihydropyrrolo[3,4-c]pyrazole-5(1H)-carboxamide<br>$^1$H NMR (400 MHz, DMSO) δ: 1.03-1.22 (m, 2 H), 1.65 (m, 6 H), 1.86 (m, 1 H), 2.36 (m, 3 H), 2.75 (m, 1H), 4.36 (m, 2 H), 6.35 (s, 1H), 7.10-7.27 (m, 6 H), 7.82 (s, 1 H), 8.65 (s, 1H). Anal. ($C_{24}H_{25}N_7OS$•0.15HOAc•1.2$H_2O$) C, H, N. APCI-MS: [M + H] 460. Method of Example 31 using 4-chloro-7-methylthieno[3,2-d]pyrimidine in place of 31c. |
| 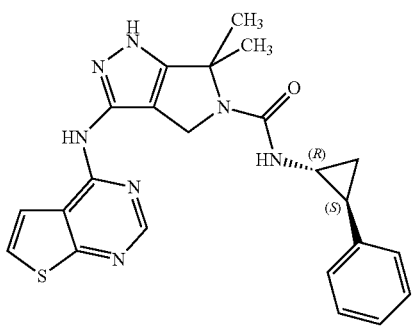<br>50 | 6,6-dimethyl-N-[(1R,2S)-2-phenylcyclopropyl]-3-(thieno[2,3-d]pyrimidin-4-ylamino)-4,6-dihydropyrrolo[3,4-c]pyrazole-5(1H)-carboxamide<br>$^1$H NMR (CD$_3$OD) δ: 1.01-1.16 (m, 2 H), 1.68 (s, 3 H), 1.69 (s, 3 H), 1.93-2.02 (m, 1 H), 2.65-2.74 (m, 1 H), 4.43 (s, 2 H), 7.00-7.09 (m, 3 H), 7.14 (t, J = 7.33 Hz, 2 H), 7.34 (d, J = 5.56 Hz, 1 H), 8.03 (d, J = 5.30 Hz, 1 H), 8.58 (s, 1 H). LCMS (APCI, M + H$^+$): 446.1.<br>Anal. ($C_{23}H_{23}N_7OS$•1.12$H_2O$•0.32HOAc): C, H, N. HPLC-UV Detection: 92% purity<br>Method of Example 32 using 4-chloro-thieno[2,3-d]pyrimidine in place of 32c. |
| 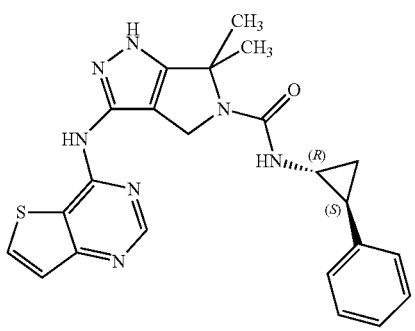<br>51 | 6,6-dimethyl-N-[(1R,2S)-2-phenylcyclopropyl]-3-(thieno[3,2-d]pyrimidin-4-ylamino)-4,6-dihydropyrrolo[3,4-c]pyrazole-5(1H)-carboxamide<br>$^1$H NMR (CD$_3$OD) δ: 1.01-1.16 (m, 2 H), 1.68 (s, 3 H), 1.69 (s, 3 H), 1.93-2.02 (m, 1 H), 2.66-2.74 (m, 1 H), 4.42 (s, 2 H), 7.00-7.09 (m, 3 H), 7.14 (t, J = 7.33 Hz, 2 H), 7.34 (d, J = 5.56 Hz, 1 H), 8.02 (d, J = 5.56 Hz, 1 H), 8.58 (s, 1 H). LCMS (APCI, M + H$^+$): 446.1.<br>Anal. ($C_{23}H_{23}N_7OS$•1.08$H_2O$•0.28HOAc): C, H, N. HPLC: 90% purity.<br>Method of Example 32 using 4-chlorothieno[3,2-d]pyrimidine in place of 32c. |
| 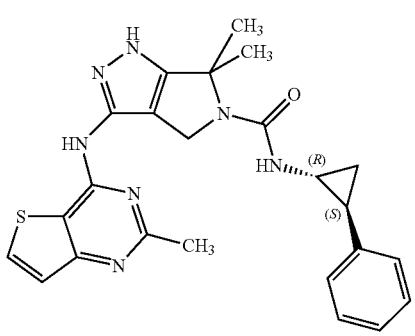<br>52 | 6,6-dimethyl-3-[(2-methylthieno[3,2-d]pyrimidin-4-yl)amino]-N-[(1R,2S)-2-phenylcyclopropyl]-4,6-dihydropyrrolo[3,4-c]pyrazole-5(1H)-carboxamide<br>$^1$H NMR (400 MHz, CH$_3$OD): δ 1.15-1.19 (m, 2H), 1.79 (s, 3H), 1.80 (s, 3H), 2.01-2.05 (m, 1H), 2.76-2.78 (m, 1H), 2.80 (s, 3H), 4.50-4.51 (m, 2H), 7.11-7.15 (m, 3H), 7.22-7.25 (m, 2H), 7.46 (d, J = 5.5 Hz, 1H), 8.44 (d, J = 5.3 Hz, 1H). LCMS 460 (M + H). Anal. ($C_{24}H_{25}N_7OS$•1.50 TFA•0.25 $H_2O$) C, H, N. HPLC >99% purity.<br>Method of Example 32 using 4-Chloro-2-methylthieno[3,2-d]pyrimidine in place of 32c. |

| Structure and Example # | Chemical name, Analytical data and comments |
|---|---|
| 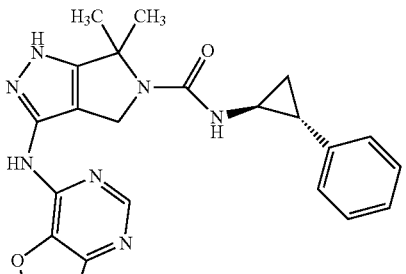 53 | 3-(furo[3,2-d]pyrimidin-4-ylamino)-6,6-dimethyl-N-(trans-2-phenylcyclopropyl)-4,6-dihydropyrrolo[3,4-c]pyrazole-5(1H)-carboxamide<br>$^1$H NMR (CD$_3$OD) δ: 1.01-1.16 (m, 2 H), 1.68 (s, 3 H), $^1$H NMR (400 MHz, DMSO-d6) δ: 1.03 (m, 1H), 1.22 (m, 1H), 1.64 (s, 6H), 1.92 (m, 1H), 2.75 (m, 1H), 4.38 (d, J = 12.1 Hz, 1H), 4.43 (d, J = 12.2 Hz, 1H), 6.35 (s, 1H), 7.05-7.16 (m, 3H), 7.2-7.28 (m, 2H), 8.33 (br s, 1H), 8.52 (s, 1H), 10.38 (br s, 1H). Anal. (C$_{23}$H$_{23}$N$_7$O$_2$•0.2HOAc•1H$_2$O) C, H, N. APCI-MS: [M + H] 430.<br>Method of Example 31 using 4-chlorofuro[3,2-d]pyrimidine (prepared according to procedure reported in WO2004013141, page 131-133) in place of 31c. |

Preparation of 40c:
4-Chloroquinazoline-2-carbonitrile

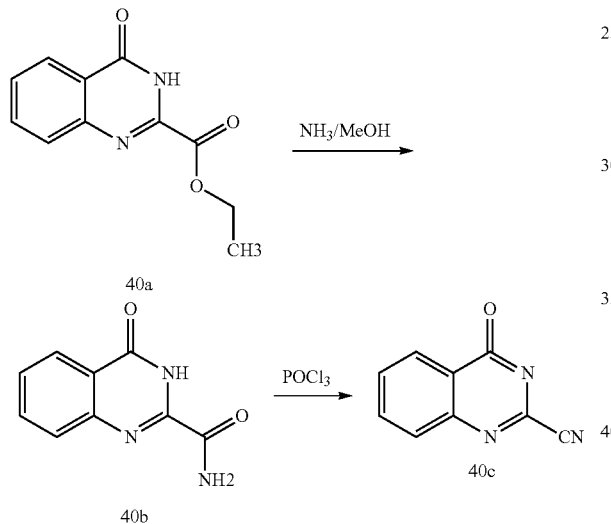

Ethyl 4-quinazolone-2-carboxylate (40a, 2.54 g, 11.67 mmol) was dissolved in MeOH (29 mL) in a 200 mL round-bottom flask and cooled to 0° C. Anhydrous ammonia gas was bubbled into the solution for 30 minutes. The flask was then sealed with a suba-seal stopper which was secured with copper wire. The reaction was then warmed to ambient temperature and stirred overnight. The solvent was removed under reduced pressure to give 4-Oxo-3,4-dihydroquinazoline-2-carboxamide (40b, 2.20 g, 99%) as a white solid. R$_f$=0.13 (7% MeOH/CHCl$_3$). $^1$H NMR (400 MHz, DMSO-d$_6$): δ 7.58-7.62 (m, 1H), 7.76 (d, J=7.6 Hz, 1H), 7.85-7.89 (m, 1H), 8.06 (s, 1H), 8.16 (dd, J=7.8, 1.2 Hz), 8.35 (s, 1H), 11.91 (s, 1H). LCMS 190 (M+H). HPLC>99% purity.

4-Oxo-3,4-dihydroquinazoline-2-carboxamide (40b, 0.51 g, 2.69 mmol) was heated to 100° C. in POCl$_3$ (7.0 mL) for three hours. The solvent was removed under reduced pressure. Ice-cold water was carefully added to the flask, and the insoluble product was filtered off. The filtrate was extracted three times with chloroform. The combined organics were dried (MgSO$_4$) and evaporated to give 4-Chloroquinazoline-2-carbonitrile (40c, 0.21 g). 95% pure by HPLC and used without further purification. The insoluble product was puri- fied by flash silica gel chromatography eluting with 3-30% EtOAc/hexane to give an additional 0.22 g of 40c as a white solid for an overall yield of 62%. R$_f$=0.53 (30% EtOAc/hexane). $^1$H NMR (400 MHz, DMSO-d$_6$): δ 8.07-8.11 (m, 1H), 8.24-8.31 (m, 2H), 8.41 (d, J=8.4 Hz, 1H).

Preparation of 43b:
4-Chloro-5-fluoro-2-methoxypyrimidine

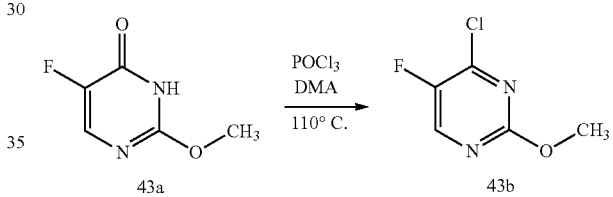

2-Methoxy-5-fluorouracil (43a, 1.04 g, 7.21 mmol) and N,N-dimethylaniline (1.80 mL) were heated in POCl$_3$ at 110° C. for 90 minutes. After cooling, the reaction was added carefully to ice. The product was extracted with diethylether. The ether layer was washed with sequentially with 2N HCl, water, and brine followed by drying (MgSO$_4$). The ether was carefully removed under reduced pressure to give 43b as a volatile liquid (0.39 g, 34%) which was used without further purification. R$_f$=0.26 (10% EtOAc/hexane). $^1$H NMR (400 MHz, DMSO-d$_6$): δ 3.91 (s, 3H), 8.79 (s, 1H).

Preparation of 44b:
4-Chloro-5-fluoro-2-methylpyrimidine

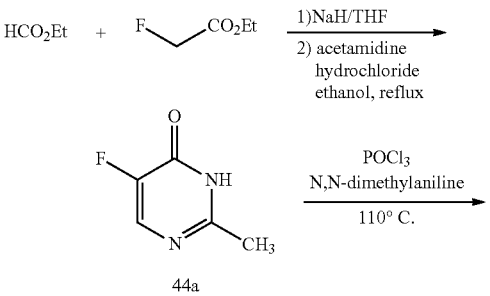

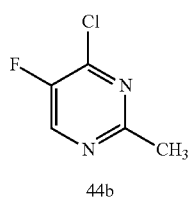

Sodium hydride (60%, 5.0 g, 125 mmol) was washed with hexane to remove the mineral oil and dried, then suspended in THF (50 mL) and cooled to 0° C. Ethyl fluoroacetate (13.30 g, 125 mmol) and ethyl formate (15.14 mL, 187 mmol) were mixed together and added to the stirring suspension. The reaction was slowly warmed to ambient temperature and stirred 3 days. The solvent was removed. A mixture of acetamidine hydrochloride (11.81 g, 125 mmol), sodium ethoxide (8.86 g, 125 mmol), and ethanol (60 mL) were added to the reaction followed by refluxing overnight. The ethanol was removed under reduced pressure. The residue was dissolved in a minimum of water and acidified to pH=6 with concentrated HCl. The crude products were then extracted by salting out from the aqueous phase and washing exhaustively with 4:1 CHCl$_3$/isopropanol. The combined organic phases were dried (MgSO$_4$) and evaporated. The crude solid was purified by silica gel chromatography eluting with 5-90% EtOAc/hexane to give 5-Fluoro-2-methylpyrimidin-4(3H)-one (44a, 0.95 g, 6%) as a white solid. R$_f$=0.08 (75% EtOAc/hexane). $^1$H NMR (400 MHz, DMSO-d$_6$): δ 2.25 (d, J=1.0 Hz, 3H), 7.93 (d, J=3.8 Hz, 1H), 12.95 (br, 1H). LCMS 129.

Compound 44b was prepared following the method of 43b, except that 44a was used in place of 43a. Compound 44b (0.11 g, 10%) was obtained as a volatile liquid and was used without further purification. R$_f$=0.39 (5% EtOAc/hexane). $^1$H NMR (400 MHz, DMSO-d$_6$): δ 2.60 (s, 3H), 8.86 (s, 1H).

Preparation of Compound 45c: 4-chloro-2-(trifluoromethyl)thieno[3,2-d]pyrimidine

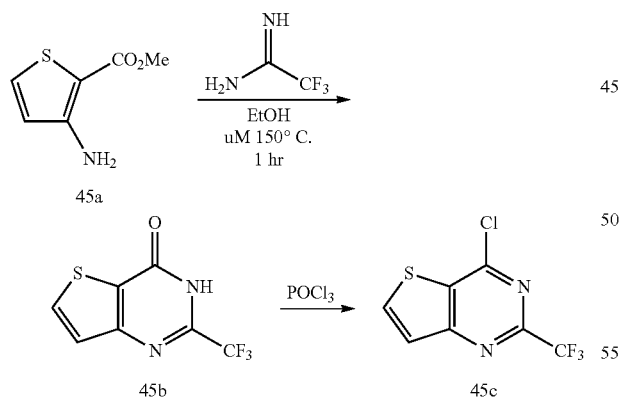

To a stirring solution of methyl 3-aminothiophene-2-carboxylate (45a, 1.57, 10.0 mmol) in EtOH (10 mL) was added trifluoroacetamidine (2.24 g, 2 eq) and trifluoroacetic acid (1.54 ml, 2 eq). The resulting mixture was heated to 150° C. for 1 hour in microwave reactor. The reaction mixture was cool and filtered to provide 2-(trifluoromethyl)thieno[3,2-d]pyrimidine-4(3H)-one 45b as a solid (0.61 g). $^1$H NMR (400 MHz, MeOD) δ ppm: 7.49 (d, J=5.29 Hz, 2H), 8.18 (d, J=5.29 Hz, 1H).

A suspension of 2-(trifluoromethyl)thieno[3,2-d]pyrimidine-4(3H)-one (45b, 0.61 g, 2.77 mmol) in POCl$_3$ was refluxed under an atmosphere of nitrogen for 3 hrs and then concentrated to dryness under reduced pressure. The residue was partitioned between ethyl acetate and saturated NaHCO$_3$, dried, and concentrated to give compound 45c as a solid (0.58 g, 88%). $^1$H NMR (400 MHz, MeOD) δ ppm: 7.79 (d, J=5.54 Hz, 1H), 8.59 (d, J=5.54 Hz, 1H).

Preparation of 48b: 4-Chloro-5-fluoropyrimidine

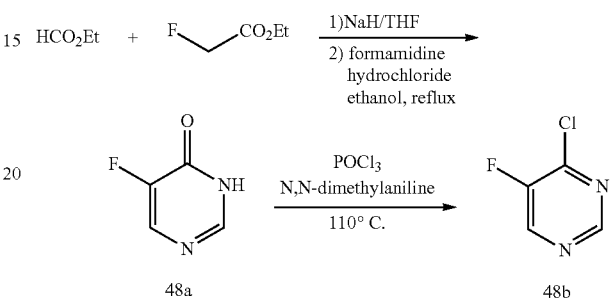

Sodium hydride (60%, 5.0 g, 125 mmol) was washed with hexane to remove the mineral oil and dried, then suspended in THF (50 mL) and cooled to 0° C. Ethyl fluoroacetate (13.35 g, 126 mmol) and ethyl formate (13.99 g, 189 mmol) were mixed together and added to the stirring suspension. The reaction was slowly warmed to ambient temperature and stirred overnight. The solvent was removed. A mixture of formamidine hydrochloride (10.33 g, 126 mmol), sodium ethoxide (8.92 g, 126 mmol), and ethanol (60 mL) were added to the reaction followed by refluxing overnight. The ethanol was removed under reduced pressure. The residue was dissolved in a minimum of water and acidified to pH=6 with ethanolic HCl. The solids were filtered off and the filtrate concentrated. The crude solid was purified by silica gel chromatography eluting with 0-9% MeOH/CHCl$_3$ to give 5-Fluoropyrimidin-4(3H)-one as a white solid (48a, 1.05 g, 7%). R$_f$=0.13 (75% EtOAc/hexane). $^1$H NMR (400 MHz, DMSO-d$_6$): δ 8.05-8.09 (m, 2H), 13.14 (br, 1H).

Following the procedure to make 43b, compound 48b was synthesized from 48a to give 0.97 g (80%) of a volatile liquid which was used without further purification. R$_f$=0.37 (5% EtOAc/hexane). $^1$H NMR (400 MHz, DMSO-d$_6$): δ 8.93 (s, 1H), 9.01 (s, 1H).

Example 54

N-[(1S)-2-(Dimethylamino)-1-phenylethyl]-3-[(6-ethylpyrimidin-4-yl)amino]-6,6-dimethyl-4,6-dihydropyrrolo[3,4-c]pyrazole-5(1H)-carboxamide

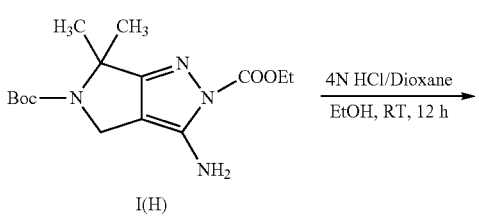

-continued

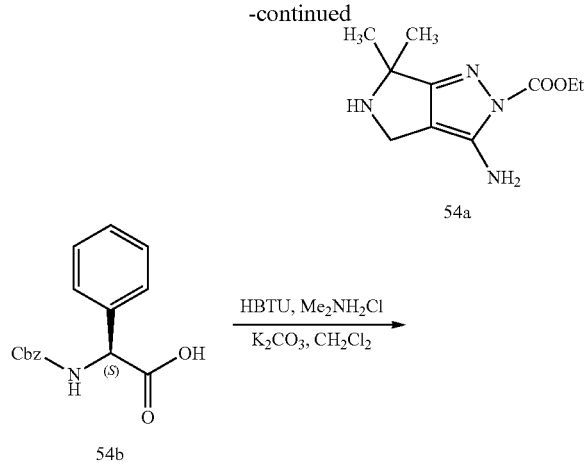

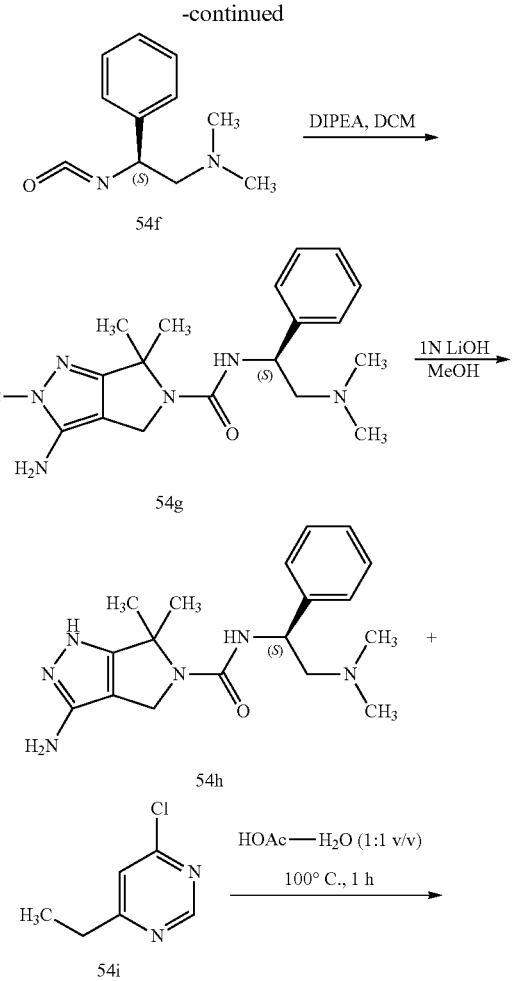

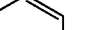

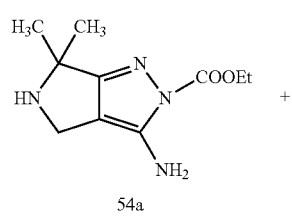

Preparation of I(H): 5-tert-butyl 2-ethyl 3-amino-6,6-dimethylpyrrolo[3,4-c]pyrazole-2,5(4H,6H)-dicarboxylate The synthetic route of compound I(H) can be found in Scheme 1 under the "Detailed Description" of this application. The detailed synthetic condition of for the preparation of I(H) can be found in U.S. Patent Application Publication No. 2003/0171357 and PCT Publication WO 02/12242, the disclosure of which are incorporated herein by reference.

Preparation of Compound 54a: ethyl 3-amino-6,6-dimethyl-5,6-dihydropyrrolo[3,4-c]pyrazole-2(4H)-carboxylate dihydrochloride To a stirred slurry of 5-tert-butyl 1-ethyl 3-amino-6,6-dimethyl-4,6-dihydropyrrolo[3,4-c]pyrazole-1,5-dicarboxylate (I(H), 30.0 g, 92.5 mmol) in ethanol (200 mL) was drop wise added HCl 4 M solution in hexanes (116 mL) drop wise. The resulting clear solution was stirred at room temperature for 12 h. The reaction mixture was concentrated under vacuum to a residue and stirred with hexane (250 mL) for 10 min. The solid product was collected by filtration, washed with hexane (100 mL) and dried under vacuum at 40° C. for 15 h to get ethyl 3-amino-6,6-dimethyl-5,6-dihydropyrrolo[3,4-c]pyrazole-1(4H)-carboxylate dihydrochloride (54a, 27.0 g, 98.5%) as white solid. $^1$H NMR (300 MHz, dmso-d$_6$): δ 1.31 (td, J=7, 1.3 Hz, 3H), 1.59 (s, 6H), 4.09 (t, J=3.7 Hz, 2H), 4.36 (qd, J=7.2, 1.2 Hz, 2H), 10.12 (br s, 2H).

Preparation of Compound 54c: benzyl [(1S)-2-(dimethylamino)-2-oxo-1-phenylethyl]-carbamate To a mixture of (2S)-{[(benzyloxy)carbonyl]amino}(phenyl)acetic acid (54b, 196 g, 688 mmol), HBTU (261 g, 688 mmol), and dichloromethane (2.8 L) were added sequentially potassium carbonate (285 g, 2.06 mol) and dimethylamine hydrochloride (84.1 g, 1031 mmol). The reaction mixture was heated at 40° C. overnight. After cooling to room temperature, the solids were filtered, washed with ethyl acetate (2×500 mL) and the filtrate concentrated to a residue. Water (1 L) was added to the residue and the solution kept in an ultrasonic cleanser for 2 hours. The precipitated solids were collected and washed with water (4×300 mL), hexane (2×500 mL), and dried under vacuum for 24 hours. The solid crude product was dissolved in chloroform (300 mL) and un-dissolved solids were filtered off. The filtrate was concentrated to dryness and the residue dissolved in hexane/ethyl acetate (2:1) (250 mL) and allowed to stand at room temperature overnight. The resulting crystals were collected by filtration, washed with hexane/ethyl acetate (3:1) (100 mL) and dried in high vacuum at 40° C. for 24 hours to give compound 54c (100.0 g, 47%) as a white crystalline solid. $^1$H NMR (CDCl$_3$) δ: 2.88 (s, 3H), 2.98 (s, 3H), 5.01 (d, J=12.2 Hz, 1H), 5.11 (d, J=12.2 Hz, 1H), 5.58 (d, J=7.5 Hz, 1H), 6.37 (d, J=7.2 Hz, 1H), 7.32 (m, 10H).

Preparation of Compound 54d: (2S)-2-amino-N,N-dimethyl-2-phenylacetamide

To a solution of 54c (80.0 g, 256 mmol) in ethanol (1.2 L) was added a slurry of Pd/C (10%, 9.0 g) in ethyl acetate (50 mL). The reaction mixture was shaken in Parr-apparatus under hydrogen (40 psi) overnight. The catalyst was removed by filtration through celite. The filter pad was washed with ethanol (2×200 mL) and the combined filtrate was concentrated to give 54d (40.2 g, 88%) as a white solid. $^1$H NMR (CDCl$_3$) δ: 2.85 (s, 3H), 2.99 (s, 3H), 4.72 (s, 1H), 7.33 (m, 5H).

Preparation of Compound 54e: N-[(2S)-2-amino-2-phenylethyl]-N,N-dimethylamine A flask containing dry THF (2300 mL) under a nitrogen atmosphere was chilled by an ice-water bath. Lithium aluminum hydride pellets (59.0 g, 1555 mmol) were added. To this LAH suspension, a solution of amide 54d (123.0 g, 691 mmol) in dry THF (800 mL) was slowly added over approximately 1 hour. The resulting reaction mixture was heated at reflux for 5 hours, then cooled to 10° C. The cooled reaction mixture was slowly quenched with saturated sodium sulfate solution (380 mL) and stirred overnight. The precipitated solids were filtered off and washed with ethyl acetate (4×500 mL). The filtrate was concentrated to a residue that was purified on silica gel column (10% methanol, 5% triethylamine in chloroform) to afford 54e (66.7 g, 59%) as a light yellow liquid. $^1$H NMR (CDCl$_3$) δ: 2.24 (dd, J=3.6, 12.1 Hz, 1H), 2.29 (s, 6H), 2.47 (dd, J=10.6, 12.1 Hz, 1H), 4.07 (dd, J=3.6, 10.4 Hz, 1H), 7.24 (m, 1H), 7.37 (m, 4H).

Preparation of Compound 54f: N-[(2S)-2-isocyanato-2-phenylethyl]-N,N-dimethylamine hydrochloride To a cooled (0° C.) and stirred solution of triphosgene (27.1 g, 91.32 mmol) in DCM (250 mL) was drop wise added a solution of diisopropylethyl amine (23.6 g, 182.26 mmol) in DCM (50 mL) over a period of 20 min. A solution of N-[(2S)-2-amino-2-phenylethyl]-N,N-dimethylamine (54e, 15.0 g, 91.32 mmol) in DCM (100 mL) was drop wise added to the brown reaction mixture while maintaining the temperature below 10° C. The resulting reaction mixture was removed from cooling and stirred for 2 h at room temperature. The reaction mixture was concentrated under vacuum to a residue and stirred with 10% DCM in hexane (50 mL). The solid N-[(2S)-2-isocyanato-2-phenylethyl]-N,N-dimethylamine hydrochloride compound 54f was separated by filtration and used for the next reaction without further purification. (Note: The obtained solid product was stored under nitrogen). $^1$H NMR (300 MHz, dmso-d$_6$): δ 3.29 (s, 3H), 3.38 (s, 3H), 3.68 (t, J=10.1 Hz, 1H), 4.42 (dd, J=11.5, 6.5 Hz, 1H), 5.35 (dd, J=9.6, 6.2 Hz, 1H), 7.4-7.6 (m, 5H).

Preparation of Compound 54g: (S)-ethyl 3-amino-5-((2-(dimethylamino)-1-phenylethyl)carbamoyl)-6,6-dimethyl-5,6-dihydropyrrolo[3,4-c]pyrazole-2(4H)-carboxylate To a cooled (0° C.) and stirred slurry of ethyl 3-amino-6,6-dimethyl-5,6-dihydropyrrolo[3,4-c]pyrazole-1(4H)-carboxylate dihydrochloride (54a, 25.0 g, 84.12 mmol) were sequence ally added DIPEA (74 mL, 420.1 mmol) and N-[(2S)-2-isocyanato-2-phenylethyl]-N,N-dimethylamine hydrochloride (54f, 17.1 g, 75.71 mmol). After stirring at room temperature for 10 h under nitrogen, the mixture was diluted with DCM (100 mL) and washed with water (2×100 mL). The organic solution was dried (Na$_2$SO$_4$), filtered, and concentrated under vacuum. The obtained crude product was purified on silica gel column (10% MeOH/DCM) to get compound 54g (23.0 g, 73.7%) as light yellow solid. M.p: 96-97° C. $^1$H NMR (300 MHz, dmso-d$_6$): δ 1.32 (t, J=7.1 Hz, 3H), 1.51 (s, 3H), 1.57 (s, 3H), 2.19 (s, 6H), 2.40 (m, 1H), 2.60 (m, 1H), 4.23 (m, 2H), 4.35 (q, J=6.7 Hz, 2H), 4.78 (m, 1H), 6.00 (d, J=6 Hz, 1H), 6.55 (s, 2H), 7.18-7.40 (m, 5H). LCMS (APCI, M+H$^+$): 415.

Preparation of Compound 54h: 3-Amino-N-[(1S)-2-(dimethylamino)-1-phenylethyl]-6,6-dimethyl-4,6-dihydropyrrolo[3,4-c]pyrazole-5(1H)-carboxamide Ethyl 3-amino-5-({[(1S)-2-(dimethylamino)-1-phenylethyl]amino}carbonyl)-6,6-dimethyl-5,6-dihydropyrrolo[3,4-c]pyrazole-1(4H)-carboxylate (54g, 9.24 g, 22.30 mmol) was dissolved in MeOH (225 mL). A solution of 1N LiOH (36 mL) was added, and the reaction was stirred at ambient temperature for two hours. The solvent was removed under reduced pressure, the residue diluted with water, and the product was extracted into 4:1 CHCl$_3$/iPrOH. The organic layer was separated, washed with brine, dried (MgSO$_4$), and evaporated to give compound 54h (7.00 g, 92%) as a yellow amorphous solid which was used without further purification. R$_f$=0.16 (10% methanolic NH$_3$/CHCl$_3$). $^1$H NMR (400 MHz, CD$_3$OD): δ 1.60 (s, 3H), 1.67 (s, 3H), 2.32 (s, 6H), 2.44 (dd, J=12.9, 4.5 Hz, 1H), 2.78 (dd, J=12.6, 10.6 Hz, 1H), 4.34 (d, J=10.3 Hz, 1H), 4.40 (d, J=10.6 Hz, 1H), 4.90-4.98 (m, 1H), 7.20-7.24 (m, 1H), 7.28-7.36 (m, 4H). LCMS 343.

Compound 54h (0.18 g, 0.52 mmol) and 4-chloro-6-ethylpyrimidine (54i, 0.08 g, 0.574 mmol) were mixed in 1:1 HOAc/H₂O (2.0 mL) and heated to 100° C. for 1 hour. The reaction was neutralized with solid NaHCO₃ and diluted with water and 4:1 CHCl₃/iPrOH. The organic phase was separated, washed with brine, then dried (MgSO₄) and evaporated. The product was purified by flash silica gel chromatography eluting with 0-5% methanolic NH₃/CHCl₃. The product was further purified by preparative HPLC to give the titled compound 54 N-[(1S)-2-(Dimethylamino)-1-phenylethyl]-3-[(6-ethylpyrimidin-4-yl)amino]-6,6-dimethyl-4,6-dihydropyrrolo[3,4-c]pyrazole-5(1H)-carboxamide as a white solid (0.077 g, 20%). R$_f$=0.16 (10% methanolic NH₃/CHCl₃). ¹H NMR (400 MHz, CD₃OD): δ 1.34 (t, J=7.8 Hz, 3H), 1.72 (s, 3H), 1.78 (s, 3H), 2.77-2.82 (m, 2H), 2.97 (s, 3H), 3.05 (s, 3H), 3.45-3.51 (m, 1H), 3.63-3.69 (m, 1H), 4.63-4.66 (m, 1H), 4.71-4.76 (m, 1H), 5.43 (dd, J=11.3, 3.8 Hz), 6.94 (br, 1H), 7.32-7.36 (m, 1H), 7.39-7.47 (m, 4H), 8.74 (s, 1H). LCMS 449 (M+H). Anal. (C₂₄H₃₂N₈O.2.40TFA.1.0H₂O) C,H,N. HPLC>98% purity.

Example 55

N-[(1S)-2-(dimethylamino)-1-phenylethyl]-6,6-dimethyl-3-{[2-(trifluoromethyl)pyrimidin-4-yl]amino}-4,6-dihydropyrrolo[3,4-c]pyrazole-5(1H)-carboxamide

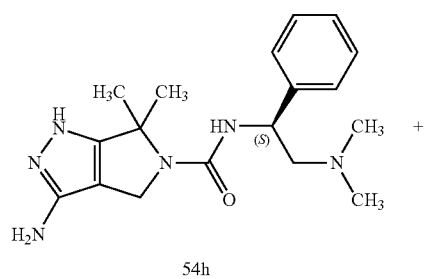

54h

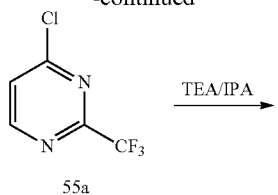

55a

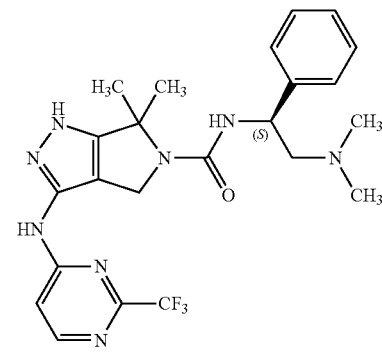

55

To 4-chloro-2(trifluoromethyl)pyrimidine (55a, 74 mg, 0.4 mmol), (S)-3-amino-N-(2-(dimethylamino)-1-phenylethyl)-6,6-dimethylpyrrolo[3,4-c]pyrazole-5(1H, 4H, 6H)-carboxamide (54h, 141 mg, 0.4 mmol) in IPA (1 mL), was added TEA (114 mL, 0.8 mmol). The reaction was heated in microwave oven at 140° C. for 20 min. HPLC yielded the title compound 55 (S)-N-(2-(dimethylamino)-1-phenylethyl)-6,6-dimethyl-3-(2-(trifluoromethylpyrimidin-4-ylamino)pyrrolo[3,4-c]pyrazole-5(1H,4H,6H)-carboxamide as a white powder (8 mg, 4%). ¹H NMR (400 MHz, DCM) δ: 1.30 (m, 6H), 1.58 (m, 6H), 3.63 (m, 2H), 3.86 (m, 2H), 4.04 (m, 1H), 7.41-7.50 (m, 6H), 8.53 (s, 1H). Anal. (C₂₃H₂₇N₈OF3.2.41TFA.1.7H₂O) C, H, N. APCI-MS: [M+H] 489.

| Structure and Example # | Chemical name, Analytical data and comments |
|---|---|
| 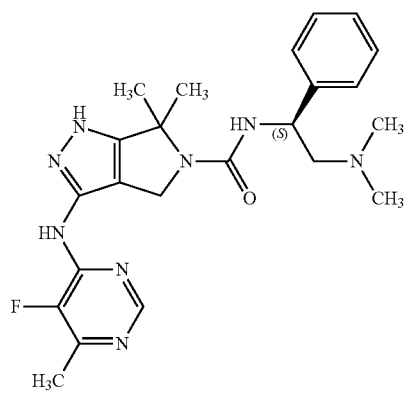 56 | N-[(1S)-2-(dimethylamino)-1-phenylethyl]-3-[(5-fluoro-6-methylpyrimidin-4-yl)amino]-6,6-dimethyl-4,6-dihydropyrrolo[3,4-c]pyrazole-5(1H)-carboxamide. R$_f$ = 0.13 (7% methanolic NH₃/CHCl₃). ¹H NMR (400 MHz, CD₃OD): δ 1.67 (s, 3H), 1.74 (s, 3H), 2.34 (s, 6H), 2.42 (d, J = 2.8 Hz, 3H), 2.44-2.47 (m, 1H), 2.80-2.86 (m, 1H), 4.63-4.68 (m, 2H), 4.97-5.02 (m, 1H), 7.20-7.24 (m, 1H), 7.30-7.37 (m, 4H), 8.39 (s, 1H). LCMS 453 (M + H). Anal. (C₂₃H₂₉N₈OF•0.35 H₂O•0.35 hexane) C, H, N. HPLC >98% purity. Method of Example 54 using 4-Chloro-5-fluoro-6-methylpyrimidine in place of 54i. |

| Structure and Example # | Chemical name, Analytical data and comments |
|---|---|
| 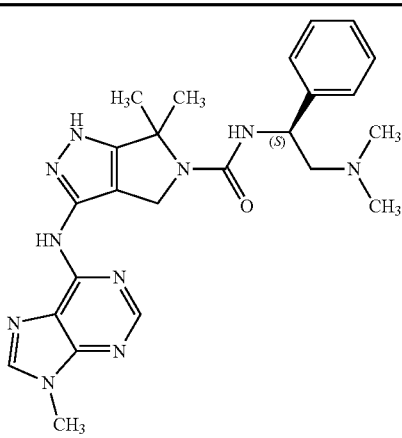<br>57 | N-[(1S)-2-(dimethylamino)-1-phenylethyl]-6,6-dimethyl-3-[(9-methyl-9H-purin-6-yl)amino]-4,6-dihydropyrrolo[3,4-c]pyrazole-5(1H)-carboxamide<br>$^1$H NMR (400 MHz, CD$_3$OD): δ 1.68 (s, 1H), 1.71 (s, 3H), 2.07 (s, 3H), 2.87 (m, 4H), 3.02 (br s, 3H), 3.20 (dd, J = 14.7, 7.3 Hz, 1H), 3.84 (d, J = 14.4 Hz, 1H), 3.96 (d, 14.1 Hz, 1H), 4.99 (s, 2H), 7.35-7.7 (m, 5H), 8.03 (td, J = 7.6, 1.1 Hz, 1H), 8.20 (d, J = 7.5 Hz, 1H), 8.72 (d, J = 4.6 Hz, 1H). LCMS [M + H]$^+$ 475. Anal. (C$_{24}$H$_{30}$N$_{10}$O•2H$_2$O•2.74TFA) C, H, N.<br>Method of Example 54 using 6-chloro-9-methyl-9H-purine and in place of 54i. |
| 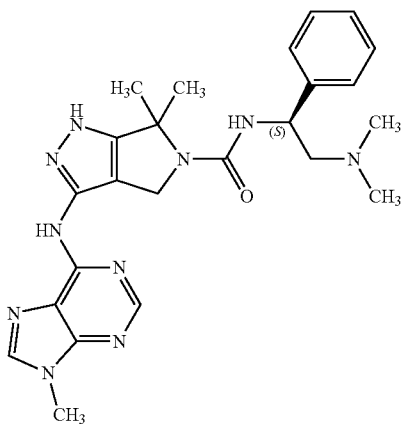<br>58 | N-[(1S)-2-(dimethylamino)-1-phenylethyl]-6,6-dimethyl-3-[(2-methylthieno[2,3-d]pyrimidin-4-yl)amino]-4,6-dihydropyrrolo[3,4-c]pyrazole-5(1H)-carboxamide<br>$^1$H NMR (400 MHz, DMSO-d$_6$): δ 1.61 (s, 3H), 1.70 (s, 3H), 2.62 (s, 3H), 2.81 (d, J = 4.6 Hz, 3H), 2.91 (d, J = 4.8 Hz, 3H), 3.34 (m, 1H), 3.46 (m, 1H), 4.63 (s, 2H), 5.34 (m, 1H), 6.58 (d, J = 9.3 Hz, 1H), 7.18-7.46 (m, 5H), 7.58 (d, J = 6 Hz, 1H), 7.83 (br d, J = 5.8 Hz, 1H), 9.13 (br s, 1H), 10.39 (s, 1H). LCMS [M + H]$^+$ 491 Anal. (C$_{26}$H$_{30}$N$_8$OS•1H$_2$O•2.55TFA) C, H, N.<br>Method Example 54 using 4-chloro-2-methylthieno[2,3-d]pyrimidine in place of 54i. |
| 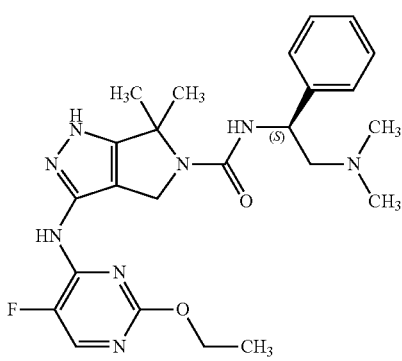<br>59 | N-[(1S)-2-(dimethylamino)-1-phenylethyl]-3-[(2-ethoxy-5-fluoropyrimidin-4-yl)amino]-6,6-dimethyl-4,6-dihydropyrrolo[3,4-c]pyrazole-5(1H)-carboxamide<br>$^1$H NMR (400 MHz, DMSO-d$_6$): δ 1.28 (t, J = 7 Hz, 3H), 1.59 (s, 3H), 1.66 (s, 3H), 2.81 (d, J = 4.5 Hz, 3H), 2.88 (d, J = 4.6 Hz, 3H), 4.22 (d, J = 7.1 Hz, 1H), 4.26 (d, J = 7 Hz, 1H), 4.49 (s, 2H), 5.34 (m, 1H), 6.59 (d, J = 9.1 Hz, 1H), 7.25-7.45 (m, 5H), 8.14 (d, J = 3 Hz, 1H), 8.94 (br s, 2H), 10.03 (s, 1H). LCMS [M + H]$^+$ 483 Anal. (C$_{24}$H$_{31}$N$_8$FO$_2$•0.5H$_2$O•1.64TFA) C, H, N.<br>Method of Example 54 using 4-chloro-2-ethoxy-5-fluoropyrimidine in place of 54i. |

| Structure and Example # | Chemical name, Analytical data and comments |
|---|---|
| 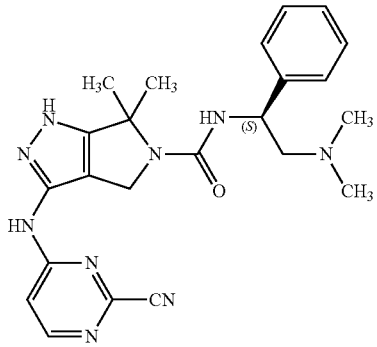<br>60 | 3-[(2-cyanopyrimidin-4-yl)amino]-N-[(1S)-2-(dimethylamino)-1-phenylethyl]-6,6-dimethyl-4,6-dihydropyrrolo[3,4-c]pyrazole-5(1H)-carboxamide<br>$^1$H NMR (CD$_3$OD) δ: 1.62 (s, 3 H), 1.70 (s, 3 H), 2.89 (s, 3 H), 2.97 (s, 3 H), 3.35-3.47 (m, 2 H), 4.68-4.88 (m, 2 H), 5.25-5.33 (m, 1 H), 6.83-6.92 (b, 1 H), 7.21-7.41 (m, 5 H), 8.20 (d, J = 7.12 Hz, 1 H). LCMS (APCI, M + H$^+$): 446.1. Anal. (C$_{23}$H$_{27}$N$_9$O•1.88TFA•0.15H$_2$O•0.04MeCN): C, H, N. HPLC-UV Detection: 94% purity<br>Method Example 54 using 4-chloropyrimidine-2-carbonitrile in place of 54i. |
| 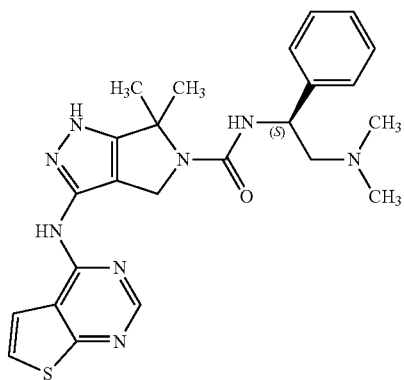<br>61 | N-[(1S)-2-(dimethylamino)-1-phenylethyl]-6,6-dimethyl-3-(thieno[2,3-d]pyrimidin-4-ylamino)-4,6-dihydropyrrolo[3,4-c]pyrazole-5(1H)-carboxamide.<br>R$_f$ = 0.18 (7% methanolic NH$_3$/CHCl$_3$). $^1$H NMR (400 MHz, CD$_3$OD): δ 1.70 (s, 3H), 1.77 (s, 3H), 2.32 (s, 6H), 2.42 (dd, J = 12.9, 4.5 Hz, 1H), 2.78-2.84 (m, 1H), 4.63 (d, J = 11.6 Hz, 1H), 4.71 (d, J = 11.3 Hz, 1H), 4.97-5.01 (m, 1H), 7.20-7.23 (m, 1H), 7.29-7.36 (m, 4H), 7.43 (d, J = 5.4 Hz, 1H), 8.12 (d, J = 5.3 Hz, 1H), 8.67 (s, 1H). LCMS 477 (M + H). Anal. (C$_{24}$H$_{28}$N$_8$OS•0.40 H$_2$O•0.40 MeOH) C, H, N. HPLC >98% purity.<br>Method of Example 54 using 4-Chlorothieno[2,3-c1]pyrimidine in place of 54i. |
| 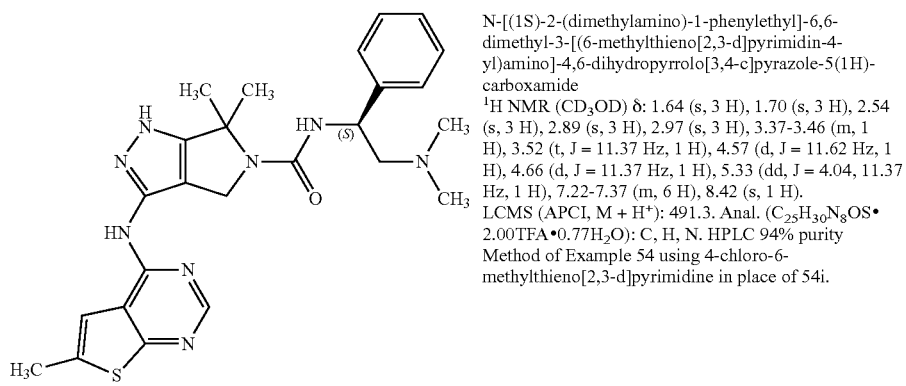<br>62 | N-[(1S)-2-(dimethylamino)-1-phenylethyl]-6,6-dimethyl-3-[(6-methylthieno[2,3-d]pyrimidin-4-yl)amino]-4,6-dihydropyrrolo[3,4-c]pyrazole-5(1H)-carboxamide<br>$^1$H NMR (CD$_3$OD) δ: 1.64 (s, 3 H), 1.70 (s, 3 H), 2.54 (s, 3 H), 2.89 (s, 3 H), 2.97 (s, 3 H), 3.37-3.46 (m, 1 H), 3.52 (t, J = 11.37 Hz, 1 H), 4.57 (d, J = 11.62 Hz, 1 H), 4.66 (d, J = 11.37 Hz, 1 H), 5.33 (dd, J = 4.04, 11.37 Hz, 1 H), 7.22-7.37 (m, 6 H), 8.42 (s, 1 H).<br>LCMS (APCI, M + H$^+$): 491.3. Anal. (C$_{25}$H$_{30}$N$_8$OS•2.00TFA•0.77H$_2$O): C, H, N. HPLC 94% purity<br>Method of Example 54 using 4-chloro-6-methylthieno[2,3-d]pyrimidine in place of 54i. |

| Structure and Example # | Chemical name, Analytical data and comments |
|---|---|
| 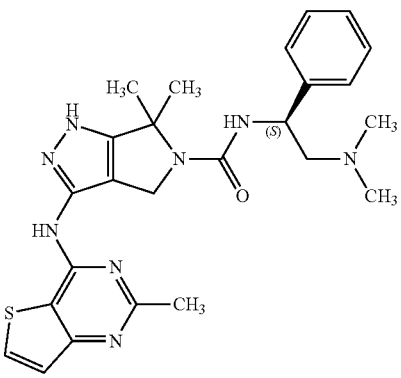<br>63 | N-[(1S)-2-(dimethylamino)-1-phenylethyl]-6,6-dimethyl-3-[(2-methylthieno[3,2-d]pyrimidin-4-yl)amino]-4,6-dihydropyrrolo[3,4-c]pyrazole-5(1H)-carboxamide<br>$R_f$ = 0.24 (7% methanolic $NH_3/CHCl_3$). $^1$H NMR (400 MHz, $CD_3OD$): δ 1.77 (s, 3H), 1.80 (s, 3H), 2.77 (s, 3H), 2.94 (s, 3H), 3.05 (s, 3H), 3.42-3.46 (m, 1H), 3.63-3.69 (m, 1H), 4.66 (s, 2H), 5.39 (dd, J = 11.4, 4.0 Hz), 7.33-7.47 (m, 6H), 8.42 (d, J = 5.3 Hz, 1H). LCMS 491 (M + H). Anal. ($C_{25}H_{30}N_8OS$•3.0 TFA•0.40 $H_2O$) C, H, N.<br>Method of Example 54 using 4-Chloro-2-methylthieno[3,2-d]pyrimidine in place of 54i. |
| 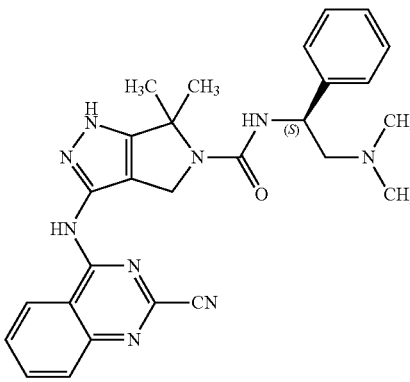<br>64 | 3-[(2-cyanoquinazolin-4-yl)amino]-N-[(1S)-2-(dimethylamino)-1-phenylethyl]-6,6-dimethyl-4,6-dihydropyrrolo[3,4-c]pyrazole-5(1H)-carboxamide.<br>$R_f$ = 0.29 (7% methanolic $NH_3/CHCl_3$). $^1$H NMR (400 MHz, $CH_3OD$): δ 1.71 (s, 3H), 1.77 (s, 3H), 2.35 (s, 6H), 2.36-2.37 (m, 1H), 2.79-2.85 (m, 1H), 4.91-5.00 (m, 3H), 7.21-7.24 (m, 1H), 7.31-7.35 (m, 2H), 7.38-7.40 (m, 2H), 7.76-7.80 (m, 1H), 7.91-7.92 (m, 1H), 7.95-7.99 (m, 1H), 8.42-8.43 (m, 1H). LCMS 496 (M + H). Anal. ($C_{27}H_{29}N_9O$•0.60 $H_2O$•0.10 hexane) C, H, N.<br>Method of Example 54 using 4-Chloroquinazoline-2-carbonitrile in place of 54i. |
| 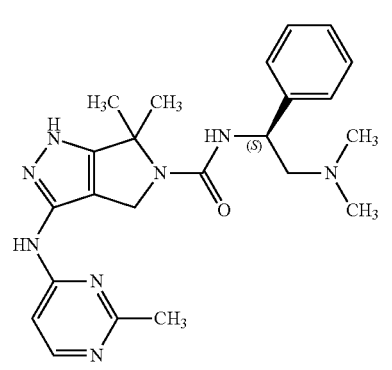<br>65 | N-[(1S)-2-(dimethylamino)-1-phenylethyl]-6,6-dimethyl-3-[(2-methylpyrimidin-4-yl)amino]-4,6-dihydropyrrolo[3,4-c]pyrazole-5(1H)-carboxamide<br>$^1$H NMR (400 MHz, DMSO) δ: 1.58 (m, 6 H), 2.42 (m, 6H), 4.65 (m, 2 H), 5.13 (m, 1H), 6.64 (m, 1H), 7.23-7.41 (m, 6 H), 8,14 (d, J = 3 Hz), 1H. APCI-MS: [M + H] 435.<br>Method of Example 54 using 4-chloro-2-methylpyrimidine in place of 54i. |
| 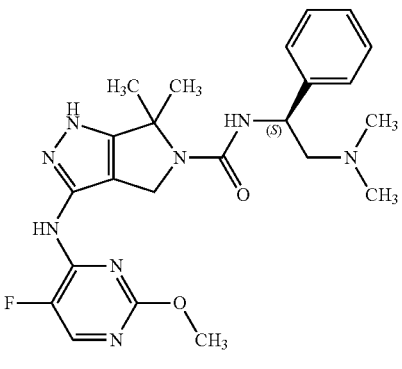<br>66 | N-[(1S)-2-(dimethylamino)-1-phenylethyl]-3-[(5-fluoro-2-methoxypyrimidin-4-yl)amino]-6,6-dimethyl-4,6-dihydropyrrolo[3,4-c]pyrazole-5(1H)-carboxamide.<br>$^1$H NMR (400 MHz, $CD_3OD$): δ 1.72 (s, 3H) 1.77 (s, 3H), 3.06 (s, 3H), 3.12 (s, 3H), 3.46-3.50 (m, 1H), 3.56-3.62 (m, 1H), 3.89 (s, 3H), 4.63-4.66 (m, 2H), 5.37-5.41 (m, 1H), 7.35-7.44 (m, 5H), 8.07 (d, J = 3.3 Hz, 1H). LCMS 469 (M + H). Anal. ($C_{23}H_{29}N_8OF$•2.25 TFA) C, H, N.<br>Method of Example 54 using 4-Chloro-5-fluoro-2-methoxypyrimidine in place of 54i. |

| Structure and Example # | Chemical name, Analytical data and comments |
|---|---|
| 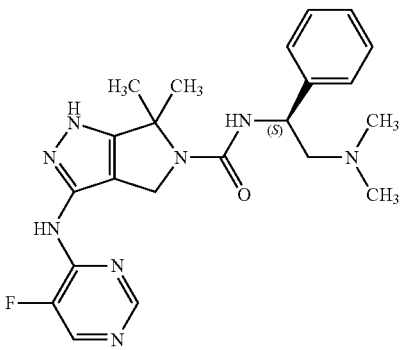 67 | N-[(1S)-2-(dimethylamino)-1-phenylethyl]-3-[(5-fluoropyrimidin-4-yl)amino]-6,6-dimethyl-4,6-dihydropyrrolo[3,4-c]pyrazole-5(1H)-carboxamide<br>$^1$H NMR (400 MHz, CD$_3$OD): δ 1.72 (s, 3H) 1.78 (s, 3H), 2.98 (s, 3H), 3.06 (s, 3H), 3.47-3.54 (m, 1H), 3.58-3.64 (m, 1H), 4.65 (d, J = 11.4 Hz, 1H), 4.74 (d, J = 11.4 Hz, 1H), 5.42 (dd, J = 11.4, 4.0 Hz, 1H), 7.33-7.36 (m, 1H), 7.39-7.44 (m, 4H), 8.32 (s, 1), 8.52 (s, 1H). LCMS 439 (M + H). Anal. (C$_{22}$H$_{27}$N$_8$OF•2.20 TFA•0.20 H$_2$O) C, H, N. HPLC = 91% purity Method of Example 54 using 4-Chloro-5-fluoropyrimidine in place of 54i. |

Example 68

(1S)-2-(dimethylamino)-1-phenylethyl 6,6-dimethyl-3-(thieno[3,2-d]pyrimidin-4-ylamino)-4,6-dihydropyrrolo[3,4-c]pyrazole-5(1H)-carboxylate

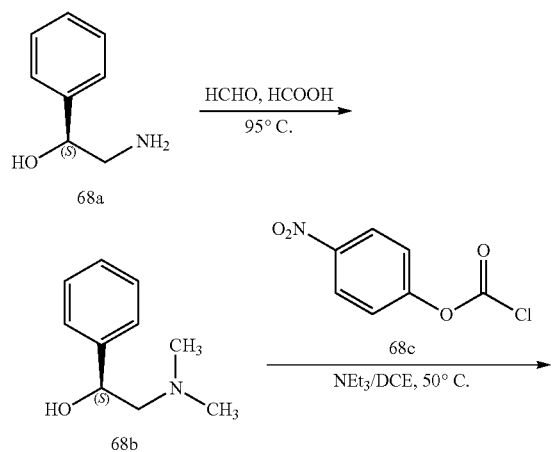

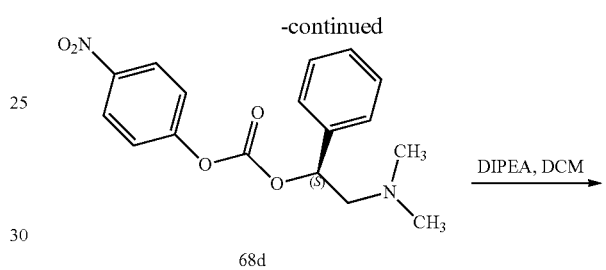

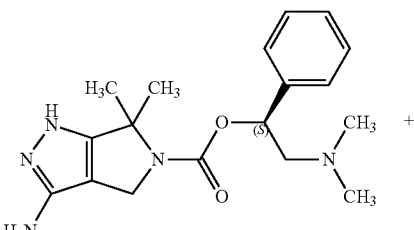

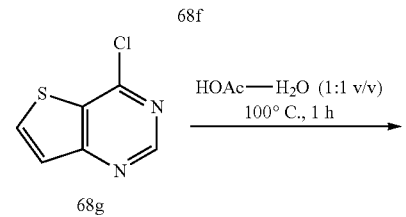

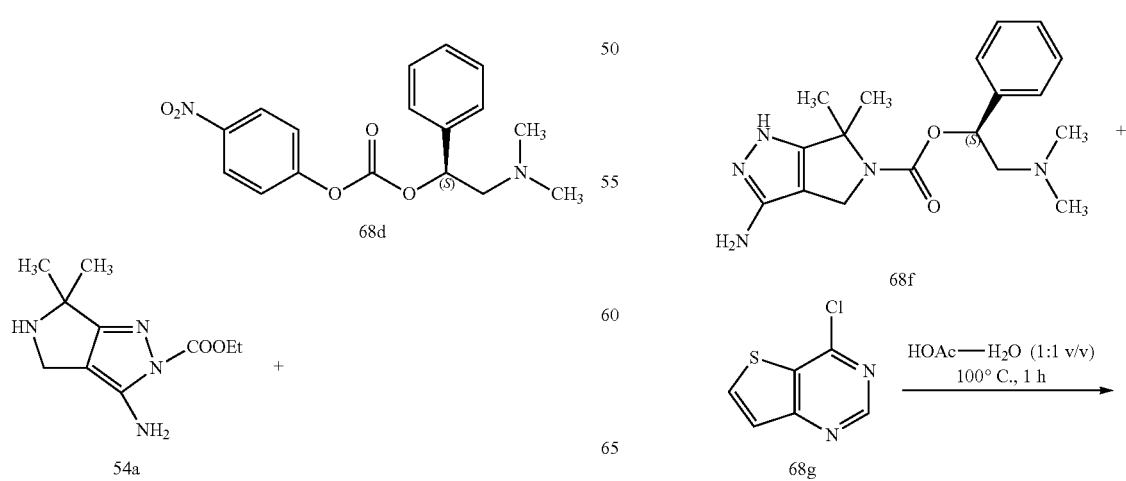

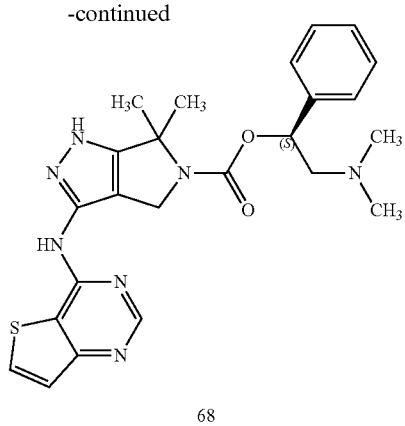

68

Preparation of Compound 68b:
(S)-2-dimethylamino-1-phenyl-ethanol

To a solution of (S)-(+)-2-amino-1-phenyl-ethanol (68a, 100.0 g, 729.0 mmol) in formic acid (400 mL) was added formaldehyde (800 mL, 37% wt in water) at room temperature. The solution was stirred at 95° C. overnight. After it was cooled to room temperature, conc. HCl was used to adjust the solution to pH=2. It was extracted with ether (3×500 mL) and then adjusted to pH=10 with solid NaOH. The resulting aqueous layer was extracted with $CH_2Cl_2$ (3×500 mL). The combined organic layers were dried over $Na_2SO_4$. Filtration and evaporation followed by flash chromatography (5% MeOH in $CH_2Cl_2$ to 4.5% MeOH/0.5% $NEt_3$ in $CH_2Cl_2$) gave compound 68b (S)-2-dimethylamino-1-phenyl-ethanol as a light-yellow oil (68.0 g, 56%). $^1$H NMR (300 MHz, $CDCl_3$) δ: 2.35 (s, 6H), 2.37 (m, 1H), 2.46 (dd, J=12.8, 9.2 Hz, 1H), 4.02 (br s, 1H), 4.69 (dd, J=10.5, 3.6 Hz, 1H), 7.22-7.4 (m, 5H).

Preparation of Compound 68e: (S)-5-(2-(dimethylamino)-1-phenylethyl) 2-ethyl 3-amino-6,6-dimethylpyrrolo[3,4-c]pyrazole-2,5(4H,6H)-dicarboxylate To a stirred solution of (S)-2-dimethylamino-1-phenylethanol (68b, 21.50 g, 130.0 mmol) in 1,2-dichloroethane (500 mL) was added triethylamine (26.30 g, 260.0 mmol) and 4-nitrophenyl chloroformate (68c, 27.00 g, 130.0 mmol) at room temperature under nitrogen. The solution was stirred at 50° C. overnight. A total of 16.8 g (130.0 mmol) of Hünig's base was then added, followed by ethyl 3-amino-6,6-dimethyl-5,6-dihydropyrrolo[3,4-c]pyrazole-1(4H)-carboxylate dihydrochloride salt (54a, 17.90 g, 60.25 mmol). The reaction mixture was stirred at 50° C. for another 12 h. It was diluted with dichloromethane (1.5 L) and washed with water (2×1.0 L) and brine (1.0 L), dried over $Na_2SO_4$. Another batch with the exact scale was also carried out. These two batches were combined together during workup. Filtration and evaporation followed by flash chromatography (4.75% MeOH/0.25% $NEt_3$/95% DCM) afforded compound 68e ethyl 3-amino-5-({[(1S)-2-(dimethylamino)-1-phenylethyl]hydroxy}carbonyl)-6,6-dimethyl-5,6-dihydropyrrolo[3,4-c]pyrazole-1(4H)-carboxylate as a light-yellow gummy oil (5.00 g, 10%). $^1$H NMR ($CDCl_3$, a mixture of rotamers, only the chemical shifts of the major form is reported) δ: 1.45 (t, J=7.1 Hz, 3H), 1.63 (s, 3H), 1.72 (s, 3H), 2.29 (s, 3H), 2.36 (s, 3H), 2.55-2.63 (m, 1H), 2.88 (dd, J=13, 8.3 Hz, 1H), 4.29 (q, J=13 Hz, 1H), 4.51 (q, J=7.1 Hz, 2H), 5.44 (d, J=10.7 Hz, 1H), 5.8-5.95 (m, 1H), 7.25-7.42 (m, 5H). LCMS (APCI, M+H$^+$) 416.

Preparation of Compound 68f: (S)-2-(dimethylamino)-1-phenylethyl 3-amino-6,6-dimethylpyrrolo[3,4-c]pyrazole-5(1H,4H,6H)-carboxylate A round bottom flask was charged with compound 68e (1.01 g, 0.242 mmol), 1N LiOH (3.87 ml, 1.6 eq) and methanol (24 ml). The resulting mixture was stirred at room temperature for 3 hours. Solvent was evaporated. To the residue were added ethyl acetate (20 ml) and water (20 ml). The water phase was separated and extracted with ethyl acetate (10 ml). The combined ethyl acetate phase was washed with brine, dried with anhydrous $Na_2SO_4$, filtered and evaporated to give the crude compound 68f (564 mg, 67%). LCMS (APCI, M+H$^+$): 344.1.

A re-sealable tube was charged with compound 68f (88 mg, 0.257 mmol), 4-chloro-thieno (3,2-d)-pyrimidine (88 mg, 2 eq), and a mixture of acetic acid and water (1 to 1, 1 ml). The tube was capped and stirred at 100° C. for 1 hour. It was then purified twice by prep. HPLC to give title compound 68 as a white solid (36 mg, 29% yield). $^1$H NMR ($CD_3OD$, a mixture of rotamers, only the chemical shifts of the major form is reported) δ: 1.55 (s, 3H), 1.66 (s, 3H), 2.62 (s, 6H), 2.82-2.92 (m, 1H), 3.21-3.37 (m, 1H), 4.44-4.57 (m, 1H), 4.60-4.69 (m, 1H), 5.90-6.00 (m, 1H), 7.22-7.43 (m, 6H), 8.01-8.09 (m, 1H), 8.55 (s, 1H). LCMS (APCI, M+H$^+$): 478.2. Anal. ($C_{24}H_{27}N_7O_2S$.0.2HOAc.0.45TFA.0.98$H_2O$): C, H, N.

| Structure and Example # | Chemical name, Analytical data and comments |
|---|---|
| ![structure 69] 69 | (1S)-2-(dimethylamino)-1-phenylethyl 6,6-dimethyl-3-[(2-methylthieno[2,3-d]pyrimidin-4-yl)amino]-4,6-dihydropyrrolo[3,4-c]pyrazole-5(1H)-carboxylate $^1$H NMR (400 MHz, DMSO-$d_6$) δ: 1.55 (s, 3H), 1.67 (s, 3H), 2.63 (s, 3H), 2.87 (d, J = 4.8 Hz, 3H), 2.93 (d, J = 5 Hz, 3H), 3.46 (m, 1H), 3.60 (m, 1H), 3.84 (d, J = 13.1 Hz, 1H), 3.97 (d, J = 13.1 Hz, 1H), 6.13 (dd, J = 10.7, 2.3 Hz, 1H), 7.35-7.50 (m, 5H), 7.58 (d, J = 6.1 Hz, 1H), 7.87 (d, j = 6 Hz, 1H), 9.49 (br s, 1H), 10.45 (s, 1H), LCMS [M + H]$^+$ 492 Anal ($C_{25}H_{29}N_7O_2S$•1.8$H_2O$•0.44TFA•0.4HOAc) C, H, N, S. Method of Example 68 using 4-chloro-2-methylthieno[2,3-d]pyrimidine in place of 68g. |

| Structure and Example # | Chemical name, Analytical data and comments |
|---|---|
| 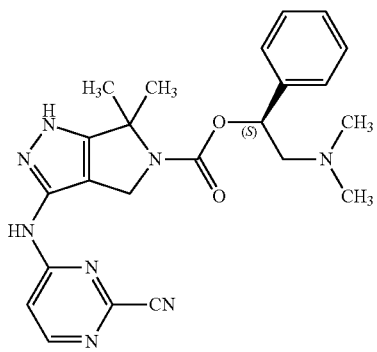<br>70 | (1S)-2-(dimethylamino)-1-phenylethyl 3-[(2-cyano pyrimidin-4-yl)amino]-6,6-dimethyl-4,6-dihydropyrrolo [3,4-c]pyrazole-5(1H)-carboxylate<br>$^1$H NMR (CD$_3$OD) δ: 1.49 (s, 3 H), 1.64 (s, 3 H), 2.93 (s, 3 H), 2.97 (s, 3 H), 3.30-3.39 (m, 1 H), 3.59-3.70 (m, 1 H), 4.92 (d, J = 13.39 Hz, 1 H), 5.14 (d, J = 13.39 Hz, 1 H), 6.03 (dd, J = 2.27, 10.86 Hz, 1 H), 6.86 (d, J = 6.06 Hz, 1 H), 6.86 (d, J = 6.06 Hz, 1 H), 7.25-7.44 (m, 5 H), 8.19-8.25 (m, 1 H). LCMS (APCI, M + H$^+$): 447.1. Anal. (C23H26N8O$_2$•1.91TFA): C, H, N. HPLC-UV Detection: >95% purity.<br>Method of Example 68 using 4-chloropyrimidine-2-carbonitrile in place of 68g. |
| 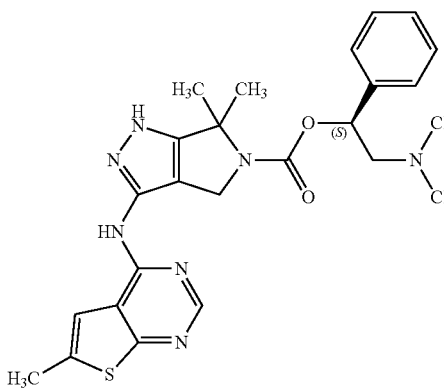<br>71 | (1S)-2-(dimethylamino)-1-phenylethyl 6,6-dimethyl-3-[(6-methylthieno[2,3-d]pyrimidin-4-yl)amino]-4,6-dihydropyrrolo[3,4-c]pyrazole-5(1H)-carboxylate<br>$^1$H NMR (CD$_3$OD, a mixture of rotamers, only the chemical shifts of the major form is reported) δ: 1.55 (s, 3 H), 1.66 (s, 3 H), 2.55 (s, 3 H), 2.92 (s, 3 H), 2.99 (s, 3 H), 3.33-3.46 (m, 1 H), 3.64-3.81 (m, 1 H), 4.63-4.80 (m, 2 H), 6.04-6.14 (m, 1 H), 7.22-7.45 (m, 6 H), 8.41 (s, 1 H). LCMS (APCI, M + H$^+$): 492.3. Anal. (C$_{25}$H$_{29}$N$_7$O$_2$S• 1.74TFA•0.58H$_2$O): C, H, N. HPLC-UV Detection: 93% purity.<br>Method of Example 68 using 4-chloro-6-methylthieno [2,3-d]pyrimidine in place of 68g. |
| 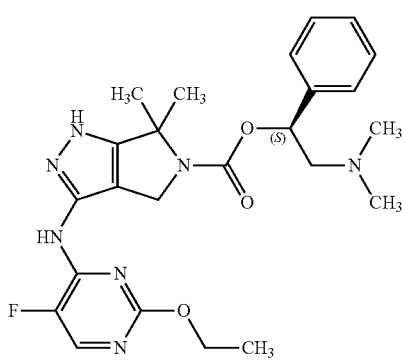<br>72 | (1S)-2-(dimethylamino)-1-phenylethyl 3-[(2-ethoxy-5-fluoropyrimidin-4-yl)amino]-6,6-dimethyl-4,6-dihydro-pyrrolo[3,4-c]pyrazole-5(1H)-carboxylate.<br>$^1$H NMR (CD$_3$OD, a mixture of rotamers, only the chemical shifts of the major form is reported) δ: 1.25 (t, J = 7.07 Hz, 3 H), 1.54 (s, 3 H), 1.65 (s, 3 H), 2.91 (s, 3 H), 2.98 (s, 3 H), 3.36-3.44 (m, 1 H), 3.58-3.69 (m, 1 H), 4.25 (q, J = 7.07 Hz, 2 H), 4.70 (s, 2 H), 6.07-6.15 (m, 1 H), 7.28-7.43 (m, 5 H), 7.97 (d, J = 3.28, 1 H). LCMS (APCI, M + H$^+$): 484.2. Anal. (C$_{24}$H$_{30}$FN$_7$O$_3$•2.06TFA•0.31H$_2$O): C, H, N; HPLC-UV Detection: 100% purity.<br>Method of Example 68 using 4-chloro-2-ethoxy-5-fluoropyrimidine in place of 68g. |

| Structure and Example # | Chemical name, Analytical data and comments |
|---|---|
| 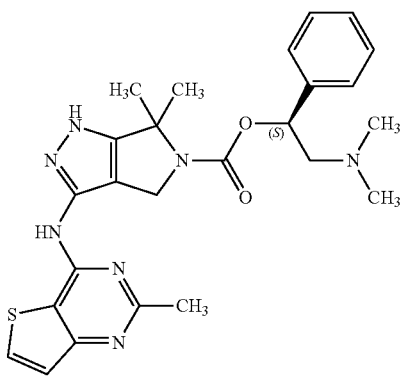<br>73 | (1S)-2-(dimethylamino)-1-phenylethyl 6,6-dimethyl-3-[(2-methylthieno[3,2-d]pyrimidin-4-yl)amino]-4,6-dihydropyrrolo[3,4-c]pyrazole-5(1H)-carboxylate<br>$^1$H NMR (400 MHz, CD$_3$OD): δ 1.67 (s, 3H), 1.78 (s, 3H), 2.79 (s, 3H), 3.07 (s, 6H), 3.48 (dd, J = 13.9, 2.5 Hz, 1H), 3.80 (dd, J = 13.6, 10.6 Hz, 1H), 4.71-4.99 (m, 2H), 6.21-6.22 (m, 1H), 7.39-7.58 (m, 6H), 8.42 (d, J = 5.5 Hz, 1H). LCMS 492 (M + H). Anal. (C$_{25}$H$_{29}$N$_7$O$_2$S•2.75 TFA) C, H, N.<br>Method of Example 73 using 4-Chloro-2-methylthieno[3,2-d]pyrimidine in place of 68g. |
| 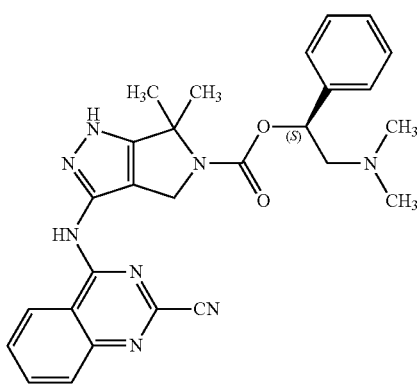<br>74 | (1S)-2-(dimethylamino)-1-phenylethyl 3-[(2-cyanoquinazolin-4-yl)amino]-6,6-dimethyl-4,6-dihydropyrrolo[3,4-c]pyrazole-5(1H)-carboxylate.<br>$^1$H NMR (400 MHz, CD$_3$OD): δ 1.62 (s, 3H), 1.77 (s, 3H), 3.03 (s, 3H), 3.07 (s, 3H), 3.42-3.46 (m, 1H), 3.76-3.82 (m, 1H), 5.13 (d, J = 13.3 Hz, 1H), 5.36 (d, J = 13.3 Hz, 1H), 6.14 (dd, J = 11.1, 2.3 Hz, 1H) 7.36-7.46 (m, 3H), 7.52-7.54 (m, 2H), 7.78-7.82 (m, 1H), 7.92 (d, J = 8.3 Hz, 1H), 7.97-8.01 (m, 1H), 8.45 (d, J = 8.3 Hz, 1H). LCMS 497 (M + H). Anal. (C$_{27}$H$_{28}$N$_8$O$_2$•1.9 TFA•0.25 water) C, H, N.<br>Method of Example 68 using 4-Chloroquinazoline-2-carbonitrile in place of 68g. |
| 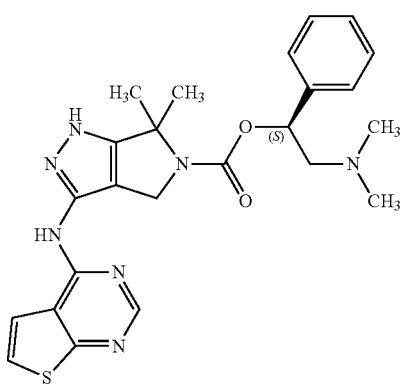<br>75 | (1S)-2-(dimethylamino)-1-phenylethyl 6,6-dimethyl-3-(thieno[2,3-d]pyrimidin-4-ylamino)-4,6-dihydropyrrolo[3,4-c]pyrazole-5(1H)-carboxylate.<br>R$_f$ = 0.26 (7% methanolic NH$_3$/CHCl$_3$).<br>$^1$H NMR (400 MHz, CD$_3$CN): δ 1.59 (s, 3H), 1.68 (s, 3H), 2.28 (s, 6H), 2.51-2.58 (m, 1H), 2.77-2.82 (m, 1H), 4.70 (s, 2H), 5.80-5.86 (m, 1H), 7.27-7.46 (m, 5H), 8.01-8.04 (m, 1H), 8.58 (br, 1H), 8.68 (d, J = 8.5 Hz, 1H). LCMS 478 (M + H). Anal. (C$_{24}$H$_{27}$N$_7$O$_2$S•0.06 TFA•0.10 hexane) C, H, N. HPLC >99% purity.<br>Method of Example 68 using 4-Chlorothieno[2,3-d]pyrimidine in place of 68g. |

| Structure and Example # | Chemical name, Analytical data and comments |
|---|---|
| 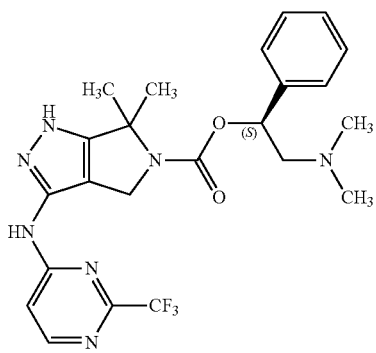<br>76 | (1S)-2-(dimethylamino)-1-phenylethyl 6,6-dimethyl-3-{[2-(trifluoromethyl)pyrimidin-4-yl]amino}-4,6-dihydropyrrolo[3,4-c]pyrazole-5(1H)-carboxylate<br>$^1$H NMR (400 MHz, DMSO) δ: 1.58 (m, 6 H), 2.22 (m, 6H), 4.76 (m, 1 H), 5.79 (m, 1H), 7.29-7.40 (m, 5 H).<br>APCI-MS: [M + H] 490.<br>Method of Example 68 using 4-chloro-2-(trifluoromethyl)pyrimidine in place of 68g. |
| 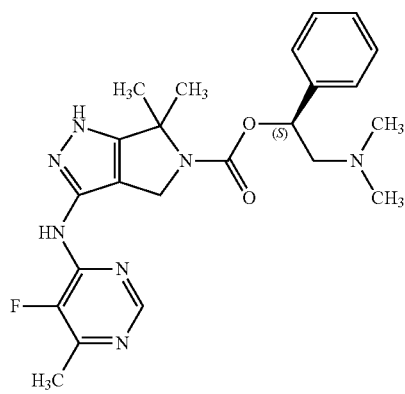<br>77 | (1S)-2-(dimethylamino)-1-phenylethyl 3-[(5-fluoro-6-methylpyrimidin-4-yl)amino]-6,6-dimethyl-4,6-dihydropyrrolo[3,4-c]pyrazole-5(1H)-carboxylate<br>$^1$H NMR (CD$_3$OD, a mixture of rotamers, only the chemical shifts of the major form is reported) δ: 1.52 (s, 3 H), 1.63 (s, 3 H), 2.28-2.36 (m, 1 H), 2.34 (s, 3 H), 2.39 (s, 3 H), 2.52 (s, 3 H), 2.68-2.83 (m, 1 H), 4.43-4.65 (m, 2 H), 5.84-5.95 (m, 1 H), 7.18-7.41 (m, 5 H), 8.25 (s, 1 H). LCMS (APCI, M + H$^+$): 454.2. Anal. (C$_{23}$H$_{28}$FN$_7$O$_2$•0.45TFA•0.40HOAc•0.20H$_2$O) C, H, N. HPLC-UV Detection: 100% purity.<br>Method of Example 68 using 4-chloro-5-fluoro-6-methylpyrimidine in place of 68g. |
| 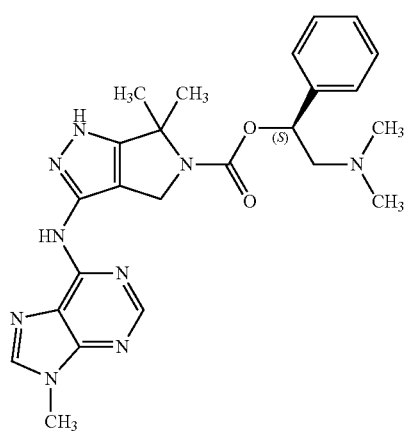<br>78 | (1S)-2-(dimethylamino)-1-phenylethyl 6,6-dimethyl-3-[(9-methyl-9H-purin-6-yl)amino]-4,6-dihydropyrrolo[3,4-c]pyrazole-5(1H)-carboxylate<br>$^1$H NMR (CD$_3$OD, a mixture of rotamers, only the chemical shifts of the major form is reported) δ: 1.55 (s, 3 H), 1.67 (s, 3 H), 2.94 (s, 3 H), 3.00 (s, 3 H), 3.36-3.43 (m, 1 H), 3.69-3.78 (m, 1 H), 3.81 (s, 1 H), 4.72-4.81 (m, 2 H), 6.07-6.12 (m, 1 H), 7.29-7.44 (m, 5 H), 8.14 (s, 1 H), 8.44 (s, 1 H). LCMS (APCI, M + H$^+$): 476.2. Anal. (C$_{24}$H$_{29}$N$_9$O$_2$•1.87TFA•0.73H$_2$O): C, H, N. HPLC-UV Detection: 100% purity.<br>Method of Example 78 using 6-chloro-9-methyl-9H-purine in place of 68g. |

| Structure and Example # | Chemical name, Analytical data and comments |
|---|---|
| 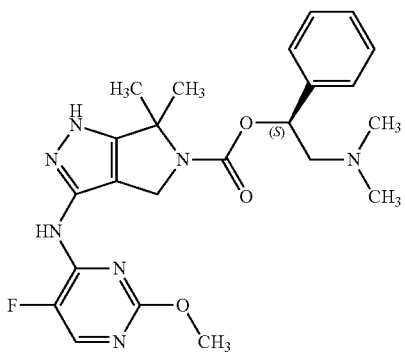 79 | (1S)-2-(dimethylamino)-1-phenylethyl 3-[(5-fluoro-2-methoxypyrimidin-4-yl)amino]-6,6-dimethyl-4,6-dihydropyrrolo[3,4-c]pyrazole-5(1H)-carboxylate. $^1$H NMR (400 MHz, CD$_3$OD): δ 1.62 (s, 3H), 1.73 (s, 3H), 3.02 (s, 3H), 3.09 (s, 3H), 3.47-3.50 (m, 1H), 3.72-3.78 (m, 1H), 3.93 (s, 3H), 4.58-4.61 (m, 2H), 6.18-6.20 (m, 1H), 7.41-7.57 (m, 5H), 8.07 (d, J = 3.0 Hz, 1H). LCMS 470 (M + H). Anal. (C$_{23}$H$_{28}$N$_7$O$_3$F•2.30 TFA•0.25 H$_2$O) C, H, N. HPLC >99% purity. Method of Example 68 using 4-Chloro-5-fluoro-2-methoxypyrimidine in place of 68g. |
| 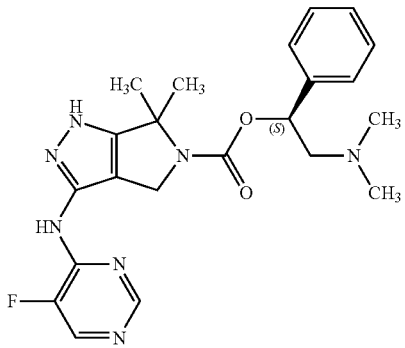 80 | (1S)-2-(dimethylamino)-1-phenylethyl 3-[(5-fluoropyrimidin-4-yl)amino]-6,6-dimethyl-4,6-dihydropyrrolo[3,4-c]pyrazole-5(1H)-carboxylate. $^1$H NMR (400 MHz, CH$_3$OD): δ 1.61 (s, 3H), 1.71 (s, 3H), 2.35 (s, 3H), 2.42 (s, 3H), 2.55-2.65 (m, 1H), 3.08-3.11 (m, 1H), 4.93-4.98 (m, 2H), 5.87-5.96 (m, 1H), 7.28-7.45 (m, 5H), 8.28 (br, 1H), 8.48 (br, 1H). LCMS 440 (M + H). Anal. (C$_{22}$H$_{26}$N$_7$O$_2$F•0.70 H$_2$O•0.30 hexane) C, H, N. PLC = 90% purity. Method of Example 68 using 4-Chloro-5-fluoropyrimidine in place of 68g. |

Example 81

N-(6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-yl)-7-methylthieno[3,2-d]pyrimidin-4-amine

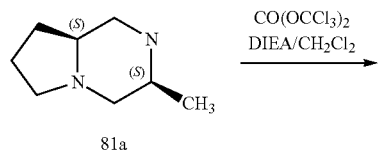

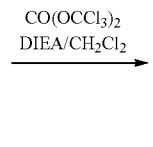

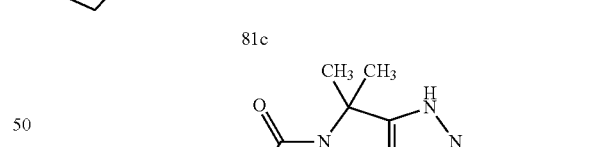

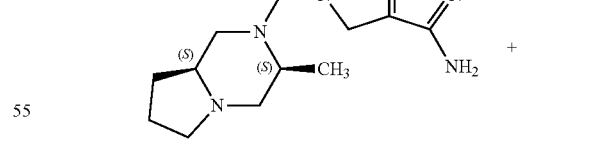

-continued

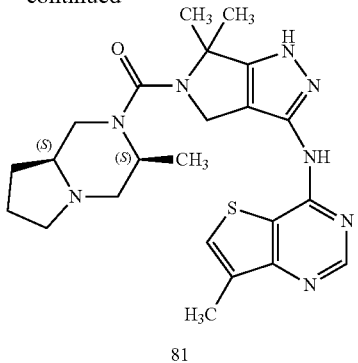

81

Preparation of compound 81b: (3S,8aS)-3-methyl-hexahydropyrrolo[1,2-a]pyrazine-2(1H)-carbonyl chloride To a stirring mixture of triphosgene (2.11 g, 1 eq) in CH$_2$Cl$_2$ (10 ml) at 0° C. was added DIPEA (1.8 ml, 1.5 eq) and (3S,8aS)-3-methyloctahydropyrrolo[1,2-a]pyrazine (81a, 1 g, 7.13 mmol). The resulting mixture was stirred at 0° C. for 30 min. The reaction mixture was evaporated in vacuo to give a residue, compound 81b, which was directly carried onto the next reaction without further purification.

Preparation of Compound 81c: ethyl 3-amino-6,6-dimethyl-5-{[(3S,8aS)-3-methylhexahydropyrrolo[1,2-a]pyrazin-2(1H)-yl]carbonyl}-5,6-dihydropyrrolo[3,4-c]pyrazole-2(4H)-carboxylate To a stirring mixture of compound I(H) 5-tert-butyl 2-ethyl 3-amino-6,6-dimethylpyrrolo[3,4-c]pyrazole-2,5(4H,6H)-dicarboxylate (5.65 g, 17.4 mmol) in CH$_2$Cl$_2$ (20 ml) was added 4.0M HCl in dioxane (30 ml). The reaction mixture was concentrated in vacuo to give crude HCl salt of compound 54a. A portion of residue (54a, 1 g, 4.46 mmol) was added to a stirring mixture of (3S,8aS)-3-methylhexahydropyrrolo[1,2-a]pyrazine-2(1H)-carbonyl chloride (81b, 1.4 g, 2 eq) in CH$_2$Cl$_2$ (20 ml), DIPEA (1.2 ml, 2 eq). The resulting mixture was stirred at room temperature for 15 h. The reaction mixture was diluted with CH$_2$Cl$_2$, and washed with saturated NaHCO$_3$, dried over sodium sulfate, concentrated in vacuo, purified by flash chromatography. Elution with 5-15% MeOH/DCM provided compound 81c. $^1$H NMR (CD$_3$)$_2$SO δ: 1.2 (m, 2H), 1.31 (t, 3H), 1.52 (m, 6H), 1.64 (m, 4H), 1.93 (m, 1H), 2.18 (m, 1H), 2.77 (m, 2H), 2.93 (m, 1H), 3.77 (m, 1H), 4.18 (m, 2H), 4.33 (m, 2H)

Preparation of Compound 81d: 6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-amine To a stirring solution of ethyl 3-amino-6,6-dimethyl-5-{[(3S,8aS)-3-methyl hexahydropyrrolo[1,2-a]pyrazin-2(1H)-yl]carbonyl}-5,6-dihydropyrrolo[3,4-c]pyrazole-2(4H)—carboxylate (81c, 613 mg, 1.60 mmol) in MeOH (3 mL) was added 20% aq. NaOH (2 ml). The resulting mixture was stirred at room temperature for 30 min. The reaction mixture was concentrated and the residue was partitioned between ethyl acetate and saturated NaHCO$_3$, dried, and concentrated to give compound 81d.

To a stirring solution of compound 81d (0.150 g, 0.47 mmol) in 50% acetic acid/water (4 ml) was added 4-chloro-7-methylthieno[3,2-d]pyrimidine (175 mg, 2 eq). The resulting mixture was heated to a temperature of 100° C. for 1 hr. The reaction mixture was purified by prep-HPLC to provide compound 81 as a white solid $^1$H NMR (CD$_3$)$_2$SO δ: 1.23 (m, 2H), 1.62 (d, 6H), 1.69 (m, 3H), 1.83 (m, 1H), 1.95 (m, 1H), 2.16 (m, 1H), 2.34 (s, 3H), 2.74 (m, 2H), 2.90 (m, 1H), 3.80 (m, 1H), 4.52 (s, 2H), 7.83 (s, 1H), 8.56 (s, 1H).

| Structure and Example # | Chemical name, Analytical data and comments |
|---|---|
| 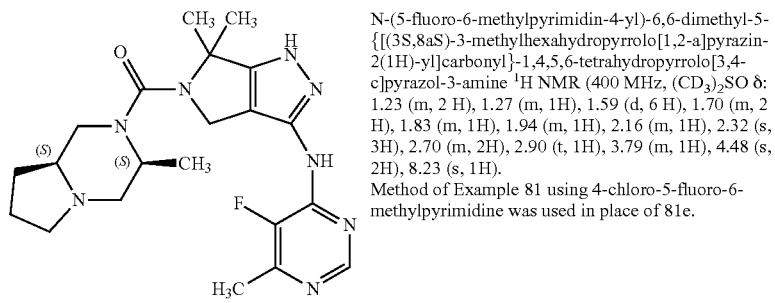<br>82 | N-(5-fluoro-6-methylpyrimidin-4-yl)-6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-amine $^1$H NMR (400 MHz, (CD$_3$)$_2$SO δ: 1.23 (m, 2 H), 1.27 (m, 1H), 1.59 (d, 6 H), 1.70 (m, 2 H), 1.83 (m, 1H), 1.94 (m, 1H), 2.16 (m, 1H), 2.32 (s, 3H), 2.70 (m, 2H), 2.90 (t, 1H), 3.79 (m, 1H), 4.48 (s, 2H), 8.23 (s, 1H).<br>Method of Example 81 using 4-chloro-5-fluoro-6-methylpyrimidine was used in place of 81e. |

More Examples

| Structure and Example # | Chemical name, Analytical data and comments |
|---|---|
| 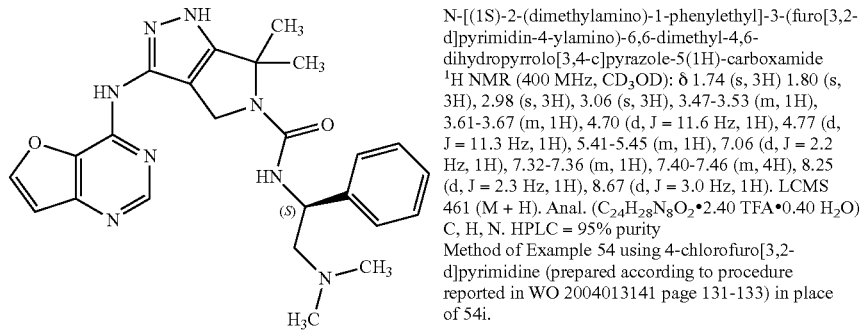<br>83 | N-[(1S)-2-(dimethylamino)-1-phenylethyl]-3-(furo[3,2-d]pyrimidin-4-ylamino)-6,6-dimethyl-4,6-dihydropyrrolo[3,4-c]pyrazole-5(1H)-carboxamide<br>$^1$H NMR (400 MHz, CD$_3$OD): δ 1.74 (s, 3H) 1.80 (s, 3H), 2.98 (s, 3H), 3.06 (s, 3H), 3.47-3.53 (m, 1H), 3.61-3.67 (m, 1H), 4.70 (d, J = 11.6 Hz, 1H), 4.77 (d, J = 11.3 Hz, 1H), 5.41-5.45 (m, 1H), 7.06 (d, J = 2.2 Hz, 1H), 7.32-7.36 (m, 1H), 7.40-7.46 (m, 4H), 8.25 (d, J = 2.3 Hz, 1H), 8.67 (d, J = 3.0 Hz, 1H). LCMS 461 (M + H). Anal. (C$_{24}$H$_{28}$N$_8$O$_2$•2.40 TFA•0.40 H$_2$O) C, H, N. HPLC = 95% purity<br>Method of Example 54 using 4-chlorofuro[3,2-d]pyrimidine (prepared according to procedure reported in WO 2004013141 page 131-133) in place of 54i. |
| 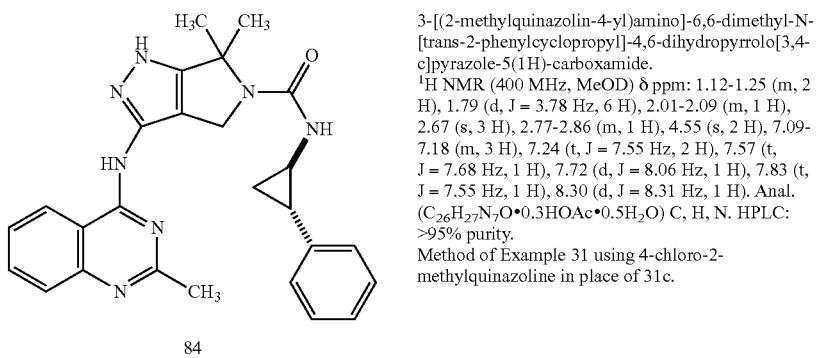<br>84 | 3-[(2-methylquinazolin-4-yl)amino]-6,6-dimethyl-N-[trans-2-phenylcyclopropyl]-4,6-dihydropyrrolo[3,4-c]pyrazole-5(1H)-carboxamide.<br>$^1$H NMR (400 MHz, MeOD) δ ppm: 1.12-1.25 (m, 2 H), 1.79 (d, J = 3.78 Hz, 6 H), 2.01-2.09 (m, 1 H), 2.67 (s, 3 H), 2.77-2.86 (m, 1 H), 4.55 (s, 2 H), 7.09-7.18 (m, 3 H), 7.24 (t, J = 7.55 Hz, 2 H), 7.57 (t, J = 7.68 Hz, 1 H), 7.72 (d, J = 8.06 Hz, 1 H), 7.83 (t, J = 7.55 Hz, 1 H), 8.30 (d, J = 8.31 Hz, 1 H). Anal. (C$_{26}$H$_{27}$N$_7$O•0.3HOAc•0.5H$_2$O) C, H, N. HPLC: >95% purity.<br>Method of Example 31 using 4-chloro-2-methylquinazoline in place of 31c. |
| 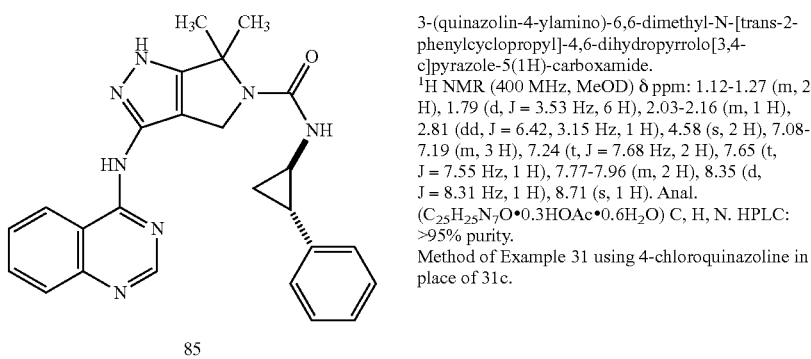<br>85 | 3-(quinazolin-4-ylamino)-6,6-dimethyl-N-[trans-2-phenylcyclopropyl]-4,6-dihydropyrrolo[3,4-c]pyrazole-5(1H)-carboxamide.<br>$^1$H NMR (400 MHz, MeOD) δ ppm: 1.12-1.27 (m, 2 H), 1.79 (d, J = 3.53 Hz, 6 H), 2.03-2.16 (m, 1 H), 2.81 (dd, J = 6.42, 3.15 Hz, 1 H), 4.58 (s, 2 H), 7.08-7.19 (m, 3 H), 7.24 (t, J = 7.68 Hz, 2 H), 7.65 (t, J = 7.55 Hz, 1 H), 7.77-7.96 (m, 2 H), 8.35 (d, J = 8.31 Hz, 1 H), 8.71 (s, 1 H). Anal. (C$_{25}$H$_{25}$N$_7$O•0.3HOAc•0.6H$_2$O) C, H, N. HPLC: >95% purity.<br>Method of Example 31 using 4-chloroquinazoline in place of 31c. |
| 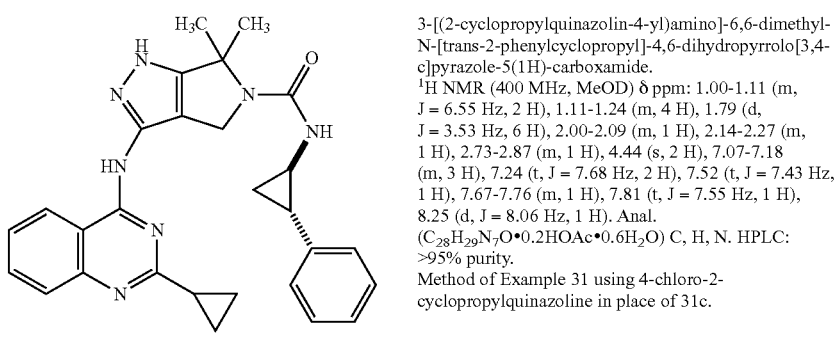<br>86 | 3-[(2-cyclopropylquinazolin-4-yl)amino]-6,6-dimethyl-N-[trans-2-phenylcyclopropyl]-4,6-dihydropyrrolo[3,4-c]pyrazole-5(1H)-carboxamide.<br>$^1$H NMR (400 MHz, MeOD) δ ppm: 1.00-1.11 (m, J = 6.55 Hz, 2 H), 1.11-1.24 (m, 4 H), 1.79 (d, J = 3.53 Hz, 6 H), 2.00-2.09 (m, 1 H), 2.14-2.27 (m, 1 H), 2.73-2.87 (m, 1 H), 4.44 (s, 2 H), 7.07-7.18 (m, 3 H), 7.24 (t, J = 7.68 Hz, 2 H), 7.52 (t, J = 7.43 Hz, 1 H), 7.67-7.76 (m, 2 H), 7.81 (t, J = 7.55 Hz, 1 H), 8.25 (d, J = 8.06 Hz, 1 H). Anal. (C$_{28}$H$_{29}$N$_7$O•0.2HOAc•0.6H$_2$O) C, H, N. HPLC: >95% purity.<br>Method of Example 31 using 4-chloro-2-cyclopropylquinazoline in place of 31c. |

Biological Testing, Ki Data and Cellular Assay Data

Cloning, expression, and purification of recombinant PAK4 Kinase domain (PAK4 KD): The cDNA coding for PAK4 was amplified from the EST clone (#12) (purchased from Research Genetics) by using PCR. P33 (ACATATG TCC CATGAGCAGT TCCGGGCTGC CCTGCAGCT) and P34 (CTCA TGGGTGCTTC AGCAGCTCGG CTGC-CGTGGC) were used as the 5' primer and 3' primer in PCR respectively. The PCR amplified product was cloned into Topo vector (Invitrogen Inc.), and verified by DNA sequencing. PAK4 KD was then subcloned into expression plasmid pET28a(+), pET24a(+), or pGST4.5. The recombinant plasmids containing PAK4 KD was transformed into BL21(DE3) cells for recombinant protein expression. The production of PAK4 KD was induced at 27° C. by the addition of IPTG into the cells. The cells were then harvested and lyzed for protein purification. Ni-NTA column (pET28a(+), pET24a(+)) and glutathione column (pGST4.5) were used for the purification. The purified protein was then subjected to thrombin to cleave the N-terminal tags that were inherited from the expression plasmids, and thus gave the PAK4 KD that were used for the Ki assay of this invention.

PAK4 kinase domain enzymatic assay conditions: the enzymatic activity of PAK4 KD was measured by its ability to catalyze the transfer of a phosphate residue from a nucleoside triphosphate to an amino acid side chain of a commercially available peptide (amino acid sequence EVPRRKSLVGT-PYWM). The conversion of ATP to ADP accompanies the catalytic reaction. The PAK4 KD catalyzed production of ADP from ATP was coupled to the oxidation of NADH through the activities of pyruvate kinase (PK) and lactate dehydrogenase (LDH). The conversion of NADH to $NAD^+$ is monitored by the decrease in absorbance at 340 nm ($e340=6.22$ $cm^{-1}mM^{-1}$) using a Molecular Devices SPECTRAMAX 190 in conjunction with the Biomec FX. Typical reaction solutions contain 2 mM phosphoenolpyruvate, 0.35 mM NADH, 10 mM $MgCl_2$, 1 mM DTT, 0.4 mM peptide (EVPRRKSLVGTPYWM) 0.04 mM ATP, 1 units/mL PK, 1 units/mL LDH, 0.01% Tween 20 in 50 mM HEPES, pH 7.5. Assays are initiated with the addition of 25 nM PAK4 KD. The PAK KD Ki of each compound of the invention (the inhibitor) was calculated based on multiple of Percent Inhibition numbers of the inhibitor at different inhibitor concentrations. The peptide (amino sequence EVPRRKSLVGT-PYWM) was purchased from American Peptide Company. NADH, $MgCl_2$, HEPES, DTT, ATP and PK/LDH were purchased from Sigma. Tween 20 was purchased from Calbiochem.

A sandwich ELISA method was used to measure the PAK4 kinase activity in whole cells. The level of PAK4-dependent phosphorylation of GEF-H1b can be determined by monitoring the binding of a phosphospecific antibody to GEF-H1b. A modified HEK 293 cell line is used in the bioassay and it has been engineered to overexpress both GEF-H1b and the kinase domain (KD) of PAK4. The KD of PAK4 is inducible in this cell line by tetracycline (Trex system, Invitrogen). The name of this cell line has been designated TR-293-KDG. To establish a phosphorylation event on GEF-H1, cells are induced with doxycycline to express the PAK4 KD. Negative control wells do not receive induction. Candidate substance effect is measured as the ability to block this phosphorylation event.

ELISA plate was prepared by pre-coating the plates with a capture antibody (α-HA-tag mouse monoclonal antibody), blocked with BSA, and washed in 0.1% tween 20 in tris-buffered saline (TBST). Tissue culture plates (precoated with poly-D-lysine) were seeded with TR-293-KDG cells. The TR-293-KDG Cells were induced to express the PAK4 KD with doxycycline overnight and subsequently & concomitantly treated with candidate substances or diluent for an additional 3-hour, continuous exposure. Cells were then lysed with a modified RIPA buffer supplemented with protease inhibitors. The fresh whole cell lysates were then added to the ELISA plate for 2-hours. Between all subsequent steps plates were washed 4 times with TBST. Detection antibody (recognizing the phospho-specific eptitope on GEF-H1b) was added for 1 hour, followed by addition of an enzyme linked goat α-rabbit secondary antibody for 45 minutes. Color development of the enzyme-linked antibody was performed with a peroxidase substrate, ABTS (Moss, Inc.) with absorbance at 405 nM read with a spectrophotometer after 30 minute incubation. EC50 values were calculated by sigmoid curve fitting using a four-parameter analysis.

PAK4 Kinase Domain Ki Data and PAK4 Cellular Assay EC50 Data of the Compounds of Examples 1-86:

| Ex. # | Ki data (uM) | EC50 (nM) |
|---|---|---|
| 1 | 0.041 | >2000 |
| 2 | 0.014 | 36 |
| 3 | 0.011 | 16 |
| 4 | 0.11 | |
| 5 | 0.22 | 87 |
| 6 | 0.0028 | 0.94 |
| 7 | 0.087 | >4000 |
| 8 | 0.61 | |
| 9 | 0.27 | >4000 |
| 10 | 0.12 | >4000 |
| 11 | 0.96 | |
| 12 | 0.038 | 78 |
| 13 | N/A | >4000 |
| 14 | 0.27 | |
| 15 | 0.090 | 500 |
| 16 | 0.076 | 1267 |
| 17 | 0.77 | |
| 18 | 0.34 | |
| 19 | 0.19 | |
| 20 | 0.090 | 1199 |
| 21 | 0.24 | |
| 22 | 0.72 | |
| 23 | 0.14 | >4000 |
| 24 | 0.64 | |
| 25 | 0.78 | |
| 26 | 0.22 | |
| 27 | 0.20 | |
| 28 | 0.27 | |
| 29 | 0.66 | |
| 30 | 0.080 | 968 |
| 31 | 0.020 | 103 |
| 32 | 0.0035 | 19 |
| 33 | 0.047 | 618 |
| 34 | 0.021 | 778 |
| 35 | 0.26 | 262 |
| 36 | | >4000 |
| 37 | 0.27 | 805 |
| 38 | 0.096 | 1470 |
| 39 | | >4000 |
| 40 | 0.018 | 98 |
| 41 | 0.024 | 147 |
| 42 | 0.094 | 610 |
| 43 | 0.45 | >4000 |
| 44 | 0.23 | >4000 |
| 45 | 0.025 | 32 |
| 46 | 0.0072 | 21 |
| 47 | 0.37 | 401 |
| 48 | 1 | |
| 49 | 0.16 | 332 |
| 50 | 0.016 | 340 |
| 51 | 0.018 | 31 |
| 52 | 0.0035 | 19 |
| 53 | 0.067 | 1745 |

-continued

| Ex. # | Ki data (uM) | EC50 (nM) |
|---|---|---|
| 54 | 0.14 | |
| 55 | | >4000 |
| 56 | 0.24 | 570 |
| 57 | 0.94 | |
| 58 | 0.014 | 2.5 |
| 59 | 0.17 | 2.4 |
| 60 | 0.040 | <3.9 |
| 61 | 0.022 | 19 |
| 62 | 0.015 | 15 |
| 63 | 0.02 | <3.9 |
| 64 | 0.003 | <3.9 |
| 65 | 0.68 | 67.13 |
| 66 | 0.17 | <3.9 |
| 67 | 0.28 | 20. |
| 68 | 0.0067 | 20 |
| 69 | 0.0019 | 3.0 |
| 70 | 0.0088 | 1.9 |
| 71 | 0.0052 | |
| 72 | 0.016 | 4.4 |
| 73 | 0.0016 | <3.9 |
| 74 | 0.0036 | <3.9 |
| 75 | 0.0052 | <3.9 |
| 76 | 0.0083 | <3.9 |
| 77 | 0.093 | 69 |
| 78 | 0.33 | >4000 |
| 79 | 0.039 | <3.9 |
| 80 | 0.12 | 20 |
| 81 | 0.084 | |
| 82 | 2.5 | |
| 83 | 0.058 | 84 |
| 84 | 0.034 | 455 |
| 85 | 0.10 | |
| 86 | 0.055 | |

We claim:

1. A compound of formula I,

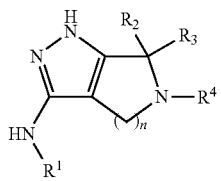

wherein:

$R^1$ is chosen from —S(O)$R^a$, —S(O)$_2R^a$, $C_1$-$C_{12}$ alkyl, $C_1$-$C_{12}$ alkyl substituted by 1 to 6 $R^5$, $C_3$-$C_{12}$ cycloalkyl, $C_3$-$C_{12}$ cycloalkyl substituted by 1 to 6 $R^5$, $C_2$-$C_{12}$ alkenyl, $C_2$-$C_{12}$ alkenyl substituted by 1 to 6 $R^5$, $C_4$-$C_{12}$ cycloalkenyl, $C_4$-$C_{12}$ cycloalkenyl substituted by 1 to 6 $R^5$, $C_2$-$C_{12}$ alkynyl, $C_2$-$C_{12}$ alkynyl substituted by 1 to 6 $R^5$, 3-12 member heterocyclyl, 3-12 member heterocyclyl substituted by 1 to 6 $R^5$, $C_1$-$C_6$ aralkyl, $C_1$-$C_6$ aralkyl substituted by 1 to 6 $R^5$, $C_1$-$C_6$ heteroaralkyl, $C_1$-$C_6$ heteroaralkyl substituted by 1 to 6 $R^5$, $C_6$-$C_{10}$ aryl, $C_6$-$C_{10}$ aryl substituted by 1 to 6 $R^5$, 5-12 member heteroaryl, and 5-12 member heteroaryl substituted by 1 to 6 $R^5$, wherein any two adjacent $R^5$ together with the atoms to which they are attached may form a fused 4-7 member ring, and the said fused ring is optionally further substituted by 1-3 $R^f$;

$R^2$ and $R^3$ are each independently chosen from —H, $C_1$-$C_6$ perfluoroalkyl, $C_1$-$C_6$ alkyl, $C_3$-$C_6$ cycloalkyl, —($C_1$-$C_3$ alkylene)-($C_3$-$C_6$ cycloalkyl), $C_2$-$C_6$ alkenyl, $C_2$-$C_6$ alkynyl, $C_1$-$C_6$ alkoxy, -(L)$_m$-halide, -(L)$_m$-CN, -(L)$_m$-OH, -(L)$_m$-NH$_2$, -(L)$_m$-($C_1$-$C_6$ monoalkylamino) and -(L)$_m$-($C_2$-$C_8$ dialkylamino), provided that $R^2$ and $R^3$ are not both H; or $R^2$ and $R^3$ may form a ring selected from $C_3$-$C_6$ cycloalkyl, $C_4$-$C_6$ cycloalkenyl and 3-6 member heterocyclyl, the said ring is optionally further substituted by 1 to 2 groups selected from $C_1$-$C_3$ alkyl, $C_1$-$C_3$ perfluoroalkyl, $C_1$-$C_3$ alkoxy, oxo, —($C_1$-$C_3$ alkylene)$_m$-halide, —($C_1$-$C_3$ alkylene)$_m$-CN, —($C_1$-$C_3$ alkylene)$_m$-OH, —($C_1$-$C_3$ alkylene)$_m$-NH$_2$, —($C_1$-$C_3$ alkylene)$_m$-($C_1$-$C_6$ monoalkylamino) and —($C_1$-$C_3$ alkylene)$_m$-($C_2$-$C_8$ dialkylamino);

$R^4$ is selected from $R^a$, —C(O)$R^a$, —C(O)NR$^a$R$^b$, —C(O)OR$^a$, —C(O)CH(R$^t$)R$^a$, —C(O)NHCH(R$^a$)R$^b$, —C(O)OCH(R$^a$)R$^b$, —C(O)CH(R$^t$)CH(R$^a$)R$^b$, —C(O)SR$^a$, —S(O)R$^a$, —S(O)NR$^a$R$^b$, —S(O)OR$^a$, —S(O)$_2$R$^a$, —S(O)$_2$NR$^a$R$^b$ and —S(O)$_2$OR$^a$, wherein R$^t$ is H or $C_1$-$C_3$ alkyl;

each $R^5$ is independently selected from R$^c$, -(L)$_m$-halide, -(L)$_m$-CN, -(L)$_m$-C(O)R$^c$, -(L)$_m$-C(O)OR$^c$, -(L)$_m$-C(O)NR$^c$R$^d$, -(L)$_m$-C(O)SR$^c$, -(L)$_m$-OR$^c$, -(L)$_m$-OC(O)R$^c$, -(L)$_m$-OC(O)NR$^c$R$^d$, -(L)$_m$-O—C(O)OR$^c$, -(L)$_m$-NO$_2$, -(L)$_m$-NR$^c$R$^d$, -(L)$_m$-N(R$^c$)C(O)R$^d$, -(L)$_m$-N(R$^c$)C(O)OR$^d$, -(L)$_m$-NR$^c$S(O)R$^d$, -(L)$_m$-NR$^c$S(O)OR$^d$, -(L)$_m$-NR$^c$S(O)$_2$R$^d$, -(L)$_m$-NR$^c$S(O)$_2$OR$^d$, -(L)$_m$-SR$^c$, -(L)$_m$-S(O)R$^c$, -(L)$_m$-S(O)OR$^c$, -(L)$_m$-S(O)$_2$R$^c$, -(L)$_m$-S(O)$_2$OR$^c$, -(L)$_m$-S(O)NR$^c$R$^d$, -(L)$_m$-S(O)$_2$NR$^c$R$^d$, -(L)$_m$-O-L-NR$^c$R$^d$, -(L)$_m$-O-L-OR$^c$ and -(L)$_m$-NR$^c$-L-OR$^d$;

each R$^a$, R$^b$, R$^c$, and R$^d$ is independently selected from H, -(L)$_m$-($C_1$-$C_6$ perfluoroalkyl), $C_1$-$C_{12}$ alkyl, —($C_1$-$C_3$ alkylene)$_m$-($C_3$-$C_{12}$ cycloalkyl), —($C_3$-$C_5$ cycloalkylene)$_m$-($C_2$-$C_{12}$ alkenyl), -(L)$_m$-($C_4$-$C_{12}$ cycloakenyl), —($C_3$-$C_5$ cycloalkylene)$_m$-($C_2$-$C_{12}$ alkynyl), -(L)$_m$-(3-12 member heterocyclyl), -(L)$_m$-($C_6$-$C_{10}$ aryl) and -(L)$_m$-(5-12 member heteroaryl), each R$^a$, R$^b$, R$^c$ and R$^d$ is independently optionally further substituted by 1-6 R$^f$; R$^a$ and R$^b$, or R$^c$ and R$^d$, together with the atom to which they are attached, may optionally form a ring selected from 3-12 member heterocyclyl and 5-12 member heteroaryl, the said ring is optionally further substituted by 1-6 R$^f$;

each R$^f$ is independently selected from oxo, —($C_1$-$C_3$ alkylene)$_m$-($C_1$-$C_6$ perfluoalkyl), $C_1$-$C_{12}$ alkyl, $C_2$-$C_6$ alkenyl, $C_2$-$C_6$ alkynyl, —($C_1$-$C_3$ alkylene)$_m$-($C_3$-$C_7$ cycloalkyl), —($C_1$-$C_3$ alkylene)$_m$-(3-7 member heterocyclyl), —($C_1$-$C_3$ alkylene)$_m$-(5-7 member heteroaryl), -(L)$_m$-halide, -(L)$_m$-CN, -(L)$_m$-C(O)R$^k$, -(L)$_m$-C(O)OR$^k$, -(L)$_m$-C(O)NR$^k$R$^j$, -(L)$_m$-OR$^k$, -(L)$_m$-OC(O)R$^k$, -(L)$_m$-NO$_2$, -(L)$_m$-NR$^k$R$^j$, -(L)$_m$-N(R$^k$)C(O)R$^j$, -(L)$_m$-O-L-NR$^k$R$^j$, -(L)$_m$-SR$^k$, -(L)$_m$-S(O)R$^k$, -(L)$_m$-S(O)$_2$R$^j$R$^k$, each R$^f$ is independently optionally further substituted by 1-3 groups selected from $C_1$-$C_3$ alkyl, halide and $C_1$-$C_3$ perfluoroalkyl;

each R$^k$ and R$^j$ is independently —H, —OH, $C_1$-$C_3$ perfluoroalkyl, $C_1$-$C_6$ alkyl, $C_2$-$C_6$ alkenyl, $C_3$-$C_6$ alkynyl, —($C_1$-$C_3$ alkylene)$_m$-($C_3$-$C_6$ cycloalkyl) or —($C_1$-$C_3$ alkylene)$_m$-(3 to 6 member heterocyclyl), R$^k$ and R$^j$ may optionally form a ring selected from 3-7 member heterocyclyl and 5-7 member heteroaryl, the said ring is optionally further substituted by 1 to 2 groups selected from $C_1$-$C_3$ alkyl, $C_1$-$C_3$ perfluoroalkyl, $C_1$-$C_3$ alkoxy, oxo, —($C_1$-$C_3$ alkylene)$_m$-halide, —($C_1$-$C_3$ alkylene)$_m$-CN, —($C_1$-$C_3$ alkylene)$_m$-OH, —($C_1$-$C_3$ alkylene)$_m$-NH$_2$, —($C_1$-$C_3$ alkylene)$_m$-($C_1$-$C_6$ monoalkylamino) and —($C_1$-$C_3$ alkylene)$_m$-($C_2$-$C_8$ dialkylamino);

each L is independently a bivalent radical selected from —($C_1$-$C_6$ alkylene)-, —($C_3$-$C_7$ cycloalkylene)-, —($C_1$-$C_6$ alkylene)-($C_3$-$C_7$ cycloalkylene)- and —($C_3$-$C_7$ cycloalkylene)-($C_1$-$C_6$ alkylene)-;

each m is independently 0 or 1; and n is 1, 2, or 3;

or a pharmaceutically acceptable salt thereof.

2. The compound of claim 1, or a pharmaceutically acceptable salt thereof, wherein n is 1; $R^2$ is unsubstituted methyl; $R^3$ is unsubstituted methyl; $R^4$ is —C(O)NHCH($R^a$)$R^b$, —C(O)OCH($R^a$)$R^b$ or —C(O)CH($R^t$)CH($R^a$)$R^b$; $R^1$ is 5-12 member heteroaryl; and $R^1$ is optionally further substituted as by 1-5 $R^5$;

each $R^5$ is independently -($L^1$)$_m$-($C_1$-$C_6$ perfluoalkyl), $C_1$-$C_6$ alkyl, $C_2$-$C_6$ alkenyl, $C_2$-$C_6$ alkynyl, —($C_1$-$C_3$ alkylene)$_m$-($C_3$-$C_4$ cycloalkyl), —($C_1$-$C_3$ alkylene)$_m$-(3-4 member heterocyclyl) optionally substituted by 1-2 $C_1$-$C_3$ alkyl, -($L^1$)$_m$-halide, -($L^1$)$_m$-CN, -($L^1$)$_m$-C(O)$R^k$, -($L^1$)$_m$-C(O)O$R^k$, -($L^1$)$_m$-C(O)N$R^k R^j$, -($L^1$)$_m$-C(O)S$R^j$, -($L^1$)$_m$-O$R^k$, -($L^1$)$_m$-OC(O)$R^k$, -($L^1$)$_m$-OC(O)N$R^j R^k$, -($L^1$)$_m$-NO$_2$, -($L^1$)$_m$-N$R^k R^j$, -($L^1$)$_m$-N($R^k$)C(O)$R^j$, -($L^1$)$_m$-N($R^k$)C(O)O$R^j$, -($L^1$)$_m$-O-$L^1$-N$R^k R^j$, -($L^1$)$_m$-O-$L^1$-O$R^k$, -($L^1$)$_m$-N$R^j$-$L^1$-O$R^k$, -($L^1$)$_m$-S$R^k$, -($L^1$)$_m$-S(O)$R^k$, -($L^1$)$_m$-S(O)O$R^k$, -($L^1$)$_m$-S(O)N$R^j R^k$, -($L^1$)$_m$-S(O)$_2$$R^k$, -($L^1$)$_m$-S(O)$_2$O$R^k$ or -($L^1$)$_m$-S(O)$_2$N$R^j R^k$, wherein each $R^j$; and $R^k$ is independently H, OH, $C_1$-$C_3$ alkyl or $C_1$-$C_3$ perfluoroalkyl, or $R^j$; and $R^k$ on the same nitrogen forms a 3-4 member ring selected from aziridinyl and azetidinyl; $L^1$ is a bivalent radical selected from —($C_1$-$C_3$ alkylene)-, —($C_3$-$C_4$ cycloalkylene)-, -(3-4 member heterocyclylene)-, —($C_1$-$C_3$ alkylene)-($C_3$-$C_4$ cycloalkylene)-, —($C_3$-$C_4$ cycloalkylene)-($C_1$-$C_3$ alkylene)-, —($C_1$-$C_3$ alkylene)-(3-4 member heterocyclylene)- and -(3-4 member heterocyclylene)-($C_1$-$C_3$ alkylene)-.

3. A pharmaceutical composition comprising a compound of claim 1, or a pharmaceutically acceptable salt thereof, and a pharmaceutically acceptable excipient.

4. The compound of claim 1, or a pharmaceutically acceptable salt thereof, wherein n is 1.

5. The compound of claim 1, or a pharmaceutically acceptable salt thereof, wherein each $R^2$ and $R^3$ is independently selected from H, unsubstituted $C_1$-$C_3$ alkyl and unsubstituted $C_3$-$C_5$ cycloalkyl, or $R^2$ and $R^3$ form a ring selected from unsubstituted cyclopropyl, unsubstituted cyclobutyl and unsubstituted cyclopentyl.

6. The compound of claim 1, or a pharmaceutically acceptable salt thereof, wherein $R^2$ is unsubstituted methyl and $R^3$ is unsubstituted methyl.

7. The compound of claim 1, or a pharmaceutically acceptable salt thereof, wherein $R^4$ is selected from —C(O)NHCH($R^a$)$R^b$, —C(O)OCH($R^a$)$R^b$ and C(O)CH($R^t$)CH($R^a$)$R^b$.

8. The compound of claim 7, or a pharmaceutically acceptable salt thereof, wherein $R^a$ is selected from phenyl, 5-12 member heteroaryl, 3-12 member heterocyclyl and 3-12 member cycloalkyl, where $R^a$ is optionally further substituted by 1-6 $R^f$, and $R^b$ is a methyl group substituted by N$R^j R^k$.

* * * * *